United States Patent
Hagel et al.

(10) Patent No.: US 11,845,726 B2
(45) Date of Patent: Dec. 19, 2023

(54) $C_4$-CARBONOTHIOATE-SUBSTITUTED TRYPTAMINE DERIVATIVES AND METHODS OF USING

(71) Applicant: Enveric Biosciences Canada Inc., Calgary (CA)

(72) Inventors: Jillian M. Hagel, Calgary (CA); Kaveh Matinkhoo, Calgary (CA); Peter J. Facchini, Calgary (CA)

(73) Assignee: ENVERIC BIOSCIENCES CANADA INC., Calgary (CA)

( * ) Notice: Subject to any disclaimer, the term of this patent is extended or adjusted under 35 U.S.C. 154(b) by 0 days.

(21) Appl. No.: 17/893,113

(22) Filed: Aug. 22, 2022

(65) Prior Publication Data

US 2023/0295085 A1     Sep. 21, 2023

Related U.S. Application Data

(60) Provisional application No. 63/347,835, filed on Jun. 1, 2022, provisional application No. 63/321,440, filed on Mar. 18, 2022.

(51) Int. Cl.
    *C07D 209/16*     (2006.01)
(52) U.S. Cl.
    CPC ................... *C07D 209/16* (2013.01)
(58) Field of Classification Search
    CPC .................................. C07D 209/16
    See application file for complete search history.

(56) References Cited

PUBLICATIONS

Synthesis 1999, No. 6, pp. 935-938.*
Haleem, Darakhshan. Behav. Pharm. 2015, 26:45-58.
McClure-Begley, T.D. et al. Nat. Rev. Drug Discov. 2022, 21:463-473.
Cao, D. et al. Science 2022, 375:403-411.
Devroye, C. et al. Pharmacol. Ther. 2018, 181:143-155.
Orsolini, L. et al. Expert Rev. Neurother. 2016, 16:483-95.
Chmielarz, Piotr et al. Int. J. Mol Sci. 2021, 22: 4817.
Hirota, Tomoya et al. J. Am. Acad. Child. Adolesc. Psychiatry 2014, 53:153-73.
Morris, G. et al. Pharmacol. Res. 2021, 170: 105729.
Outhred, T. et al. Neurosci. Biobehav. Rev, 2013, 37:1786-800.
Taciak P.P. et al. Pharmacol. Rep. 2018, 70:37-46.
Finnin, B. and Morgan, T.M., 1999 J. Pharm. Sci, 88 (10), 955-958.
Romeo, B. et al. J. Psychiatr. Res 137: 273-282, 2021.
Cameron and Olson 2018, ACS Chem Neurosci. 9: 2344.
Williams, FM 1987, Pharmacology and Therapeutics, 34:99-109.
Dinis-Oliveira, RJ 2017, Drug Metabolism Reviews, 49(1):84-91.
Henrikus and Kampffmeyer, 1992, Xenobiotica 22: 1357-1366.
Daniel, J. et al. Mental Health Clin., 2017;7(1): 24-28.
Grob, C. et al. Arch. Gen. Psychiatry, 2011, 68(1) 71-78.
Cathart-Harris, R.L. et al. Lancet Psychiatry, 2016, 3: 619-627.
Bodor, N. et al., 2001, J. Pharmacy and Pharmacology, 53: 889-894.
Vitale, A. et al., 2011, J. of Nucl. Med, 52(6), 970-977.
Inserra et al., 2020, Pharmacol. Rev 73: 202.
Amidfar, Meysam. Curr. Pharm. Des. 2018, 24:2541-2548.
Segelcke, D. et al. Cephalalgia 2017, 37:365-371.
Doze, V.A. et al. Brain Res. 1285 2009, 148-157.
Dulawa, S.C. et al. Mol. Psychiatry 2019, 24: 694-709.
Cervenka, Simon. Neurosci. Lett. 2019, 691:26-34.
Tiihonen, J. et al. Mol. Psychiatry 2020, 25:3432-3441.
Engin, Elif et al. Trends Pharmacol. Sci. 2018, 39:710-732.
Zhang, W. et al. Transl. Psychiatry 2022, 12:243.
Salatino-Oliverira A. et al. Am. J. Med. Genet. B Neuropsychiatr. Genet. 2018, 177:211-231.
Botti et al., 2021 Pharmaceutics 13:1114.
Ross, S. ACS Pharmacol. Transl. Sci. 4: 553-562, 2021.
Terrasso et al., 2017, J. Pharmacol. Toxicol. Methods 83: 72.
Pyrgiotakis G. et al., 2009, Ann. Biomed. Eng. 37: 1464-1473.
Weaver et al., 2017, Expert Opin. Drug Metab. Toxicol. 13: 767.
Donato et al., 2015, Methods Mol Biol 1250: 77.
Fang 2012, Exp. Opin. Drug Discov. 7:969.
Núñez et al., 2012, Drug Disc. Today 17: 10.
Maguire et al., 2012, Methods Mol Biol 897: 31.
McKenna and Peroutka 1989, J. Neurosci. 9: 3482.
Rojas and Fiedler 2016, Front Cell Neurosci. 10: 272.
Eddershaw et al., 2000, Drug Discovery Today 5(9): 409-414.
Ackley et al., 2004, Methods in Pharmacology and Toxicology Optimization in Drug Discovery (in vitro methods), Yan Z, Caldwell G.W. Eds; Humana Press Inc, New Jersey, pp. 151-164.
Richardson et al., 2016 Drug Metabolism Letters 10:83-90.
Hatley et al., 2017, Biopharmaceuticals & Drug Disposition, 38(2):155-160.
Zawilska JB, et al. 2013, Pharmacological Reports, 65:1-14.
Menéndez-Perdomo et al., 2021, J. Mass Spectrom., 56: e4683.
Dinis-Oliveira, 2017 Drug Metab. Rev. 49: 84-91.

* cited by examiner

*Primary Examiner* — Kamal A Saeed
(74) *Attorney, Agent, or Firm* — BERESKIN & PARR LLP/S.E.N.C.R.L., s.r.l.; Michael Fenwick

(57) ABSTRACT

Disclosed are novel $C_4$-carbonothioate-substituted tryptamine derivative compounds and pharmaceutical and recreational drug formulations containing the same. The pharmaceutical formulations may be used to treat brain neurological disorders.

16 Claims, 29 Drawing Sheets

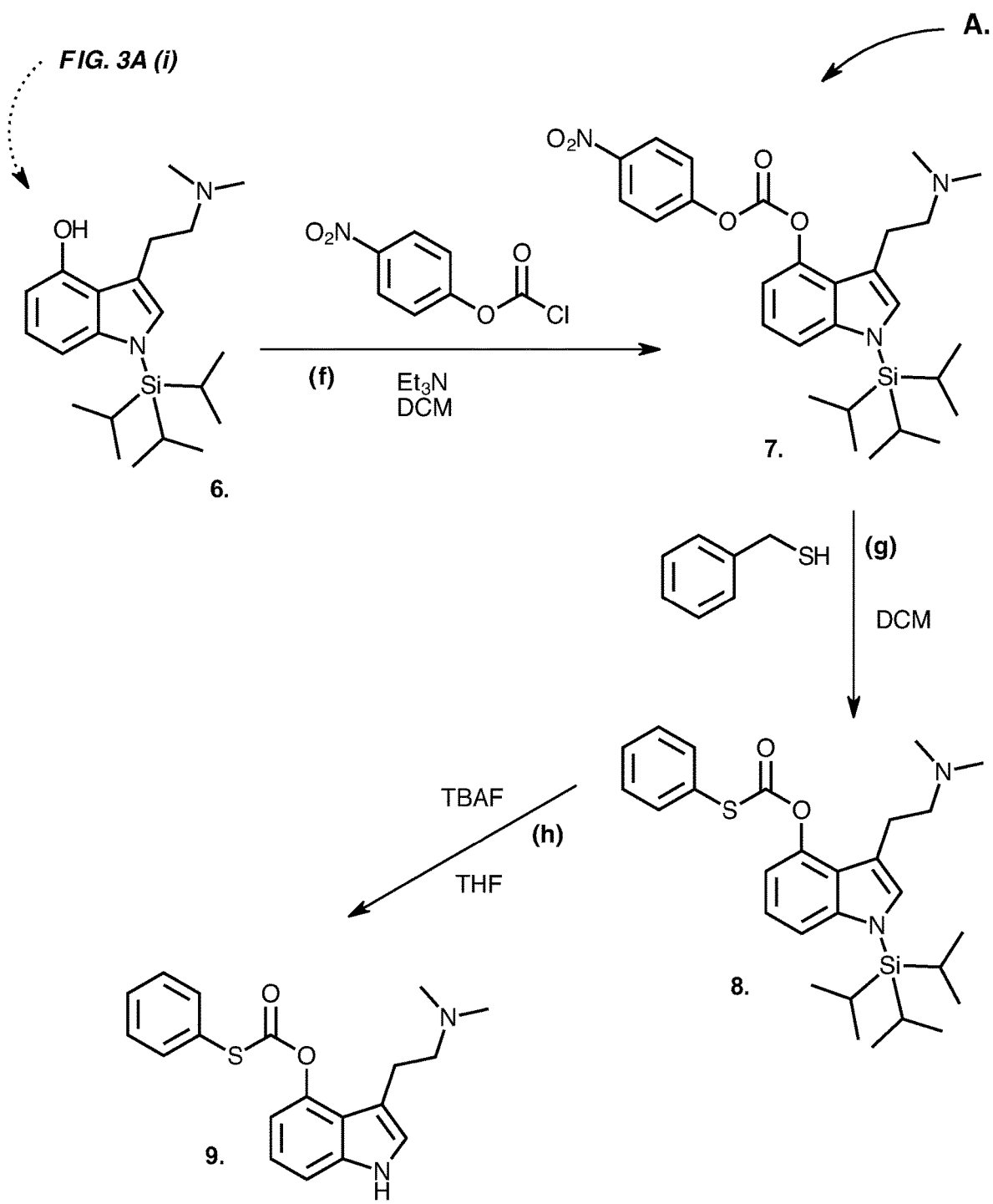
FIG. 3A (ii)

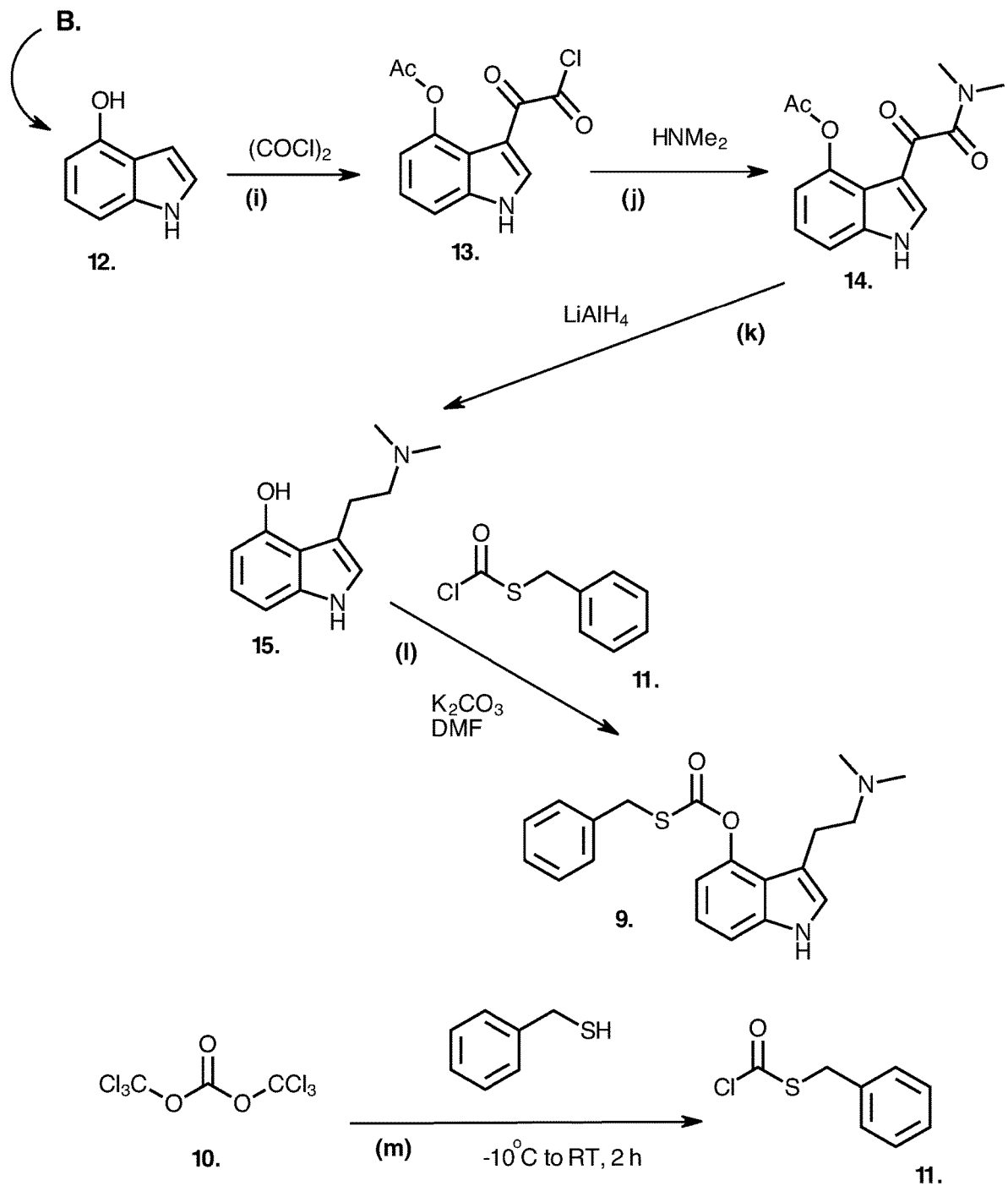
FIG. 3A (iii)

EC50: 7.697 uM (+ 5-HT$_{1A}$)

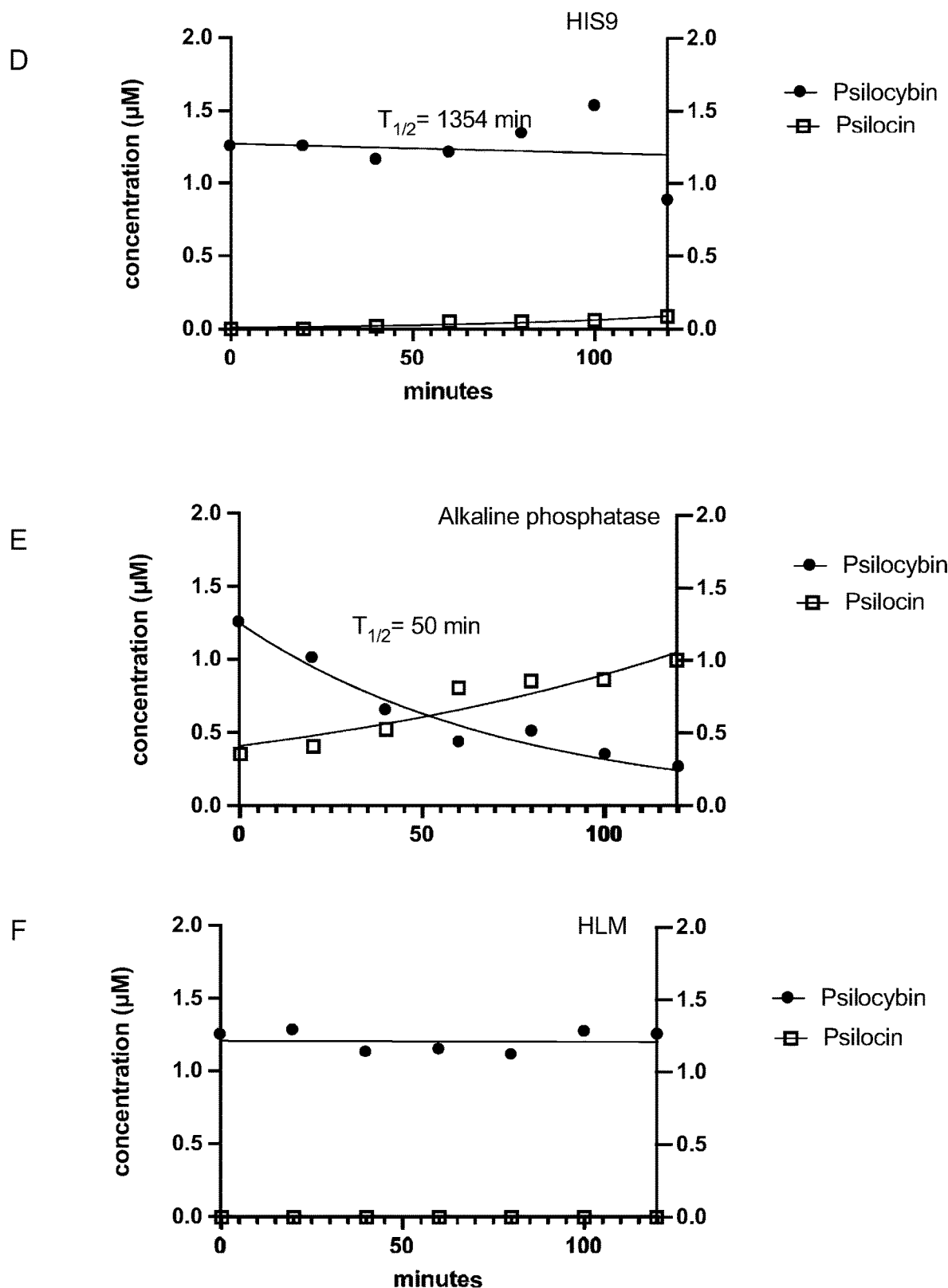
FIG. 3M (ii)

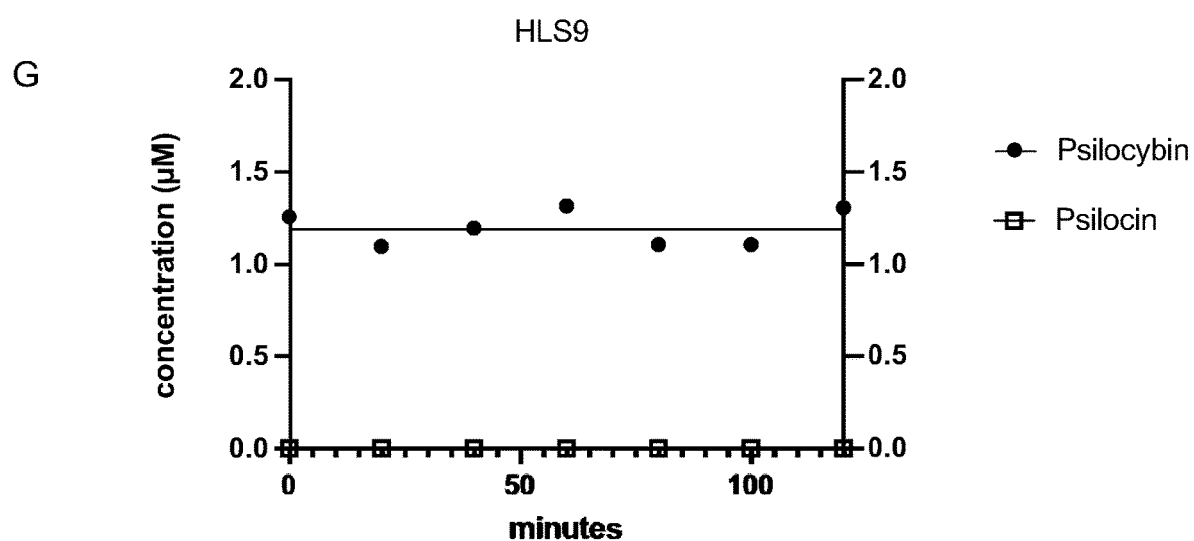
FIG. 3M (iii)

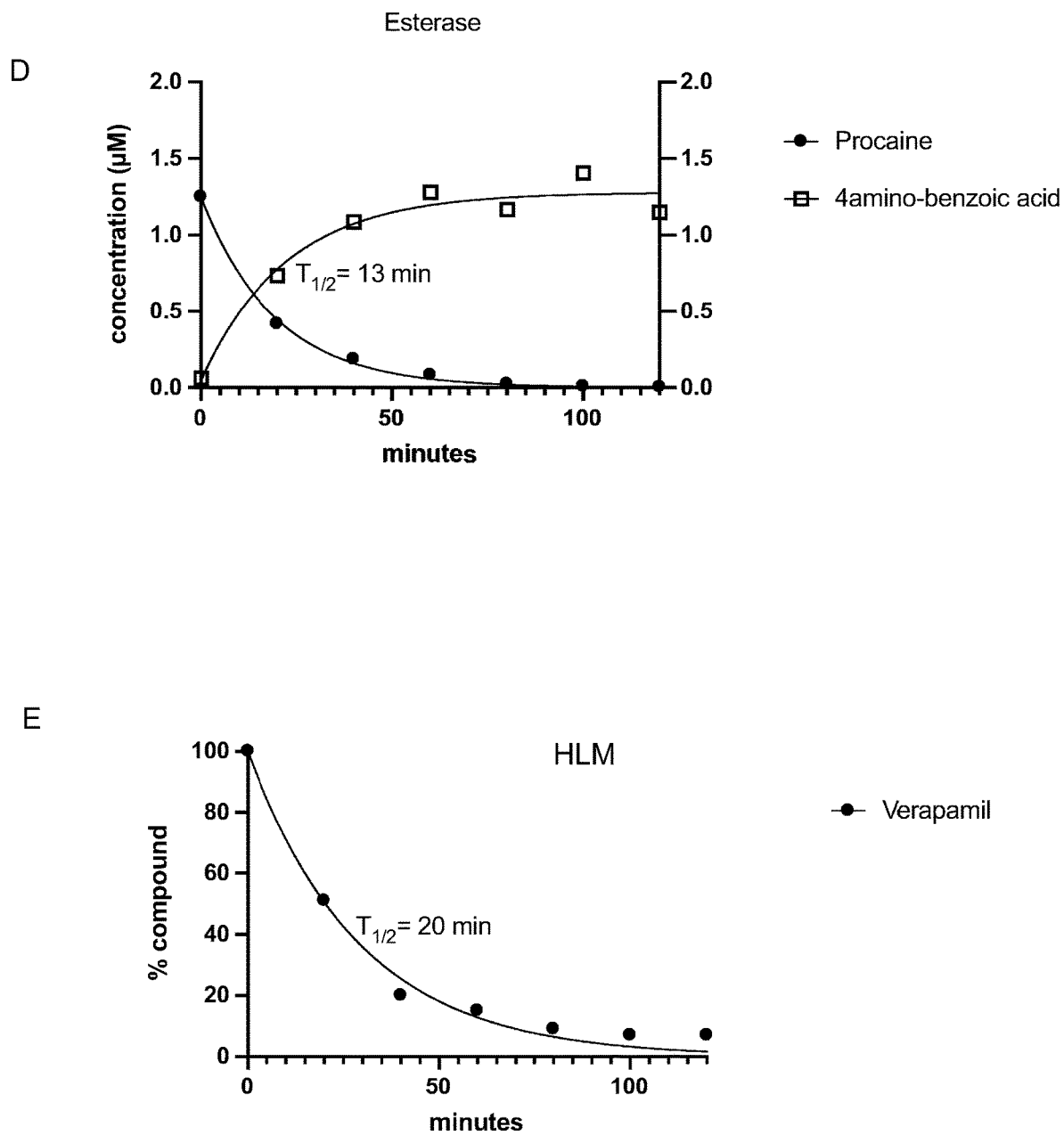
FIG. 3N (ii)

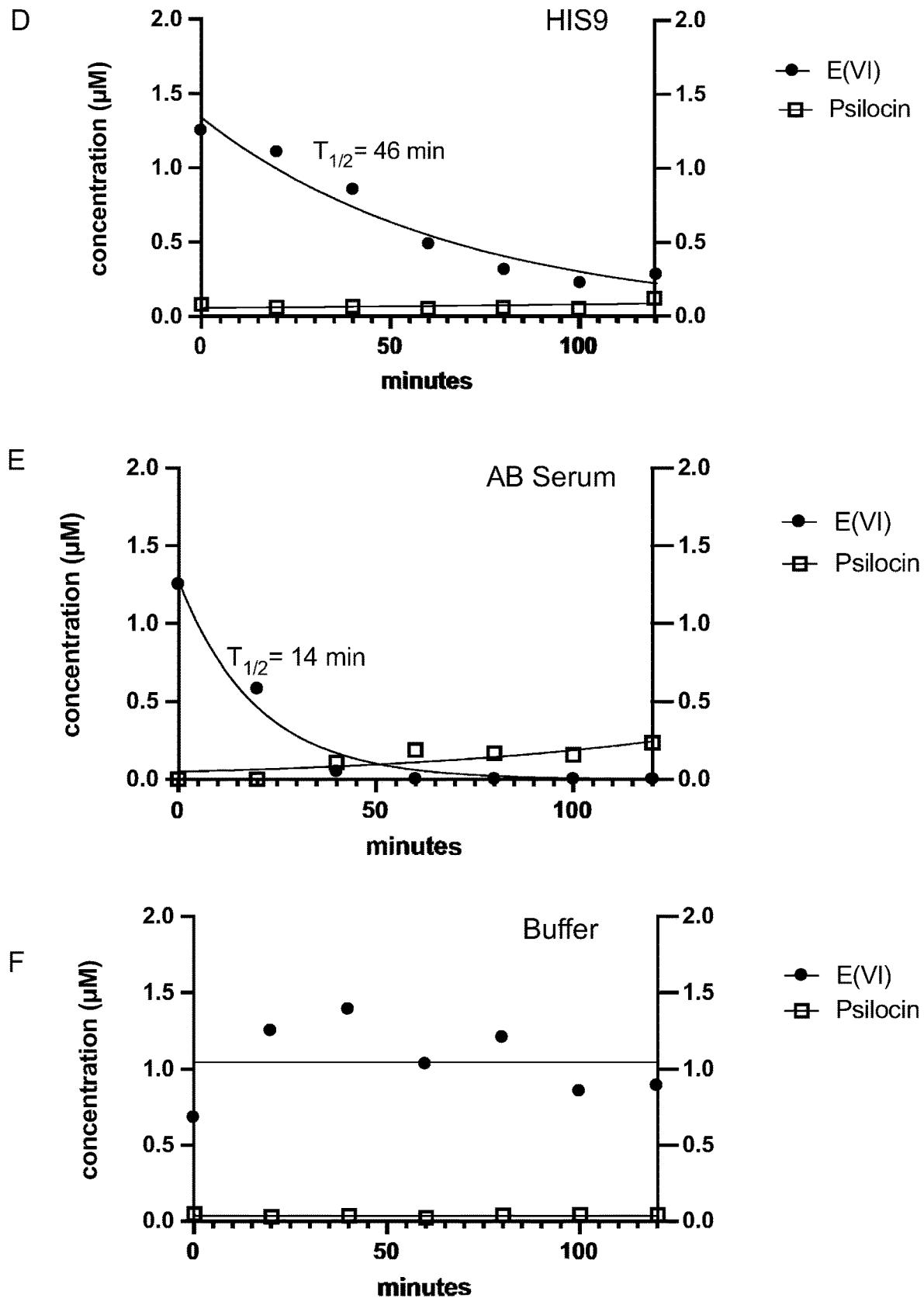
FIG. 3O (ii)

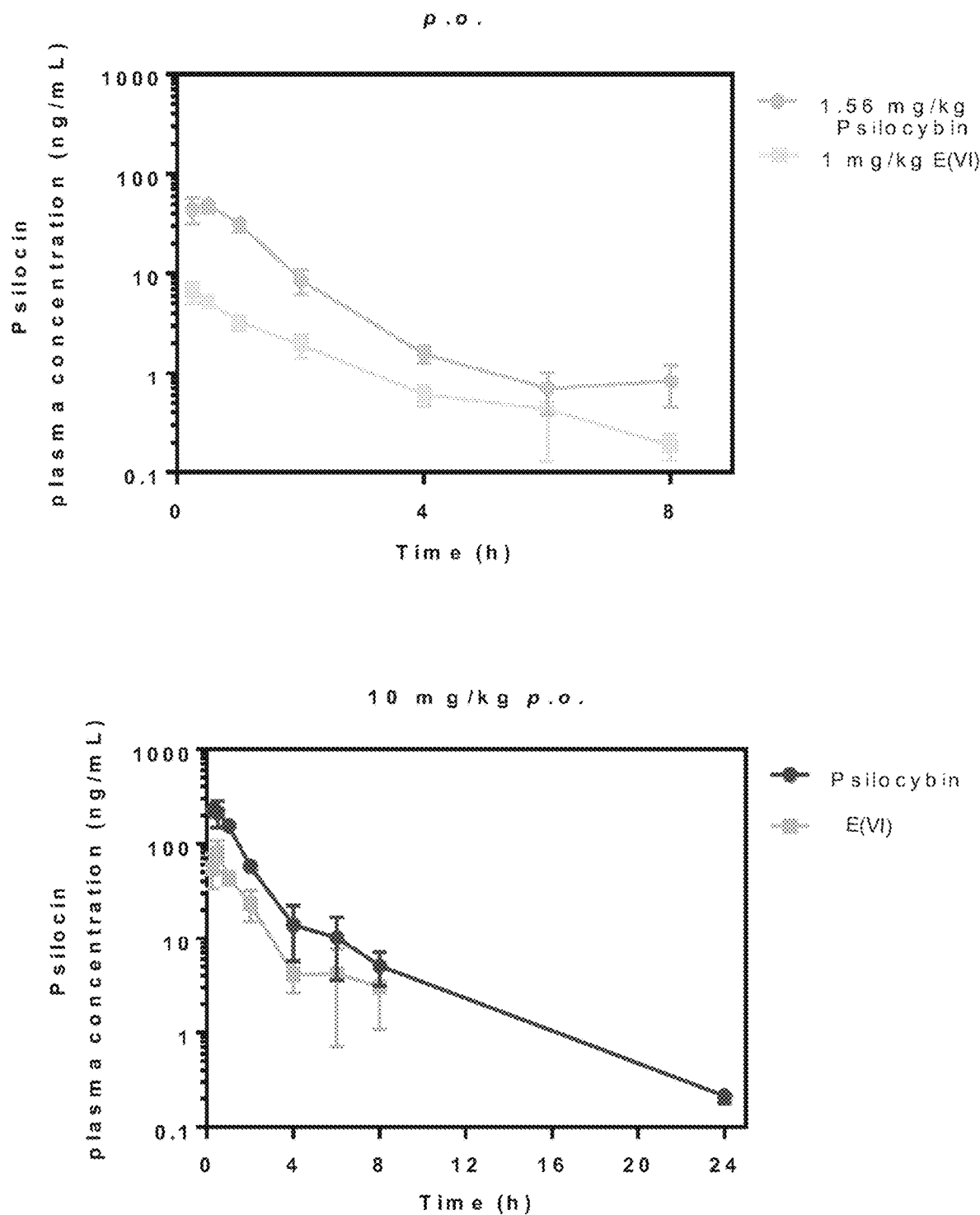
FIG. 3S (ii)

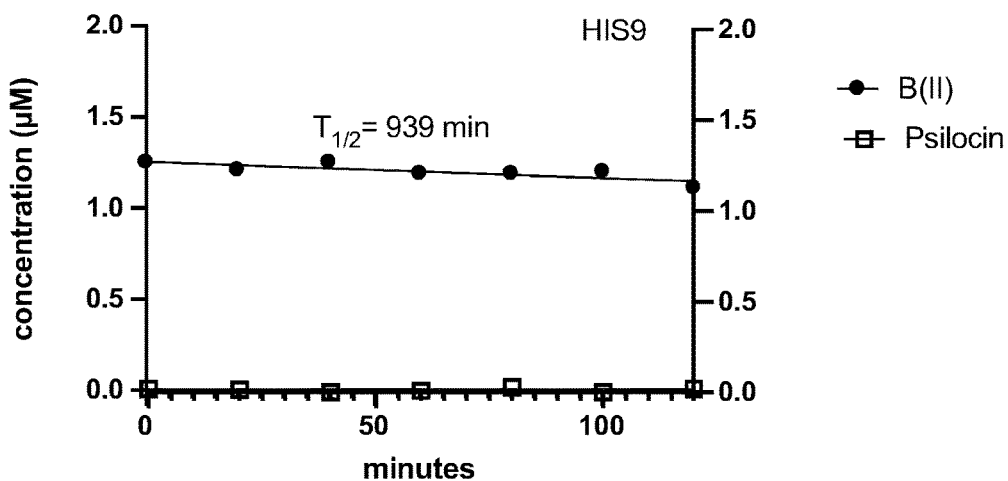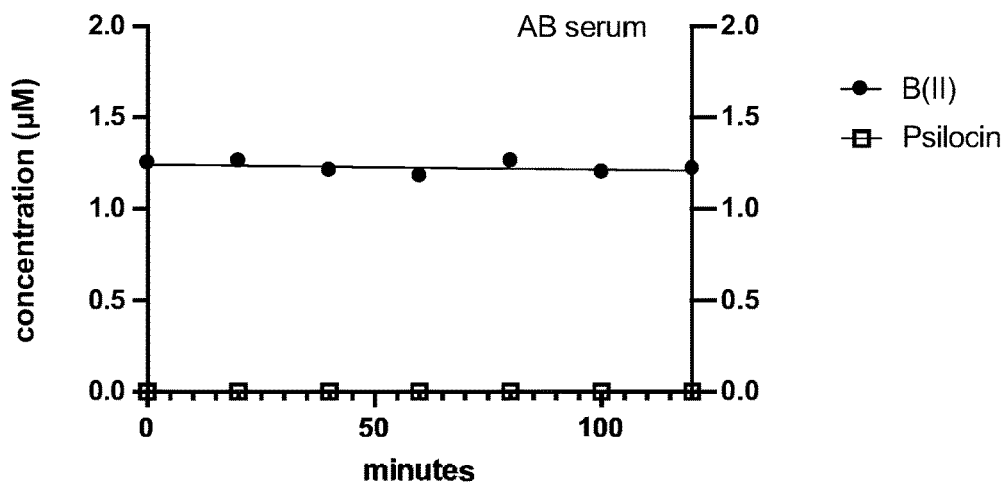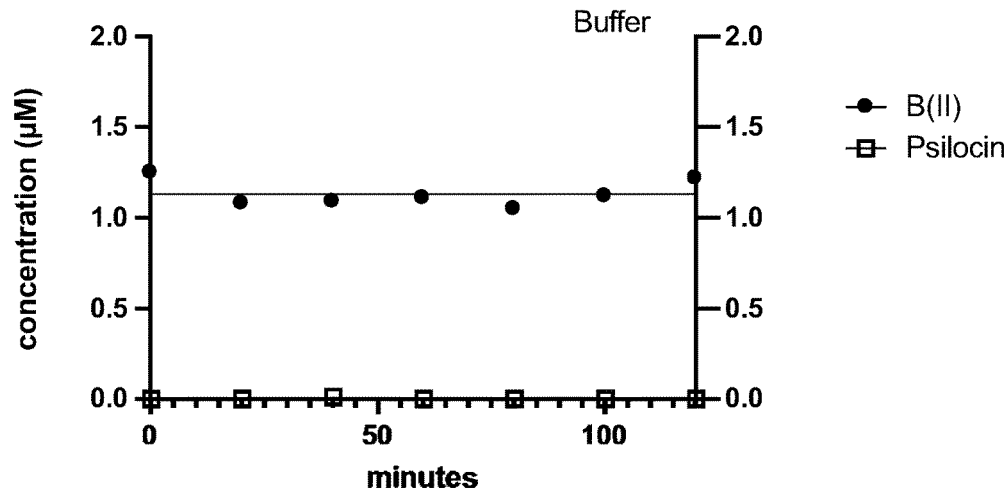
FIG. 4D (ii)

$C_4$-CARBONOTHIOATE-SUBSTITUTED TRYPTAMINE DERIVATIVES AND METHODS OF USING

RELATED APPLICATIONS

This application claims the benefit of U.S. Provisional Application No. 63/321,440, filed Mar. 18, 2022, and U.S. Provisional Application No. 63/347,835, filed Jun. 1, 2022; the entire contents of U.S. Provisional Patent Application Nos. 63/321,440 and 63/347,835 are hereby incorporated by reference.

FIELD OF THE DISCLOSURE

The compositions and methods disclosed herein relate to a class of chemical compounds known as tryptamines. Furthermore, the compositions and methods disclosed herein relate to $C_4$-substituted tryptamine derivatives, and, in particular, to $C_4$-carbonothioate-substituted tryptamine derivatives.

BACKGROUND OF THE DISCLOSURE

The following paragraphs are provided by way of background to the present disclosure. They are not however an admission that anything discussed therein is prior art or part of the knowledge of a person of skill in the art.

Tryptamines are a class of chemical compounds that share a common chemical structure (notably, a fused benzene and pyrrole ring, together known as an indole, and linked to the pyrrole ring, at the third carbon atom, a 2-aminoethyl group), and can be formulated as therapeutic drug compounds. For example, psilocybin has been evaluated as a drug for its clinical potential in the treatment of mental health conditions (Daniel, J. et al. Mental Health Clin., 2017; 7(1): 24-28), including to treat anxiety in terminal cancer patients (Grob, C. et al. Arch. Gen. Psychiatry, 2011, 68(1) 71-78) and to alleviate symptoms of treatment-resistant depression (Cathart-Harris, R. L. et al. Lancet Psychiatry, 2016, 3: 619-627). Other known drug compounds within the tryptamine class of compounds include, for example, melatonin, serotonin, bufotenin, dimethyltryptamine (DMT), and psilocin.

It is commonly understood that tryptamine-based drugs can produce their in vivo therapeutic effects by molecular interaction with macromolecules present in human cells, known as receptors. In this respect, in broad terms, specific receptors can be thought of as being located in a relatively fixed anatomical space (e.g., a specific brain tissue). Following administration of a drug, the drug moves through the body to the receptor to interact therewith, and then back out of the body. It is generally desirable that when a tryptamine-based drug is administered, the drug is specifically active at the desired anatomical location within a patient's body, such as, for example, in a specific brain tissue and/or at a specific receptor, a 5-hydroxytryptamine (5-HT) receptor, for example. Moreover, it is generally desirable that the specific molecular interaction between the drug and a receptor, such as a 5-HT receptor, is such that the drug-receptor molecular interaction results in appropriate modulation of the target receptor.

In many instances the observed pharmacological effect of tryptamine-based drugs is suboptimal. Thus, administration of the drug may fall short of the desired therapeutic effect (e.g., the successful treatment of a psychotic disorder) and/or undesirable side effects may be observed.

The underlying causes for these observed shortcomings in pharmacological effects may be manifold. For example, the administered drug additionally may interact with receptors other than the target receptor, and/or the specific molecular interaction between drug and target may not lead to the desired receptor modulation, and/or the concentration of the drug at the receptor may be suboptimal. In this respect, known tryptamine-based drugs can be said to frequently display suboptimal pharmacodynamic (PD) characteristics, i.e., suboptimal characteristics with respect to the pharmacological effect exerted by the drug on the body. Thus, for example, the intensity of the drug's effect, the concentration of the drug at the receptor, and the molecular interactions between the drug and receptor may not be as desired.

Furthermore, as is the case with many pharmaceutical compounds, tryptamine compounds when administered can penetrate multiple tissues by diffusion, resulting in broad bodily distribution of the drug compound (Bodor, N. et al., 2001, J. Pharmacy and Pharmacology, 53: 889-894). Thus, frequently a substantial proportion of the administered drug fails to reach the desired target receptor. This in turn may necessitate more frequent dosing of the drug. Such frequent dosing is less convenient to a patient, and, moreover, may negatively affect patient compliance with the prescribed drug therapy. In addition, generally toxicity associated with drug formulations tends to be more problematic as a result of broad bodily distribution of the drug throughout the patient's body since undesirable side effects may manifest themselves as a result of interaction of the drug with healthy organs.

Furthermore, it is generally desirable that drug compounds exert a pharmacological effect for an appropriate period of time. However, tryptamine-based drugs when systemically administered to a patient can exhibit a high blood plasma clearance, typically on the order of minutes (Vitale, A. et al., 2011, J. of Nucl. Med, 52(6), 970-977). Thus, rapid drug clearance can also necessitate more frequent dosing of tryptamine-based drug formulations. In this respect, known tryptamine containing drug formulations can be said to frequently display suboptimal pharmacokinetic (PK) characteristics, i.e., suboptimal characteristics with respect to movement of the drug through the body to and from the desired anatomical location, including, for example, suboptimal drug absorption, distribution, metabolism, and excretion.

There exists therefore a need in the art for improved tryptamine compounds.

SUMMARY OF THE DISCLOSURE

The following paragraphs are intended to introduce the reader to the more detailed description, not to define or limit the claimed subject matter of the present disclosure.

In one aspect, the present disclosure relates to tryptamines and derivative compounds thereof.

In another aspect, the present disclosure relates to $C_4$-substituted tryptamine derivative compounds.

In another aspect, the present disclosure relates to $C_4$-carbonothioate-substituted tryptamine derivative compounds.

Accordingly, in one aspect, the present disclosure provides, in at least one embodiment, in accordance with the teachings herein, a chemical compound having chemical formula (I):

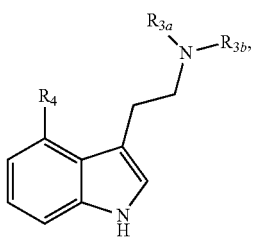

(I)

wherein R₄ is a carbonothioate moiety or a derivative thereof; and wherein $R_{3a}$ and $R_{3b}$ are each independently a hydrogen atom, an alkyl group, or an aryl group.

In at least one embodiment, in an aspect, the carbonothioate moiety or derivative thereof can have the chemical formula (III):

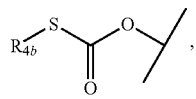

(III)

wherein $R_{4b}$ is an alkyl group, a cyclo-alkyl group, or an aryl group, each of which are optionally substituted.

In at least one embodiment, in an aspect, the carbonothioate moiety or derivative thereof can have the chemical formula (IV):

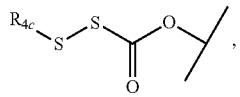

(IV)

wherein $R_{4c}$ is an alkyl group, a cyclo-alkyl group, or an aryl group, each of which are optionally substituted.

In at least one embodiment, in an aspect, $R_{4b}$ can be $C_1$-$C_6$ alkyl optionally substituted with a halogen atom, alkyl group, cycloalkyl group, or an aryl group.

In at least one embodiment, in an aspect, $R_{4b}$ can be $C_1$-$C_3$ alkyl optionally substituted with a halogen atom, alkyl group, cycloalkyl group, or an aryl group.

In at least one embodiment, in an aspect, the aryl group can be a phenyl group.

In at least one embodiment, in an aspect, $R_{4b}$ can be methyl, ethyl, isopropyl, butyl, —CH₂-cyclopropyl, —CH(CH₃)-cyclopropyl, —C(CH₃)₂-cyclopropyl or —CH₂-phenyl.

In at least one embodiment, in an aspect, $R_{4b}$ can be an aryl group.

In at least one embodiment, in an aspect, the aryl group can be a phenyl group.

In at least one embodiment, in an aspect, $R_{4b}$ can be $C_1$-$C_6$ alkyl optionally substituted with a halogen atom, alkyl group, cycloalkyl group, or aryl group, and wherein one or more of the carbon atoms in the $C_1$-$C_6$ alkyl group are optionally replaced with oxygen (O) atoms.

In at least one embodiment, in an aspect, $R_{4c}$ can be $C_1$-$C_6$ alkyl optionally substituted with a halogen atom, alkyl group, cycloalkyl group, or an aryl group.

In at least one embodiment, in an aspect, the aryl group can be a phenyl group.

In at least one embodiment, in an aspect, $R_{4c}$ can be methyl, ethyl, isopropyl, butyl, —CH₂-cyclopropyl, —CH(CH₃)-cyclopropyl, —C(CH₃)₂-cyclopropyl or —CH₂-phenyl.

In at least one embodiment, in an aspect, $R_{4c}$ can be an aryl group.

In at least one embodiment, in an aspect, the aryl group can be a phenyl group.

In at least one embodiment, in an aspect, $R_{4c}$ can be $C_1$-$C_6$ alkyl optionally substituted with a halogen atom, alkyl group, cycloalkyl group, or aryl group, and wherein one or more of the carbon atoms in the $C_1$-$C_6$ alkyl group are optionally replaced with oxygen (O) atoms.

In at least one embodiment, in an aspect, the compound can be selected from the group consisting of E(I), E(II), E(III), E(IV), E(V), E(VI), E(VII), E(VIII), E(IX), E(X), E(XI), E(XII), E(XIII), E(XIV), E(XV), E(XVI), E(XVII), E(XVIII), E(XIX), and E(XX):

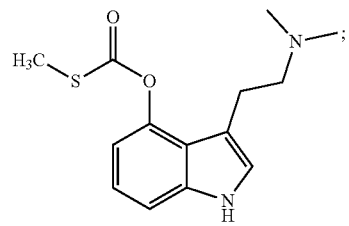

E(I)

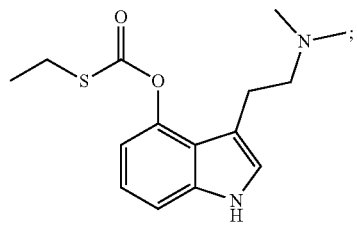

E(II)

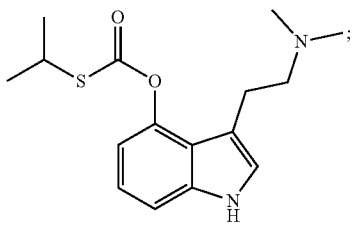

E(III)

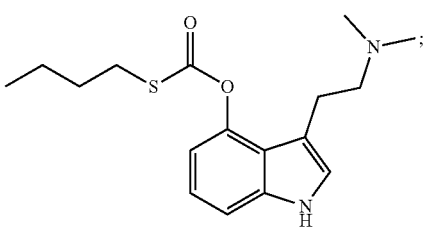

E(IV)

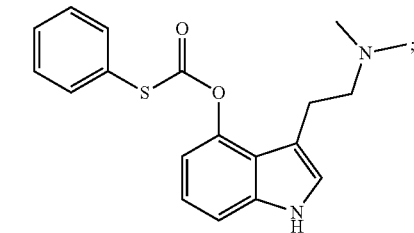
E(V)
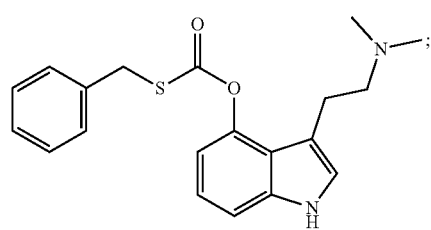
E(VI)
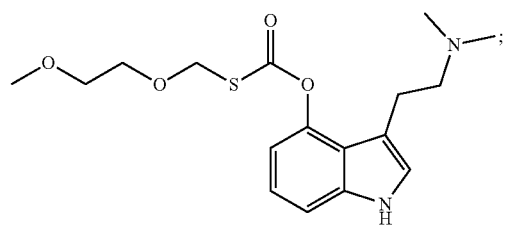
E(VII)
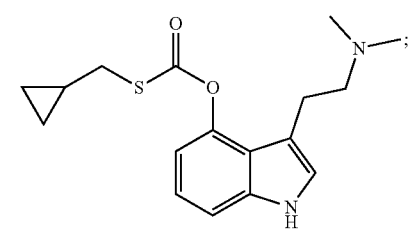
E(VIII)
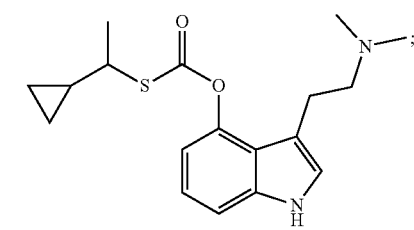
E(IX)
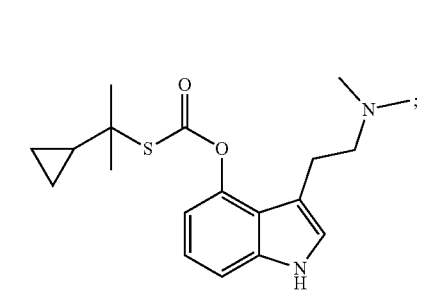
E(X)
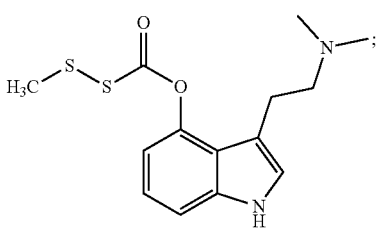
E(XI)
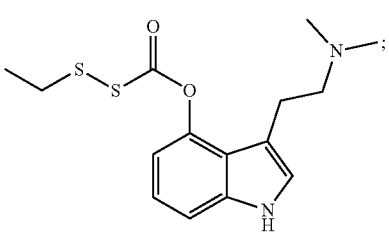
E(XII)
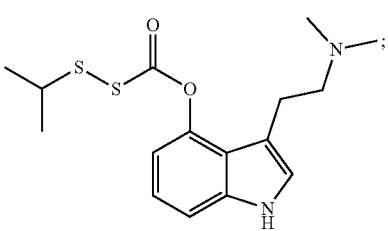
E(XIII)
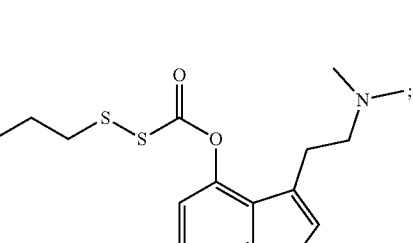
E(XIV)
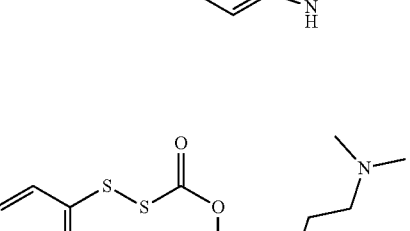
E(XV)
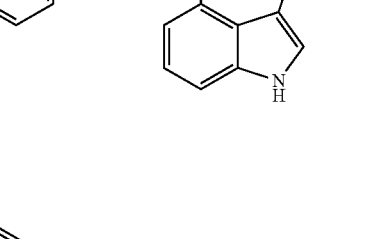
E(XVI)

-continued

E(XVII)

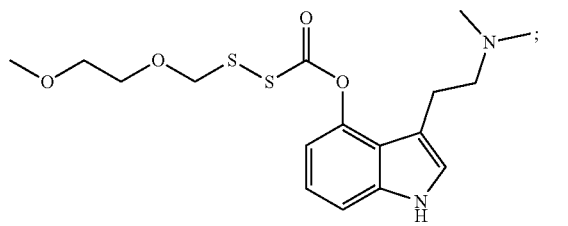

E(XVIII)

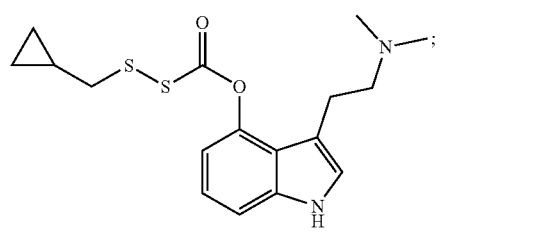

E(XIX) and

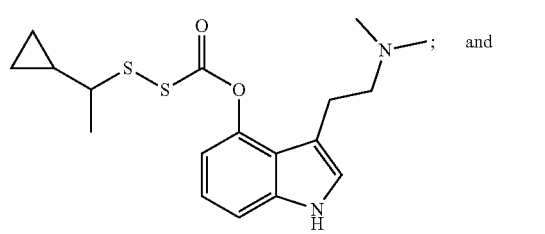

E(XX)

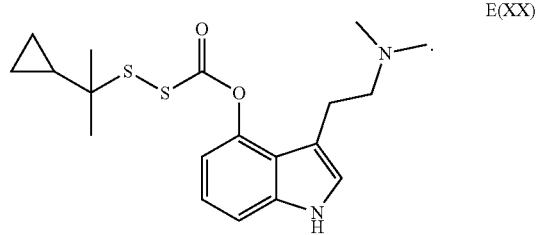

In another aspect, the present disclosure relates to pharmaceutical and recreational drug formulations comprising $C_4$-carbonothioate substituted tryptamine derivative compounds. Accordingly, in one aspect, the present disclosure provides, in at least one embodiment, a pharmaceutical or recreational drug formulation comprising an effective amount of a chemical compound having a formula (I):

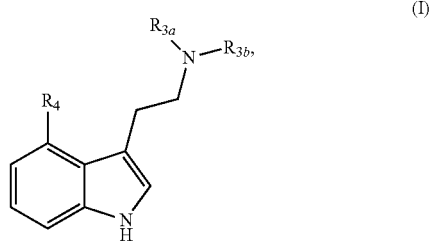

(I)

wherein $R_4$ a carbonothioate moiety or derivative thereof; and wherein $R_{3a}$ and $R_{3b}$ are each independently a hydrogen atom, an alkyl group, or an aryl group, together with a pharmaceutically acceptable excipient, diluent, or carrier.

In at least one embodiment, in an aspect, the pharmaceutical formulation can be a pro-drug pharmaceutical formulation, wherein the compound having formula (I) is in vivo hydrolyzed to form a compound having chemical formula (VI):

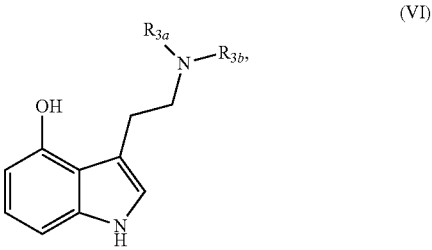

(VI)

wherein $R_{3a}$ and $R_{3b}$ are each independently a hydrogen atom, an alkyl group, or an aryl group.

In another aspect, the present disclosure relates to methods of treatment of brain neurological disorders. Accordingly, the present disclosure further provides, in one embodiment a method for treating a brain neurological disorder, the method comprising administering to a subject in need thereof a pharmaceutical formulation comprising a chemical compound having a formula (I):

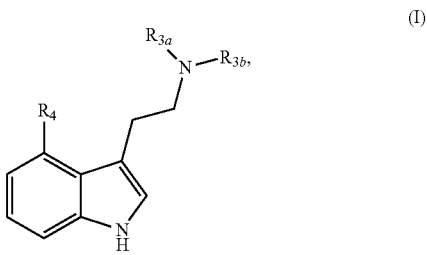

(I)

wherein $R_4$ is a carbonothioate moiety or derivative thereof; and wherein $R_{3a}$ and $R_{3b}$ are each independently a hydrogen atom, an alkyl group, or an aryl group, wherein the pharmaceutical formulation is administered in an effective amount to treat the brain neurological disorder in the subject.

In at least one embodiment, in an aspect, upon administration the compound having formula (I) can interact with a receptor in the subject to thereby modulate the receptor and exert a pharmacological effect.

In at least one embodiment, in an aspect, the receptor can be a $5\text{-HT}_{1A}$ receptor, a $5\text{-HT}_{2A}$ receptor, a $5\text{-HT}_{1B}$ receptor, a $5\text{-HT}_{2B}$ receptor, a $5\text{-HT}_{3A}$ receptor, an ADRA1A receptor, an ADRA2A receptor, a CHRM1 receptor, a CHRM2 receptor, a CNR1 receptor, a DRD1 receptor, a DRD2S receptor, an OPRD1 receptor, a GABAA receptor, or a NMDAR receptor.

In at least one embodiment, in an aspect, upon administration the compound having formula (I) can interact with a transmembrane transport protein in the subject to thereby modulate the transmembrane transport protein and exert a pharmacological effect.

In at least one embodiment, in an aspect, the transmembrane transport protein can be a dopamine active transporter (DAT), a norephedrine transporter (NET), or a serotonin transporter (SERT) transmembrane transport protein.

In at least one embodiment, in an aspect, upon administration the compound having formula (I) can be in vivo hydrolyzed to form a compound having chemical formula (VI):

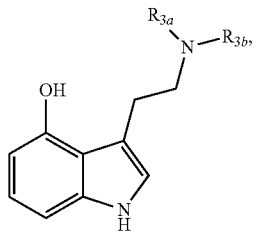
(VI)

wherein $R_{3a}$ and $R_{3b}$ are each independently a hydrogen atom, an alkyl group, or an aryl group, and wherein the compound having chemical formula (VI) interacts with a receptor to thereby modulate the receptor in the subject and exert a pharmacological effect.

In at least one embodiment, in an aspect, the receptor can be a 5-$HT_{1A}$ receptor, a 5-$HT_{2A}$ receptor, a 5-$HT_{1B}$ receptor, a 5-$HT_{2B}$ receptor, a 5-$HT_{3A}$ receptor, an ADRA1A receptor, an ADRA2A receptor, a CHRM1 receptor, a CHRM2 receptor, a CNR1 receptor, a DRD1 receptor, a DRD2S receptor, an OPRD1 receptor, a GABAA receptor, or a NMDAR receptor.

In at least one embodiment, in an aspect, the disorder can be a 5-$HT_{1A}$ receptor-mediated disorder, a 5-$HT_{2A}$ receptor-mediated disorder, a 5-$HT_{1B}$ receptor-mediated disorder, a 5-$HT_{2B}$ receptor-mediated disorder, a 5-$HT_{3A}$ receptor-mediated disorder, an ADRA1A receptor-mediated disorder, an ADRA2A receptor-mediated disorder, a CHRM1 receptor-mediated disorder, a CHRM2 receptor-mediated disorder, a CNR1 receptor-mediated disorder, a DRD1 receptor-mediated disorder, a DRD2S receptor-mediated disorder, an OPRD1 receptor-mediated disorder, a GABAA receptor-mediated disorder, or a NMDAR receptor-mediated disorder.

In at least one embodiment, in an aspect, a dose can be administered of about 0.001 mg to about 5,000 mg.

In another aspect, the present disclosure provides, in at least one embodiment, a method for modulating (i) a receptor selected from 5-$HT_{1A}$ receptor, a 5-$HT_{2A}$ receptor, a 5-$HT_{1B}$ receptor, a 5-$HT_{2B}$ receptor, a 5-$HT_{3A}$ receptor, an ADRA1A receptor, an ADRA2A receptor, a CHRM1 receptor, a CHRM2 receptor, a CNR1 receptor, a DRD1 receptor, a DRD2S receptor, an OPRD1 receptor, a GABAA receptor, or a NMDAR receptor; or (ii) a transmembrane transport protein selected from a dopamine active transporter (DAT), a norephedrine transporter (NET) or a serotonin transporter (SERT) transmembrane transport protein, the method comprising contacting (i) the 5-$HT_{1A}$ receptor, the 5-$HT_{2A}$ receptor, the 5-$HT_{1B}$ receptor, the 5-$HT_{2B}$ receptor, the 5-$HT_{3A}$ receptor, the ADRA1A receptor, the ADRA2A receptor, the CHRM1 receptor, the CHRM2 receptor, the CNR1 receptor, the DRD1 receptor, the DRD2S receptor, the OPRD1 receptor, the GABAA receptor, or the NMDAR receptor; or (ii) the dopamine active transporter (DAT), the norephedrine transporter (NET) or the serotonin transporter (SERT) transmembrane transport protein with a chemical compound having a formula (I):

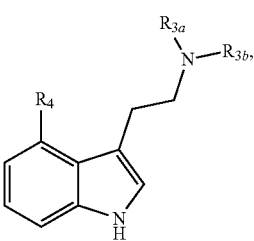
(I)

wherein $R_4$ is a carbonothioate moiety or derivative thereof; and wherein $R_{3a}$ and $R_{3b}$ are each independently a hydrogen atom, an alkyl group, or an aryl group, under reaction conditions sufficient to modulate the (i) the 5-$HT_{1A}$ receptor, the 5-$HT_{2A}$ receptor, the 5-$HT_{1B}$ receptor, the 5-$HT_{2B}$ receptor, the 5-$HT_{3A}$ receptor, the ADRA1A receptor, the ADRA2A receptor, the CHRM1 receptor, the CHRM2 receptor, the CNR1 receptor, the DRD1 receptor, the DRD2S receptor, the OPRD1 receptor, the GABAA receptor, or the NMDAR receptor; or (ii) the dopamine active transporter (DAT), the norephedrine transporter (NET) or the serotonin transporter (SERT) transmembrane transport protein.

In at least one embodiment, in an aspect, the reaction conditions can be in vitro reaction conditions.

In at least one embodiment, in an aspect, the reaction conditions can be in vivo reaction conditions.

In another aspect, the present disclosure relates to methods of making $C_4$-carbonothioate-substituted tryptamine derivative compounds. Accordingly, disclosed herein is, in one aspect, a method of making a chemical compound having chemical formula (VI):

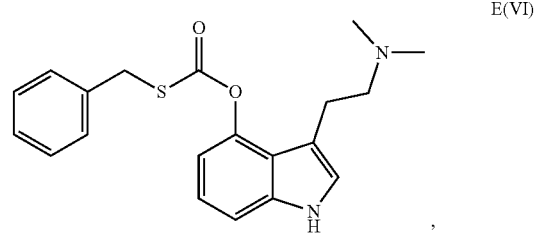 [SMILES: CN(C)CCc1c[nH]c2cccc(OC(=O)SCc3ccccc3)c12]
E(VI)

wherein the method involves the performance of one of the chemical reactions selected from (h) and (l):

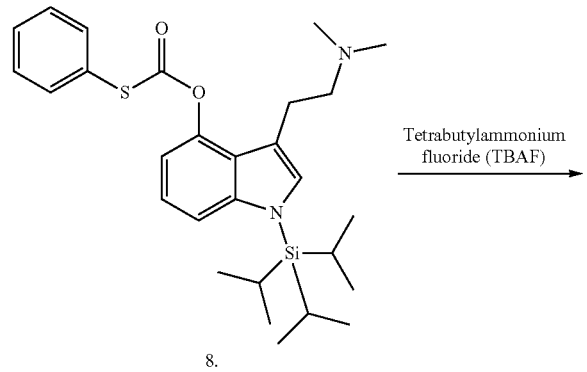
(h)

Tetrabutylammonium fluoride (TBAF)

8.

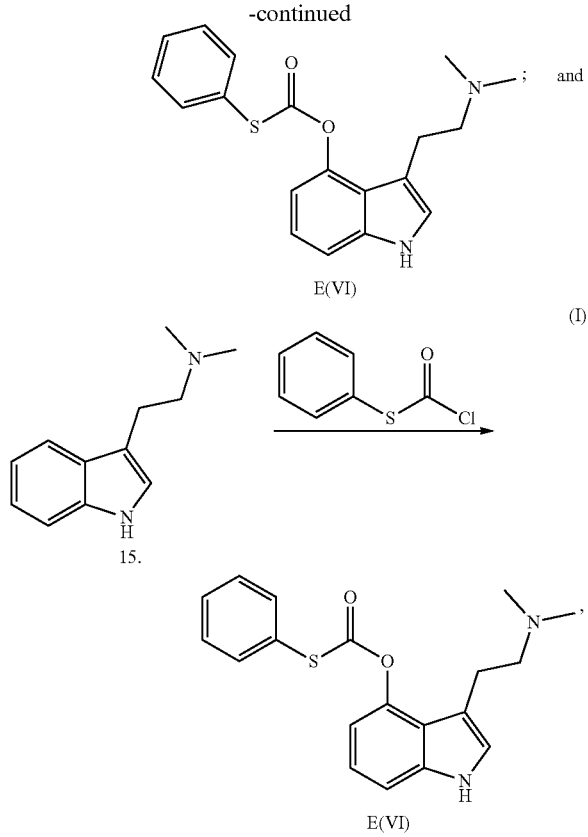

under reaction conditions sufficient to convert compound 8 or compound 15 to form E(VI).

In at least one embodiment, in an aspect, the method can involve the performance of chemical reaction (h), and preceding the performance of chemical reaction h, the performance of one of:

(i) chemical reaction (g);
(ii) each of chemical reaction (f) and (g) in consecutive order;
(iii) each of chemical reaction (e), (f), and (g) in consecutive order;
(iv) each of chemical reaction (d), (e), (f), and (g) in consecutive order;
(v) each of chemical reaction (c), (d), (e), (f), and (g) in consecutive order;
(vi) each of chemical reaction (b), (c), (d), (e), (f), and (g) in consecutive order; or
(vii) each of chemical reaction (a), (b), (c), (d), (e), (f), and (g) in consecutive order, wherein chemical reactions (a), (b), (c), (d), (e), (f), and (g) are the chemical reactions identified in FIGS. 3A (i), and 3A (ii), as (a), (b), (c), (d), (e), (f), and (g), respectively, and wherein each of the chemical reactions is performed under conditions sufficient to form E(VI).

In at least one embodiment, in an aspect, the method can involve the performance of chemical reaction (l), and preceding the performance of chemical reaction (l), the performance of one of:

(i) chemical reaction (k);
(ii) each of chemical reaction (j) and (k) in consecutive order; or
(iii) each of chemical reaction (i), (j), and (k) in consecutive order; and, optionally, preceding the performance of chemical reaction (l):
(iv) chemical reaction (m), wherein chemical reactions (i), (j), (k), and (m) are the chemical reactions identified in FIG. 3A (iii), as (i), (j), (k), and (m), respectively, and wherein each of the chemical reactions is performed under conditions sufficient to form E(VI).

In another aspect, the present disclosure relates to uses of $C_4$-carbonothioate-substituted tryptamine derivative compounds. Accordingly, the present disclosure further provides, in at least one embodiment, a use of a chemical compound having a formula (I):

(I)

wherein $R_4$ is a carbonothioate moiety or derivative thereof; and wherein $R_{3a}$ and $R_{3b}$ are each independently a hydrogen atom, an alkyl group, or an aryl group, in the manufacture of a pharmaceutical or recreational drug formulation.

In at least one embodiment, the manufacture can comprise formulating the chemical compound with a pharmaceutically acceptable excipient, diluent, or carrier.

In another aspect the present disclosure provides, in at least one embodiment, a use of a chemical compound having a formula (I):

(I)

wherein $R_4$ is a carbonothioate moiety or derivative thereof; and wherein $R_{3a}$ and $R_{3b}$ are each independently a hydrogen atom, an alkyl group, or an aryl group, together with a pharmaceutically acceptable diluent, carrier, or excipient as a pharmaceutical or recreational drug formulation.

In at least one embodiment, in aspect, the pharmaceutical drug is a drug for the treatment of a brain neurological disorder.

Other features and advantages will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described, by way of example, in relation to the attached figures. The figures provided herein are provided for a better understanding of the example embodiments and to show more clearly how the various embodiments may be carried into effect. The figures are not intended to limit the present disclosure.

Figure 1:
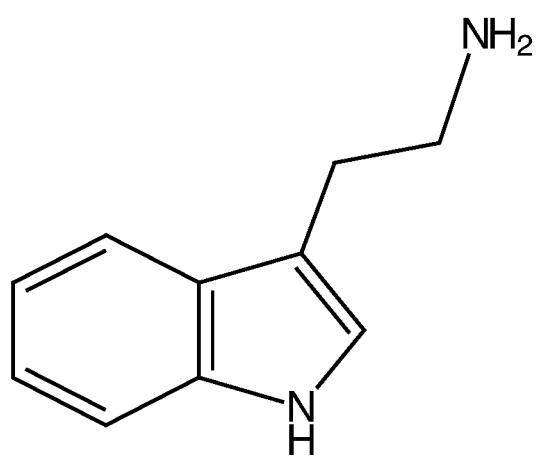
FIG. 1 depicts the chemical structure of tryptamine.

The figures together with the following detailed description make apparent to those skilled in the art how the disclosure may be implemented in practice.

DETAILED DESCRIPTION

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system, or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

As used herein and in the claims, the singular forms, such "a", "an" and "the" include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers.

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system, or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as modified in all instances by the term "about." The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by context. Furthermore, any range of values described herein is intended to specifically include the limiting values of the range, and any intermediate value or sub-range within the given range, and all such intermediate values and sub-ranges are individually and specifically disclosed (e.g., a range of 1 to 5 includes 1, 1.5, 2, 2.75, 3, 3.90, 4, and 5). Similarly, other terms of degree such as "substantially" and "approximately" as used herein mean a reasonable amount of deviation of the modified term such that the end result is not significantly changed. These terms of degree should be construed as including a deviation of the modified term if this deviation would not negate the meaning of the term it modifies.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

All publications, patents and patent applications are herein incorporated by reference in their entirety to the same extent as if each individual publication, patent, or patent application was specifically and individually indicated to be incorporated by reference in its entirety.

Terms and Definitions

The term "tryptamine" refers to a chemical compound having the structure set forth in FIG. 1.

Figure 2:
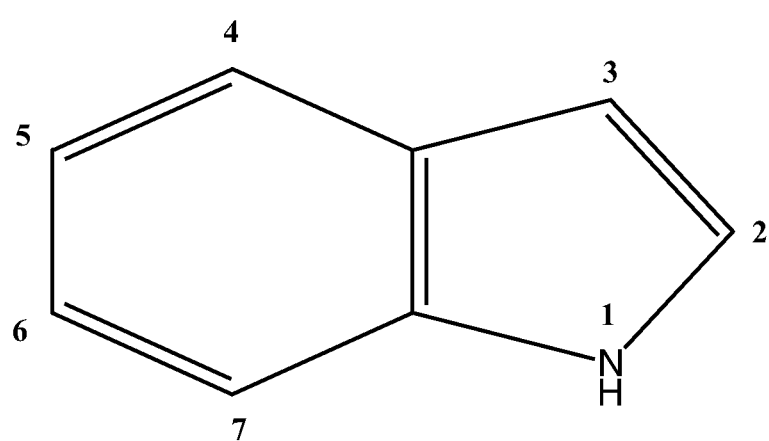
FIG. 2 depicts a certain prototype structure of tryptamine and tryptamine derivative compounds, namely an indole. Certain carbon and nitrogen atoms may be referred to herein by reference to their position within the indole structure, i.e., $N_1$, $C_2$, $C_3$ etc. The pertinent atom numbering is shown.

The term "indole prototype structure" refers to the chemical structure shown in FIG. 2. It is noted that specific carbon atoms and a nitrogen atom in the indole prototype structure are numbered. Reference may be made to these carbon and nitrogen numbers herein, for example $C_2$, $C_4$, $N_1$, and so forth. Furthermore, reference may be made to chemical groups attached to the indole prototype structure in accordance with the same numbering, for example, $R_4$ and $R_6$ reference chemical groups attached to the $C_4$ and $C_6$ atom, respectively. In addition, $R_{3a}$ and $R_{3b}$, in this respect, reference chemical groups extending from the ethyl-amino group extending in turn from the $C_3$ atom of the prototype indole structure.

The term "tryptamine derivative", as used herein, refers to compounds that can be derivatized from tryptamine, wherein such compounds include an indole prototype structure and a $C_3$ ethylamine or ethylamine derivative group having the formula (VII):

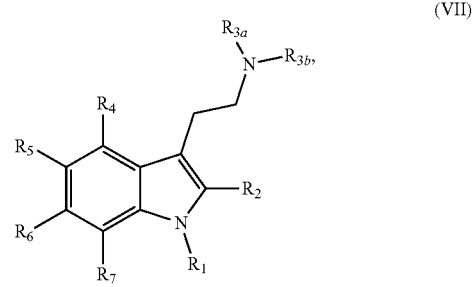

(VII)

wherein $R_4$, is a substituent (any atom or group other than a hydrogen atom) comprising a carbonothioate moiety or derivative thereto, and wherein $R_{3a}$ and $R_{3b}$ are each independently a hydrogen atom, an alkyl group, or an aryl group. Thus, tryptamine derivative compounds include compounds containing a substituent at $C_4$, as defined. Additional other atoms, such as $N_1$, may also be substituted. Moreover, in this respect, tryptamine derivatives containing a substituent atom or group at e.g., $C_4$ may be referred to as $C_4$-substituted tryptamine derivatives. In chemical formula (VII), $R_4$, can, for example, be a carbonothioate moiety or derivative thereof, and the tryptamine derivative may be referred to as a $C_4$-carbonothioate-substituted tryptamine derivative.

The term "carbonothioate moiety or derivative thereof", as used herein, refers to a derivative including a group having chemical formula $(XII)_a$ or $(XII)_b$:

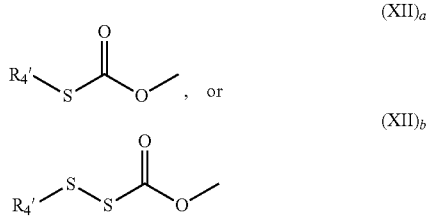

$(XII)_a$ $(XII)_b$

Wherein $R_4'$ is a hydrocarbon group, for example, an alkyl group, cyclo-alkyl group, or an aryl group. It is noted that the partially bonded oxygen atom of the group having formula $(XII)_a$ and $(XII)_b$ can be bonded to another entity, including, for example, to the $C_4$ atom of tryptamine. It is further noted that $R_4'$ can herein additionally include numerical subscripts, such as $_{4a}$, $_{4b}$, $_{4c}$, $_{4d}$ etc., and be represented, for example, as $R_{4a}$, $R_{4b}$, $R_{4c}$ or $R_{4d}$, respectively. Where such numerical values are included, they reference a chemical entity extending from the carboxyl group extending in turn from the thus numbered C atom of the prototype indole structure. Thus, for example, $R_{4c}$ is a chemical entity extending from a carbonothioate group attached to the $C_4$ atom of the indole ring structure.

The terms "halogen", "halogenated" and "halo-", as used herein, refer to the class of chemical elements consisting of fluorine (F), chlorine (Cl), bromine (Br), and iodine (I).

Accordingly, halogenated compounds can refer to "fluorinated", "chlorinated", "brominated", or "iodinated" compounds.

The terms "hydroxy group", and "hydroxy", as used herein refers to a molecule containing one atom of oxygen bonded to one atom of hydrogen and having the formula —OH. A hydroxy group through its oxygen atom may be chemically bonded to another entity.

The term "alkyl group", as used herein, refers to a straight and/or branched chain, saturated alkyl radical containing from one to "p" carbon atoms ("$C_1$-$C_p$-alkyl"; for example, p can be an integer between 2 and 20, for example, 3, 6, 10 or 20) and includes, depending on the identity of "p", methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl, and the like, where the variable p is an integer representing the largest number of carbon atoms in the alkyl radical. Alkyl groups further include hydrocarbon groups arranged in a chain having the chemical formula —$C_nH_{2n+1}$, including, without limitation, methyl groups (—$CH_3$), ethyl groups (—$C_2H_5$), propyl groups (—$C_3H_7$), and butyl groups (—$C_4H_9$).

The term "alkylene" refers to a divalent group derived from an alkane by removal of two hydrogen atoms from the same carbon atom. Examples of alkylenes include, without limitation, ethylene (—$C_2H_4$)—), propylene (—$C_3H_6$)—), and butylene (—$C_4H_8$)—). For the purposes of the present application further understood to be an alkylene is methylene (—$CH_2$—).

The term "cyclo-alkyl" refers to cyclo-alkyl groups, including ($C_3$-$C_{20}$), ($C_3$-$C_{10}$), and ($C_3$-$C_6$) cyclo-alkyl groups, and includes saturated and partially saturated cyclo-alkyl groups, further including cyclo-propane, cyclo-butane, cyclo-pentane, cyclo-hexane, cyclo-heptane, cyclopentene and cyclohexene.

The term "O-alkyl group", as used herein, refers to a hydrocarbon group arranged in a chain having the chemical formula —O—$C_nH_{2n+1}$. O-alkyl groups include, without limitation, O-methyl groups (—O—$CH_3$), O-ethyl groups (—O—$C_2H_5$), O-propyl groups (—O—$C_3H_7$) and O-butyl groups (—O—$C_4H_9$).

The term "aryl group", as used herein, refers to a hydrocarbon group arranged in an aromatic ring and can, for example, be a $C_6$-$C_{14}$-aryl, a $C_6$-$C_{10}$-aryl. Aryl groups further include phenyl, naphthyl, tetrahydronaphthyl, phenanthrenyl, biphenylenyl, indanyl, tolyl, xylyl, or indenyl groups, and the like.

The term "alcohol group" or "hydroxylalkyl", as used herein, refers to a hydrocarbon group arranged in a chain having the chemical formula $C_nH_{n+1}OH$. Depending on the carbon chain, length specific alcohol groups may be termed a methanol group (n=1) or hydroxymethyl, an ethanol group (n=2) or hydroxyethyl, a propanol group (n=3) or hydroxypropyl, a butanol group (n=4) or hydroxybutyl etc.

The term "receptor", as used herein, refers to a protein present on the surface of a cell, or in a cell not associated with a cellular surface (e.g., a soluble receptor) capable of mediating signaling to and/or from the cell, or within the cell and thereby affect cellular physiology. Example receptors include, 5-$HT_{1A}$ receptors, 5-$HT_{1B}$ receptors, 5-$HT_{2A}$ receptors, and "5-$HT_{2B}$ receptors", and so on. In this respect, "signaling" refers to a response in the form of a series of chemical reactions which can occur when a molecule, including, for example, the $C_4$-substituted tryptamine derivatives disclosed herein, interacts with a receptor. Signaling generally proceeds across a cellular membrane and/or within a cell, to reach a target molecule or chemical reaction, and results in a modulation in cellular physiology. Thus, signaling can be thought of as a transduction process by which a molecule interacting with a receptor can modulate cellular physiology, and, furthermore, signaling can be a process by which molecules inside a cell can be modulated by molecules outside a cell. Signaling and interactions between molecules and receptors, including for example, affinity, binding efficiency, and kinetics, can be evaluated through a variety of assays, including, for example, assays known as receptor binding assays (for example, radioligand binding assays, such as e.g., [$^3$H]ketanserin assays may be used to evaluate receptor 5-$HT_{2A}$ receptor activity), competition assays, and saturation binding assays, and the like.

The term "5-$HT_{1A}$ receptor", as used herein, refers to a subclass of a family of receptors for the neurotransmitter and peripheral signal mediator serotonin. 5-$HT_{1A}$ receptors can mediate a plurality of central and peripheral physiologic functions of serotonin. Ligand activity at 5-$HT_{1A}$ is generally not associated with hallucination, although many hallucinogenic compounds are known to modulate 5-$HT_{1A}$ receptors to impart complex physiological responses (Inserra et al., 2020, Pharmacol. Rev 73: 202). 5-$HT_{1A}$ receptors are implicated in various brain neurological disorders, including depression and anxiety, schizophrenia, and Parkinson's disease (Behav. Pharm. 2015, 26:45-58).

The term "5-$HT_{1B}$ receptor", as used herein, refers to a subclass of a family of receptors for the neurotransmitter and peripheral signal mediator serotonin. 5-$HT_{1B}$ receptors can mediate a plurality of central and peripheral physiologic functions of serotonin. Ligand activity at 5-$HT_{1B}$ is generally not associated with hallucination, although many hallucinogenic compounds are known to modulate 5-$HT_{1A}$ receptors to impart complex physiological responses (Inserra et al., 2020, Pharmacol. Rev. 73: 202). 5-$HT_{1B}$ receptors are implicated in various brain neurological disorders, including depression (Curr. Pharm. Des. 2018, 24:2541-2548).

The term "5-$HT_{2A}$ receptor", as used herein, refers to a subclass of a family of receptors for the neurotransmitter and peripheral signal mediator serotonin. 5-$HT_{2A}$ receptors can mediate a plurality of central and peripheral physiologic functions of serotonin. Central nervous system effects can include mediation of hallucinogenic effects of hallucinogenic compounds. 5-$HT_{2A}$ receptors are implicated in various brain neurological disorders (Nat. Rev. Drug Discov. 2022, 21:463-473; Science 2022, 375:403-411).

The term "5-$HT_{2B}$ receptor", as used herein, refers to a subclass of a family of receptors for the neurotransmitter and peripheral signal mediator serotonin. 5-$HT_{2B}$ receptors can mediate a plurality of central and peripheral physiologic functions of serotonin. Central nervous system effects can include mediation of hallucinogenic effects of hallucinogenic compounds. 5-$HT_{bA}$ receptors are implicated in various brain neurological disorders, including schizophrenia (Pharmacol. Ther. 2018, 181:143-155) and migraine (Cephalalgia 2017, 37:365-371).

The term "5-$HT_{3A}$ receptor", as used herein, refers to a subclass of a family of receptors for the neurotransmitter and peripheral signal mediator serotonin. 5-$HT_{3A}$ receptors can mediate a plurality of central and peripheral physiologic functions of serotonin. 5-$HT_{3A}$ receptors are implicated in various brain neurological disorders, including depression (Expert Rev. Neurother. 2016, 16:483-95).

The term "ADRA1A receptor", as used herein, refers to a subclass of a family of receptors, also known as α1-adrenergic receptors, which can be modulated by selective serotonin reuptake inhibitors (SSRIs) and tricyclic antidepressant (TCA) (Int. J. Mol Sci. 2021, 22: 4817; Brain Res. 1285 2009, 148-157). ADRA1A receptors are implicated in various brain neurological disorders, including depression.

The term "ADRA2A receptor", as used herein, refers to a subclass of a family of receptors, also known as α2-adrenergic receptors. ADRA2A receptors are implicated in various brain neurological disorders, including Attention Deficit Hyperactivity Disorder (ADHD) (J. Am. Acad. Child. Adolesc. Psychiatry 2014, 53:153-73), mania, bipolar disorder, and schizophrenia.

The term "CHRM1 receptor", as used herein, refers to a subclass of receptors also known as "cholinergic receptor muscarinic 1", which can be modulated by selective serotonin reuptake inhibitors (SSRIs) (e.g., paroxetine) and tricyclic antidepressant (TCA). The class of CHRM receptors are implicated in various brain neurological disorders, including depression, major depression disorder (MDD), and bipolar disorder (Mol. Psychiatry 2019, 24: 694-709).

The term "CHRM2 receptor", as used herein, refers to a subclass of receptors also known as "cholinergic receptor muscarinic 2", which can be modulated by tricyclic antidepressant (TCA). The class of CHRM receptors are implicated in various brain neurological disorders, including depression, major depression disorder (MDD), and bipolar disorder (Mol. Psychiatry 2019, 24: 694-709).

The term "CNR1 receptor", as used herein, refers to a subclass of receptors also known as "cannabinoid receptor $CB_1$", which can be modulated by cannabinoid compounds. CNR receptors are implicated in various brain neurological disorders, including depression and schizophrenia (Pharmacol. Res. 2021, 170: 105729).

The term "DRD1 receptor", as used herein, refers to a subclass of receptors also known as "dopamine receptor $D_1$", which can be modulated by dopamine. Dopamine receptors are implicated in various brain neurological disorders, including schizophrenia, psychosis, and depression (Neurosci. Lett. 2019, 691:26-34).

The term "DRD2S receptor", as used herein, refers to a subclass of receptors also known as "dopamine receptor $D_2S$", which can be modulated by dopamine. Dopamine receptors are implicated in various brain neurological disorders, including schizophrenia, psychosis, and depression (Neurosci. Lett. 2019, 691:26-34).

The term "OPRD1 receptor", as used herein, refers to a subclass of receptors also known as "opioid receptor $D_1$", which can be modulated by opioid compounds. OPRD1 receptors are implicated in various brain neurological disorders, including psychopathy, and substance abused disorder (Mol. Psychiatry 2020, 25:3432-3441).

The term "GABAA receptor", as used herein, refers to a subclass of receptors also known as "γ-aminobutyric acid (GABA) receptor A", which can be modulated by γ-aminobutyric acid. GABAA receptors are implicated in various brain neurological disorders, including anxiety, major depressive disorder, and post-partum depression (Trends Pharmacol. Sci. 2018, 39:710-732).

The term "NMDAR receptor", as used herein, refers to a subclass of receptors also known as "N-methyl-D-aspartate receptor". NMDAR receptors are glutamatergic receptors that are implicated in various brain neurological disorders, including epilepsy, autism spectrum disorder, and schizophrenia (Transl. Psychiatry 2022, 12:243).

The term "DAT", as used herein, refers to a transmembrane transport protein also known as "dopamine active transporter", which is involved of transporting dopamine into the cytosol. DAT is implicated in various brain neurological disorders, notably dopamine related disorders such as attention deficit hyperactivity disorder (ADHD), bipolar disorder, and clinical depression, anxiety (Am. J. Med. Genet. B Neuropsychiatr. Genet. 2018, 177:211-231).

The term "NET", as used herein, refers to a transmembrane transport protein also known as "norepinephrine transporter" or "noradrenaline transporter" or "NAT" which is involved in $Na^+/Cl^-$ dependent re-uptake of extracellular norepinephrine or noradrenaline. NET is implicated in various brain neurological disorders, including attention deficit hyperactivity disorder (ADHD) and clinical depression (Neurosci. Biobehav. Rev, 2013, 37:1786-800).

The term "SERT", as used herein, refers to a transmembrane transport protein also known as "serotonin transporter" which is involved in neuronal serotonin transport, notably from the synaptic cleft back to the presynaptic neuron, thereby terminating the action of serotonin. SERT is implicated in various brain neurological disorders, including anxiety and depression (Pharmacol. Rep. 2018, 70:37-46).

The term "modulating receptors", as used herein, refers to the ability of a compound disclosed herein to alter the function of receptors. A receptor modulator may activate the activity of a receptor, or inhibit the activity of a receptor depending on the concentration of the compound exposed to the receptor. Such activation or inhibition may be contingent on the occurrence of a specific event, such as activation of a signal transduction pathway, and/or maybe manifest only in particular cell types. The term "modulating receptors," also refers to altering the function of a receptor by increasing or decreasing the probability that a complex forms between a receptor and a natural binding partner to form a multimer. A receptor modulator may increase the probability that such a complex forms between the receptor and the natural binding partner, may increase or decrease the probability that a complex forms between the receptor and the natural binding partner depending on the concentration of the compound exposed to the receptor, and or may decrease the probability that a complex forms between the receptor and the natural binding partner. It is further noted that the $C_4$-carbonothioate-substituted tryptamine derivatives of the present disclosure may alter the function of a receptor by acting as an agonist or antagonist of the receptor, and that $C_4$-carbonothioate-substituted tryptamine derivatives according to the present disclosure may alter the function of a receptor by directly interacting therewith or binding thereto, or by indirectly interacting therewith through one or more other molecular entities. In general, the receptor may be any receptor, including any receptor set forth herein, such as any of a $5-HT_{1A}$, $5-HT_{1B}$, $5-HT_{2A}$, and a $5-HT_{2B}$ receptor, for example. Accordingly, it will be clear, that in order to refer modulating specific receptors, terms such as "modulating $5-HT_{1A}$ receptors", "modulating $5-HT_{1B}$ receptors", "modulating $5-HT_{2A}$ receptors", "modulating $5-HT_{2B}$ receptors", and so forth, may be used herein.

The term "receptor-mediated disorder", as used herein, refers to a disorder that is characterized by abnormal receptor activity. A receptor-mediated disorder may be completely or partially mediated by modulating a receptor. In particular, a receptor-mediated disorder is one in which modulation of the receptor results in some effect on an underlying disorder e.g., administration of a receptor modulator results in some improvement in at least some of the subjects being treated. In general, the receptor may be any receptor, including any receptor set forth herein, such as any of a $5-HT_{1A}$, $5-HT_{1B}$, $5-HT_{2A}$, and a $5-HT_{2B}$ receptor, for example. Accordingly, it will be clear, that in order to refer specific receptor-mediated disorders, terms such as "$5-HT_{1A}$ receptor-mediated disorder", "$5-HT_{1B}$ receptor-mediated disorder", "$5-HT_{2A}$ receptor-mediated disorder", "5-HT$_{2B}$ receptor-mediated disorder", and so forth, may be used.

The term "pharmaceutical formulation", as used herein, refers to a preparation in a form which allows an active ingredient, including a psychoactive ingredient, contained therein to provide effective treatment, and which does not contain any other ingredients which cause excessive toxicity, an allergic response, irritation, or other adverse response commensurate with a reasonable risk/benefit ratio. The pharmaceutical formulation may contain other pharmaceutical ingredients such as excipients, carriers, diluents, or auxiliary agents.

The term "recreational drug formulation", as used herein, refers to a preparation in a form which allows a psychoactive ingredient contained therein to be effective for administration as a recreational drug, and which does not contain any other ingredients which cause excessive toxicity, an allergic response, irritation, or other adverse response commensurate with a reasonable risk/benefit ratio. The recreational drug formulation may contain other ingredients such as excipients, carriers, diluents, or auxiliary agents.

The term "effective for administration as a recreational drug", as used herein, refers to a preparation in a form which allows a subject to voluntarily induce a psychoactive effect for non-medical purposes upon administration, generally in the form of self-administration. The effect may include an altered state of consciousness, satisfaction, pleasure, euphoria, perceptual distortion, or hallucination.

The term "effective amount", as used herein, refers to an amount of an active agent, pharmaceutical formulation, or recreational drug formulation, sufficient to induce a desired biological or therapeutic effect, including a prophylactic effect, and further including a psychoactive effect. Such effect can include an effect with respect to the signs, symptoms or causes of a disorder, or disease or any other desired alteration of a biological system. The effective amount can vary depending, for example, on the health condition, injury stage, disorder stage, or disease stage, weight, or sex of a subject being treated, timing of the administration, manner of the administration, age of the subject, and the like, all of which can be determined by those of skill in the art.

The terms "treating" and "treatment", and the like, as used herein, are intended to mean obtaining a desirable physiological, pharmacological, or biological effect, and includes prophylactic and therapeutic treatment. The effect may result in the inhibition, attenuation, amelioration, or reversal of a sign, symptom or cause of a disorder, or disease, attributable to the disorder, or disease, which includes mental and psychiatric diseases and disorders. Clinical evidence of the prevention or treatment may vary with the disorder, or disease, the subject, and the selected treatment.

The term "pharmaceutically acceptable", as used herein, refers to materials, including excipients, carriers, diluents, or auxiliary agents, that are compatible with other materials in a pharmaceutical or recreational drug formulation and within the scope of reasonable medical judgement suitable for use in contact with a subject without excessive toxicity, allergic response, irritation, or other adverse response commensurate with a reasonable risk/benefit ratio.

The terms "substantially pure" and "isolated", as may be used interchangeably herein describe a compound, e.g., a $C_4$-carbonothioate-substituted tryptamine derivative, which has been separated from components that naturally or synthetically accompany it. Typically, a compound is substantially pure when at least 60%, more preferably at least 75%, more preferably at least 90%, 95%, 96%, 97%, or 98%, and most preferably at least 99% of the total material (by volume, by wet or dry weight, or by mole percent or mole fraction) in a sample is the compound of interest. Purity can be measured by any appropriate method, e.g., by chromatography, gel electrophoresis or HPLC analysis.

General Implementation

As hereinbefore mentioned, the present disclosure relates to tryptamine derivatives. in particular, the present disclosure provides novel $c_4$-substituted tryptamine derivatives, and in particular to $C_4$-carbonothioate substituted tryptamine derivatives. In general, the herein provided compositions exhibit functional properties which deviate from the functional properties o tryptamine. thus, for example, the $C_4$-carbonothioate-substituted tryptamine derivatives can exhibit pharmacological properties which deviate from tryptamine. Furthermore, the $C_4$-carbonothioate-substituted tryptamine derivatives may exhibit physico-chemical properties which differ from tryptamine. Thus, for example, $C_4$-carbonothioate-substituted tryptamine derivatives may exhibit superior solubility in a solvent, for example, an aqueous solvent. Furthermore, the $C_4$-carbonothioate-substituted tryptamine derivatives may exhibit pharmacokinetics or pharmacodynamics which are different from a non-substituted compound. The $C_4$-carbonothioate-substituted tryptamine derivatives in this respect are useful in the formulation of pharmaceutical and recreational drug formulations.

In what follows selected embodiments are described with reference to the drawings.

Accordingly, in one aspect, the present disclosure provides derivatives of a compound known as tryptamine of which the chemical structure is shown in FIG. 1. The derivatives herein provided are, in particular, $C_4$-substituted tryptamine derivatives, i.e., derivatives, wherein the $C_4$ atom is bonded to a substituent group, notably a carbonothioate moiety or derivative thereof.

Thus, in one aspect, the present disclosure provides, in accordance with the teachings herein, in at least one embodiment, a compound having chemical formula (I):

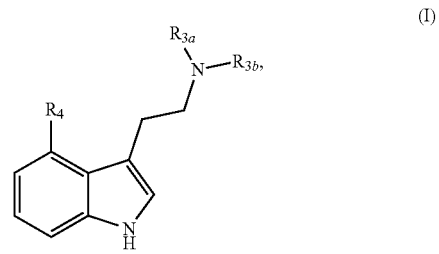

wherein $R_4$ is a carbonothioate moiety or derivative thereof; and wherein $R_{3a}$ and $R_{3b}$ are each independently a hydrogen atom, an alkyl group, or an aryl group.

Thus, referring to the chemical compound having the formula (i), in an aspect hereof, $R_4$ can be a carbonothioate moiety or derivative thereof, i.e., a carbonothioate moiety or derivative which is bonded via its oxygen atom to the $C_4$ atom of the tryptamine compound.

In some embodiments, in an aspect, the carbonothioate moiety or derivative thereof can have the chemical formula (III):

(III)

$$R_{4b}\text{—S—C(=O)—O—}\overset{}{\underset{}{\text{CH}}}$$

wherein $R_{4b}$ is an alkyl group, a cyclo-alkyl group, or an aryl group, each of which are optionally substituted.

In some embodiments, the carbonothioate moiety or derivative thereof can have the chemical formula (IV):

(IV)

$$R_{4c}\text{—S—S—C(=O)—O—}\overset{}{\underset{}{\text{CH}}}$$

wherein $R_{4c}$ is an alkyl group, a cyclo-alkyl group, or an aryl group, each of which are optionally substituted.

In some embodiments, in the compound having chemical formula (III), $R_{4b}$ can be $C_1$-$C_6$ alkyl optionally substituted with a halogen atom (chloro, fluoro, bromo iodo), alkyl group (for example, $C_1$-$C_{10}$ alkyl or $C_1$-$C_6$ alkyl or $C_1$-$C_3$ alkyl), cycloalkyl group (for example, $C_3$-$C_{10}$ cycloalkyl or $C_3$-$C_6$ cycloalkyl), or an aryl group, a phenyl group, for example.

In some embodiments, in the compound having chemical formula (III), $R_{4b}$ can be $C_1$-$C_3$ alkyl (i.e., a $C_1$-$C_3$ alkylene (e.g., methylene, ethylene, propylene), optionally substituted with a halogen atom (chloro, fluoro, bromo, iodo), alkyl group, cycloalkyl group, or an aryl group, a phenyl group, for example.

In some embodiments, in the compound having chemical formula (III) $R_{4b}$ can be methyl, ethyl, isopropyl, butyl, —$CH_2$-cyclopropyl, —$CH(CH_3)$-cyclopropyl, —$C(CH_3)_2$-cyclopropyl or —$CH_2$-phenyl.

In some embodiments, $R_{4b}$ can be an aryl group, a phenyl group, for example.

In some embodiments, in the compound having chemical formula (III), $R_{4b}$ can be $C_1$-$C_6$ alkyl optionally substituted with a halogen atom (chloro, fluoro, bromo, iodo), alkyl group, cycloalkyl group, or aryl group, and wherein one or more of the carbon atoms in the $C_1$-$C_6$ alkyl group are replaced with oxygen (O) atoms.

In some embodiments, in the compound having chemical formula (IV), $R_{4c}$ can be $C_1$-$C_6$ alkyl optionally substituted with a halogen atom (chloro, fluoro, bromo, iodo), alkyl group (for example, $C_1$-$C_{10}$ alkyl or $C_1$-$C_6$ alkyl or $C_1$-$C_3$ alkyl), cycloalkyl group (for example, $C_3$-$C_{10}$ cycloalkyl or $C_3$-$C_6$ cycloalkyl), or aryl group, a phenyl group for example.

In some embodiments, in the compound having chemical formula (IV) $R_{4c}$ can be methyl, ethyl, isopropyl, butyl, —$CH_2$-cyclopropyl, —$CH(CH_3)$-cyclopropyl, —$C(CH_3)_2$-cyclopropyl or —$CH_2$-phenyl.

In some embodiments, in the compound having chemical formula (IV) $R_{4c}$ can be an aryl group, a phenyl group for example.

In some embodiments, in the compound having chemical formula (IV, $R_{4c}$ can be $C_1$-$C_6$ alkyl optionally substituted with a halogen atom (chloro, fluoro, bromo, iodo), alkyl group, cycloalkyl group, or aryl group, and wherein one or more of the carbon atoms in the $C_1$-$C_6$ alkyl group are replaced with oxygen (O) atoms.

In an aspect, the present disclosure provides a compound having chemical formula (I) wherein $R_4$ is a carbonothioate moiety or derivative thereof, the compound having the chemical formula E(I):

E(I)

[Structure of E(I): 4-position of indole bears O—C(=O)—S—CH₃; 3-position bears —CH₂CH₂—N(CH₃)₂]

In an aspect, the present disclosure provides a compound having chemical formula (I) wherein $R_4$ is a carbonothioate moiety or derivative thereof, the compound having the chemical formula E(II):

E(II)

[Structure of E(II): 4-position of indole bears O—C(=O)—S—CH₂CH₃; 3-position bears —CH₂CH₂—N(CH₃)₂]

In an aspect, the present disclosure provides a compound having chemical formula (I) wherein $R_4$ is a carbonothioate moiety or derivative thereof, the compound having the chemical formula E(III):

E(III)

[Structure of E(III): 4-position of indole bears O—C(=O)—S—CH(CH₃)₂; 3-position bears —CH₂CH₂—N(CH₃)₂]

In an aspect, the present disclosure provides a compound having chemical formula (I) wherein $R_4$ is a carbonothioate moiety or derivative thereof, the compound having the chemical formula E(IV):

E(IV)

[Structure of E(IV): 4-position of indole bears O—C(=O)—S—CH₂CH₂CH₂CH₃; 3-position bears —CH₂CH₂—N(CH₃)₂]

In an aspect, the present disclosure provides a compound having chemical formula (I) wherein $R_4$ is a carbonothioate moiety or derivative thereof, the compound having the chemical formula E(V):

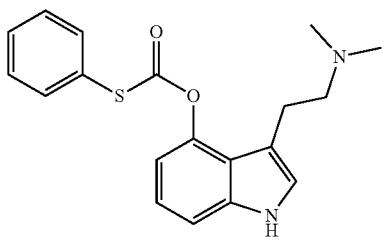

E(V)

In some embodiments, in an aspect, in the compound having chemical formula (I) wherein $R_4$ is a carbonothioate moiety or derivative thereof, the compound having the chemical formula E(VI):

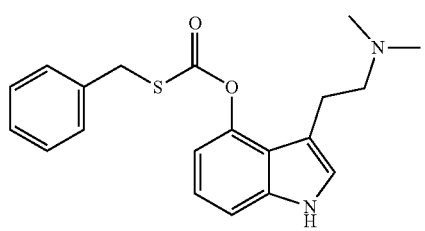

E(VI)

In an aspect, the present disclosure provides a compound having chemical formula (I) wherein $R_4$ is a carbonothioate moiety or derivative thereof, the compound having the chemical formula E(VII):

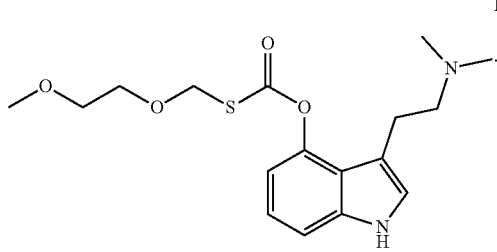

E(VII)

In an aspect, the present disclosure provides a compound having chemical formula (I) wherein $R_4$ is a carbonothioate moiety or derivative thereof, the compound having the chemical formula E(VIII):

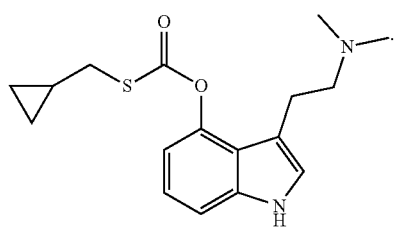

E(VIII)

In an aspect, the present disclosure provides a compound having chemical formula (I) wherein $R_4$ is a carbonothioate moiety or derivative thereof, the compound having the chemical formula E(IX):

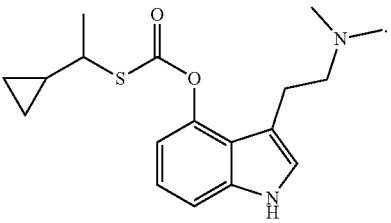

E(IX)

In an aspect, the present disclosure provides a compound having chemical formula (I) wherein $R_4$ is a carbonothioate moiety or derivative thereof, the compound having the chemical formula E(X):

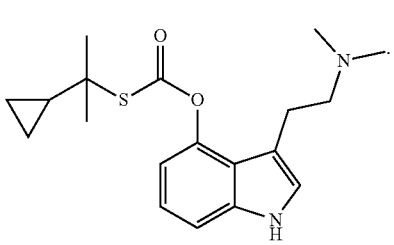

E(X)

In an aspect, the present disclosure provides a compound having chemical formula (I) wherein $R_4$ is a carbonothioate moiety or derivative thereof, the compound having the chemical formula E(XI):

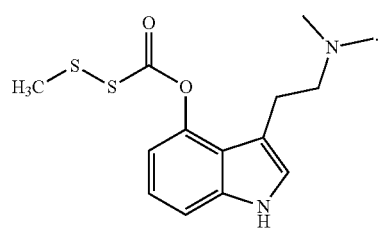

E(XI)

In an aspect, the present disclosure provides a compound having chemical formula (I) wherein $R_4$ is a carbonothioate moiety or derivative thereof, the compound having the chemical formula E(XII):

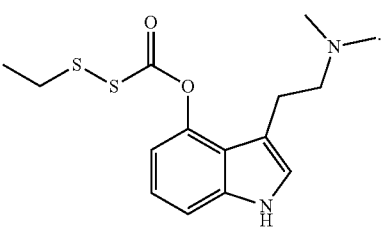

E(XII)

In an aspect, the present disclosure provides a compound having chemical formula (I) wherein $R_4$ is a carbonothioate moiety or derivative thereof, the compound having the chemical formula E(XIII):

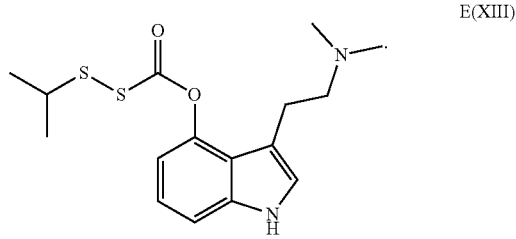 [SMILES: CC(C)SSC(=O)Oc1cccc2[nH]cc(CCN(C)C)c12]

E(XIII)

In an aspect, the present disclosure provides a compound having chemical formula (I) wherein $R_4$ is a carbonothioate moiety or derivative thereof, the compound having the chemical formula E(XIV):

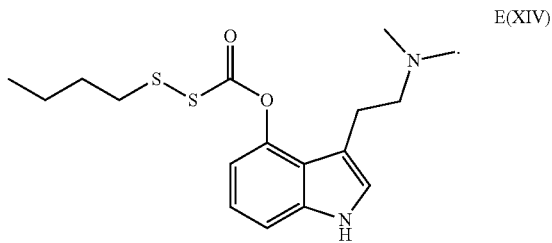 [SMILES: CCCCSSC(=O)Oc1cccc2[nH]cc(CCN(C)C)c12]

E(XIV)

In an aspect, the present disclosure provides a compound having chemical formula (I) wherein $R_4$ is a carbonothioate moiety or derivative thereof, the compound having the chemical formula E(XV):

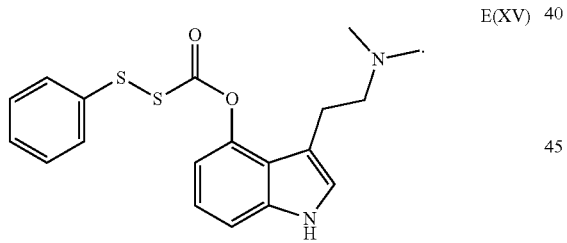

E(XV)

In some embodiments, in an aspect, in the compound having chemical formula (I) wherein $R_4$ is a carbonothioate moiety or derivative thereof, the compound having the chemical formula E(XVI):

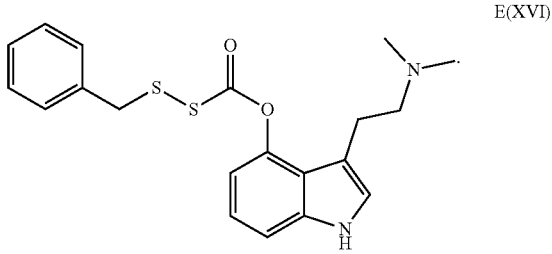 [SMILES: CN(C)CCc1c[nH]c2cccc(OC(=O)SSCc3ccccc3)c12]

E(XVI)

In an aspect, the present disclosure provides a compound having chemical formula (I) wherein $R_4$ is a carbonothioate moiety or derivative thereof, the compound having the chemical formula E(XVII):

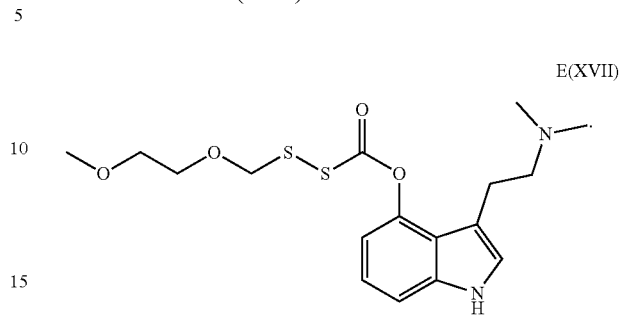

E(XVII)

In an aspect, the present disclosure provides a compound having chemical formula (I) wherein $R_4$ is a carbonothioate moiety or derivative thereof, the compound having the chemical formula E(XVIII):

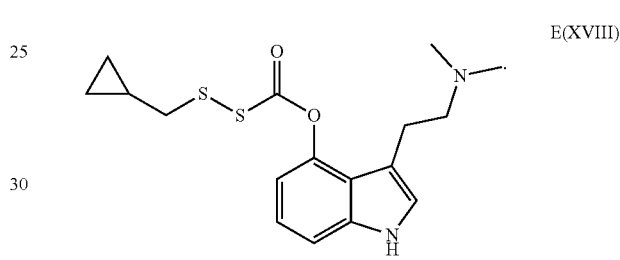

E(XVIII)

In an aspect, the present disclosure provides a compound having chemical formula (I) wherein $R_4$ is a carbonothioate moiety or derivative thereof, the compound having the chemical formula E(XIX):

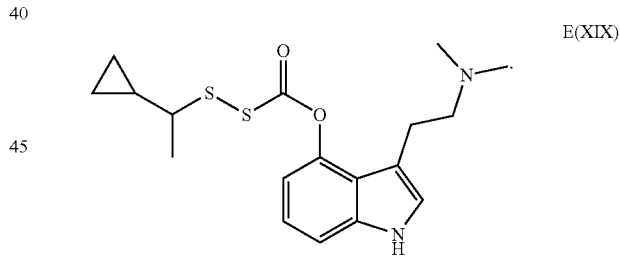

E(XIX)

In an aspect, the present disclosure provides a compound having chemical formula (I) wherein $R_4$ is a carbonothioate moiety or derivative thereof, the compound having the chemical formula E(XX):

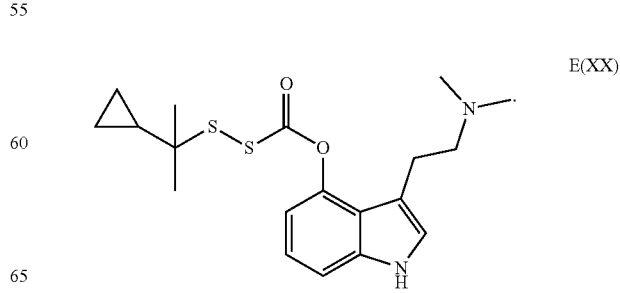

E(XX)

Referring further to the compound having chemical formula (I), $R_{3a}$ and $R_{3b}$ can be independently a hydrogen atom or a $(C_1-C_{20})$-alkyl group or an aryl group, for example a phenyl group. In another embodiment, $R_{3a}$ and $R_{3b}$ are independently a hydrogen atom or a $(C_1-C_{10})$-alkyl group or an aryl group, for example a phenyl group. In another embodiment, $R_{3a}$ and $R_{3b}$ are independently a hydrogen atom or a $(C_1-C_6)$-alkyl group or an aryl group, for example a phenyl group. In another embodiment, $R_{3a}$ and $R_{3b}$ are independently a hydrogen atom, a methyl group, an ethyl group, or a propyl group, or an aryl group, for example a phenyl group.

Thus, to briefly recap, the present disclosure provides $C_4$-carbonothioate-substituted tryptamine derivatives. The disclosure provides, in particular, a chemical compound having a formula (I):

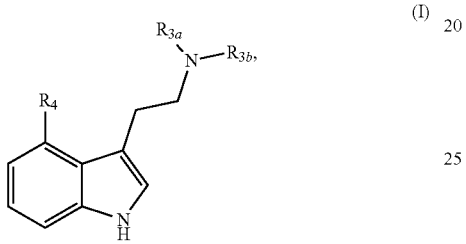

(I)

wherein $R_4$ is a carbonothioate moiety or derivative thereof; and wherein $R_{3a}$ and $R_{3b}$ are each independently a hydrogen atom, an alkyl group, or an aryl group.

The foregoing provides $C_4$-carbonothioate-substituted tryptamine including a $C_4$-carbonothioate-substituted tryptamine wherein the carbonothioate moiety or derivative thereof can have the chemical formula (III):

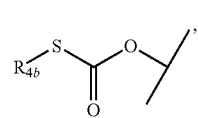

(III)

wherein $R_{4b}$ is an alkyl group, a cyclo-alkyl group, or an aryl group, each of which are optionally substituted; and further including a $C_4$-carbonothioate-substituted tryptamine wherein the carbonothioate moiety or derivative thereof can have the chemical formula (IV):

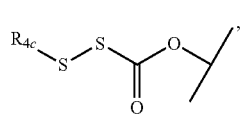

(IV)

wherein $R_{4c}$ is an alkyl group, a cyclo-alkyl group, or an aryl group, each of which are optionally substituted.

In another embodiment, $R_{3a}$ and $R_{3b}$ are independently a hydrogen atom or a $(C_1-C_{20})$-alkyl group or an aryl group, for example a phenyl group. In another embodiment, $R_{3a}$ and $R_{3b}$ are independently a hydrogen atom or a $(C_1-C_{10})$-alkyl group or an aryl group, for example a phenyl group. In another embodiment, $R_{3a}$ and $R_{3b}$ are independently a hydrogen atom or a $(C_1-C_6)$-alkyl group or an aryl group, for example, a phenyl group. In another embodiment, $R_{3a}$ and $R_{3b}$ are independently a hydrogen atom, a methyl group, an ethyl group, or a propyl group, or an aryl group, for example a phenyl group.

The $C_4$-carbonothioate-substituted tryptamine derivatives of the present disclosure may be used to prepare a pharmaceutical or recreational drug formulation. thus, in one embodiment, the present disclosure further provides in another aspect, pharmaceutical and recreational drug formulations comprising $C_4$-carbonothioate-substituted tryptamine derivatives. accordingly, in one aspect, the present disclosure provides in a further embodiment a pharmaceutical or recreational drug formulation comprising a chemical compound having a formula (i):

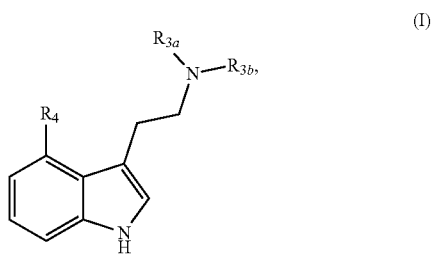

(I)

wherein $R_4$ is a carbonothioate moiety or derivative thereof; and wherein $R_{3a}$ and $R_{3b}$ are each independently a hydrogen atom, an alkyl group, or an aryl group.

The pharmaceutical or recreational drug formulations may be prepared as liquids, tablets, capsules, microcapsules, nanocapsules, trans-dermal patches, gels, foams, oils, aerosols, nanoparticulates, powders, creams, emulsions, micellar systems, films, sprays, ovules, infusions, teas, decoctions, suppositories, etc. and include a pharmaceutically acceptable salt or solvate of the $C_4$-substituted tryptamine derivative compound together with an excipient. The term "excipient" as used herein means any ingredient other than the chemical compound of the disclosure. In order to prepare a pharmaceutical drug formulation in accordance herewith, the $C_4$-carbonothioate-substituted tryptamine derivative compounds are generally initially prepared and obtained in a substantially pure form, most preferably, at least in a 98%, 99% or 99.9% pure form, and thereafter formulated with a pharmaceutically acceptable excipient. As will readily be appreciated by those of skill in art, the selection of excipient may depend on factors such as the particular mode of administration, the effect of the excipient on solubility of the chemical compounds of the present disclosure and methods for their preparation will be readily apparent to those skilled in the art. Such compositions and methods for their preparation may be found, for example, in "Remington's Pharmaceutical Sciences", $22^{nd}$ Edition (Pharmaceutical Press and Philadelphia College of Pharmacy at the University of the Sciences, 2012).

The dose when using the compounds of the present disclosure can vary within wide limits, and as is customary and is known to those of skill in the art, the dose can be tailored to the individual conditions in each individual case. The dose depends, for example, on the nature and severity of the illness to be treated, on the condition of the patient, on the compound employed or on whether an acute or chronic disease state is treated, or prophylaxis is conducted, on the mode of delivery of the compound, or on whether further active compounds are administered in addition to the compounds of the present disclosure. Representative doses of the present invention include, but are not limited to, about 0.001 mg to about 5000 mg, about 0.001 mg to about 2500 mg, about 0.001 mg to about 1000 mg, about 0.001 mg to about 500 mg, about 0.001 mg to about 250 mg, about 0.001 mg to about 100 mg, about 0.001 mg to about 50 mg, and about 0.001 mg to about 25 mg. Representative doses of the present disclosure include, but are not limited to, about 0.0001 to about 1,000 mg, about 10 to about 160 mg, about 10 mg, about 20 mg, about 40 mg, about 80 mg or about 160 mg. Multiple doses may be administered during the day, especially when relatively large amounts are deemed to be needed, for example 2, 3 or 4, doses. Depending on the subject and as deemed appropriate from the patient's physician or care giver it may be necessary to deviate upward or downward from the doses described herein.

The pharmaceutical and drug formulations comprising the $C_4$-carbonothioate-substituted tryptamine derivative compounds of the present disclosure may be administered orally. Oral administration may involve swallowing, so that the compound enters the gastrointestinal tract, or buccal or sublingual administration may be employed by which the compound enters the blood stream directly from the mouth. Formulations suitable for oral administration include both solid and liquid formulations.

Solid formulations include tablets, capsules (containing particulates, liquids, microcapsules, or powders), lozenges (including liquid-filled lozenges), chews, multi- and nano-particulates, gels, solid solutions, liposomal preparations, microencapsulated preparations, creams, films, ovules, suppositories, and sprays.

Liquid formulations include suspensions, solutions, syrups, and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose.

Tablets may also contain diluents, such as lactose (monohydrate, spray-dried monohydrate, anhydrous and the like), mannitol, xylitol, dextrose, sucrose, sorbitol, microcrystalline cellulose, starch, and dibasic calcium phosphate dihydrate.

Tablets may also optionally comprise surface active agents, such as sodium lauryl sulfate and polysorbate 80. When present, surface active agents may comprise from 0.2% (w/w) to 5% (w/w) of the tablet.

Tablets may further contain lubricants such as magnesium stearate, calcium stearate, zinc stearate, sodium stearyl fumarate, and mixtures of magnesium stearate with sodium lauryl sulphate. Lubricants generally comprise from 0.25% (w/w) to 10% (w/w), from 0.5% (w/w) to 3% (w/w) of the tablet.

in addition to the $C_4$-carbonothioate-substituted tryptamine derivative compounds, tablets may contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1% (w/w) to 25% (w/w) or from 5% (w/w) to 20% (w/w) of the dosage form.

Other possible auxiliary ingredients include anti-oxidants, colourants, flavouring agents, preservatives, and taste-masking agents.

For tablet dosage forms, depending on the desired effective amount of the chemical compound, the chemical compound of the present disclosure may make up from 1% (w/w) to 80% (w/w) of the dosage form, more typically from 5% (w/w) to 60% (w/w) of the dosage form.

Exemplary tablets contain up to about 80% (w/w) of the chemical compound, from about 10% (w/w) to about 90% (w/w) binder, from about 0% (w/w) to about 85% (w/w) diluent, from about 2% (w/w) to about 10% (w/w) disintegrant, and from about 0.25% (w/w) to about 10% (w/w) lubricant.

The formulation of tablets is discussed in "Pharmaceutical Dosage Forms: Tablets", Vol. 1-Vol. 3, by CRC Press (2008).

The pharmaceutical and recreational drug formulations comprising the $C_4$-carbonothioate-substituted tryptamine derivative compound of the present disclosure may also be administered directly into the blood stream, into muscle, or into an internal organ. Thus, the pharmaceutical and recreational drug formulations can be administered parenterally (for example, by subcutaneous, intravenous, intraarterial, intrathecal, intraventricular, intracranial, intramuscular, or intraperitoneal injection). Parenteral formulations are typically aqueous solutions which may contain excipients such as salts, carbohydrates, and buffering agents (in one embodiment, to a pH of from 3 to 9), but, for some applications, they may be more suitably formulated as a sterile non-aqueous solution or as a dried form to be used in conjunction with a suitable vehicle such as sterile water.

Formulations comprising the $C_4$-carbonothioate-substituted tryptamine derivative compound of the present disclosure for parenteral administration may be formulated to be immediate and/or modified release. Modified release formulations include delayed-, sustained-, pulsed-, controlled-, targeted and programmed release. Thus, the chemical compounds of the disclosure may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The pharmaceutical or recreational drug formulations of the present disclosure also may be administered topically to the skin or mucosa, i.e., dermally or transdermally. Example pharmaceutical and recreational drug formulations for this purpose include gels, hydrogels, lotions, solutions, creams, ointments, dusting powders, cosmetics, oils, eye drops, dressings, foams, films, skin patches, wafers, implants, sponges, fibres, bandages and microemulsions. Liposomes may also be used. Example carriers include alcohol, water, mineral oil, liquid petrolatum, white petrolatum, glycerin, polyethylene glycol and propylene glycol. Penetration enhancers may be incorporate (see: for example, Finnin, B. and Morgan, T. M., 1999 J. Pharm. Sci, 88 (10), 955-958).

Other means of topical administration include delivery by electroporation, iontophoresis, phonophoresis, sonophoresis and microneedle or needle-free (e.g., Powderject™, Bioject™, etc.) injection.

Pharmaceutical and recreational drug formulations for inhalation or insufflation include solutions and suspensions in pharmaceutically acceptable, aqueous, or organic solvents, or mixtures thereof, and powders. The liquid or solid pharmaceutical compositions can contain suitable pharmaceutically acceptable excipients. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device, or the nebulizing device can be attached to a face mask tent, or intermittent positive pressure breathing machine. Solution, suspension, or powder pharmaceutical compositions can be administered, e.g., orally, or nasally, from devices that deliver the formulation in an appropriate manner.

It is noted that in some embodiments, the chemical compounds in the pharmaceutical formulation may act as pro-drugs. Pro-drugs represent a modality to control drug bioavailability, control timing of drug release, and/or reduce negative side-effects. Similarly, formulation and delivery considerations can achieve these outcomes. Thus, optimization of all three variables together (prodrug moiety, formulation, delivery system) can be an effective strategy in drug development. Examples of 'targeting systems' designed to specifically reach cells within the brain, obtained by simultaneously leveraging pro-drug, nanoparticle. And nasal administration strategies are described, for example by Botti et al., 2021 Pharmaceutics 13:1114).

In further embodiments, in which the $C_4$-carbonothioate-substituted tryptamine derivative compounds of present disclosure are used as a recreational drug, the compounds may be included in compositions such as a food or food product, a beverage, a food seasoning, a personal care product, such as a cosmetic, perfume or bath oil, or oils (both for topical administration as massage oil, or to be burned or aerosolized). The chemical compounds of the present disclosure may also be included in a "vape" product, which may also include other drugs, such as nicotine, and flavorings.

Thus, it will be clear that the $C_4$-carbonothioate-substituted tryptamine derivative compounds may be used as a pharmaceutical or recreational drug. Accordingly, in another aspect the present disclosure provides, in at least one embodiment, a use of a chemical compound having a formula (I):

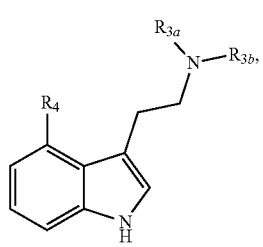

(I)

wherein $R_4$ is a carbonothioate moiety or derivative thereof; and
wherein $R_{3a}$ and $R_{3b}$ are each independently a hydrogen atom, an alkyl group, or an aryl group, as a pharmaceutical or recreational drug The pharmaceutical formulations comprising the chemical compounds of the present disclosure may be used to treat a subject, and to treat a brain neurological disorder in a subject. Accordingly, the present disclosure includes in a further embodiment, a method for treating a brain neurological disorder, the method comprising administering to a subject in need thereof a pharmaceutical formulation comprising a chemical compound having a formula (I):

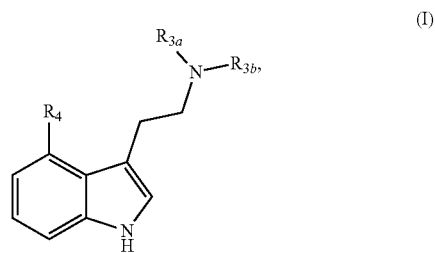

(I)

wherein $R_4$ is a carbonothioate moiety or derivative thereof; and
wherein $R_{3a}$ and $R_{3b}$ are each independently a hydrogen atom, an alkyl group, or an aryl group, wherein the pharmaceutical formulation is administered in an effective amount to treat the brain neurological disorder.

Brain neurological disorders include psychiatric disorders that may be treated include, for example, neurodevelopmental disorders such as intellectual disability, global development delay, communication disorders, autism spectrum disorder, and attention-deficit hyperactivity disorder (ADHD); bipolar and related disorders, such as mania, and depressive episodes; anxiety disorder, such as generalized anxiety disorder (GAD), agoraphobia, social anxiety disorder, specific phobias (natural events, medical, animal, situational, for example), panic disorder, and separation anxiety disorder; stress disorders, such as acute stress disorder, adjustment disorders, post-traumatic stress disorder (PTSD), and reactive attachment disorder; dissociative disorders, such as dissociative amnesia, dissociative identity disorder, and depersonalization/derealization disorder; somatoform disorders, such as somatic symptom disorders, illness anxiety disorder, conversion disorder, and factitious disorder; eating disorders, such as anorexia nervosa, bulimia nervosa, rumination disorder, pica, and binge-eating disorder; sleep disorders, such as narcolepsy, insomnia disorder, hypersomnolence, breathing-related sleep disorders, parasomnias, and restless legs syndrome; disruptive disorders, such as kleptomania, pyromania, intermittent explosive disorder, conduct disorder, and oppositional defiant disorder; depressive disorders, such as disruptive mood dysregulation disorder, major depressive disorder (MDD), persistent depressive disorder (dysthymia), premenstrual dysphoric disorder, substance/medication-induced depressive disorder, postpartum depression, and depressive disorder caused by another medical condition, for example, psychiatric and existential distress within life-threatening cancer situations (ACS Pharmacol. Transl. Sci. 4: 553-562; J. Psychiatr. Res 137: 273-282); substance-related disorders, such as alcohol-related disorders, *cannabis* related disorders, inhalant-use related disorders, stimulant use disorders, and tobacco use disorders; neurocognitive disorders, such as delirium; schizophrenia; compulsive disorders, such as obsessive compulsive disorders (OCD), body dysmorphic disorder, hoarding disorder, trichotillomania disorder, excoriation disorder, substance/medication induced obsessive-compulsive disorder, and obsessive-compulsive disorder related to another medical condition; and personality disorders, such as antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder. Brain neurological disorders further include headache disorders, including migraines, including, for example, aural migraine, non-aural migraine, menstrual migraine, chronic migraine, vestibular migraine, abdominal migraine, hemiplegic migraine, and other headache disorders.

In an aspect, the compounds of the present disclosure may be used to be contacted with a receptor to thereby modulate the receptor. Such contacting includes bringing a compound of the present disclosure and receptor together under in vitro conditions, for example, by introducing the compounds in a sample containing a receptor, for example, a sample containing purified receptors, or a sample containing cells comprising receptors. In vitro conditions further include the conditions described in Example 1 hereof. Contacting further includes bringing a compound of the present disclosure and receptor together under in vivo conditions. Such in vivo conditions include the administration to an animal or human subject, for example, of a pharmaceutically effective amount of the compound of the present disclosure, when the compound is formulated together with a pharmaceutically active carrier, diluent, or excipient, as hereinbefore described, to thereby treat the subject. Upon having contacted the 5 receptor, the compound may activate the receptor or inhibit the receptor.

In an aspect receptors with which the compounds of the present disclosure may be contacted include, for example, the 5-$HT_{1A}$ receptor, the 5-$HT_{2A}$ receptor, the 5-$HT_{1B}$ receptor, the 5-$HT_{2B}$ receptor, the 5-$HT_{3A}$ receptor, the ADRA1A receptor, the ADRA2A receptor, the CHRM1 receptor, the CHRM2 receptor, the CNR1 receptor, the DRD1 receptor, the DRD2S receptor, the OPRD1 receptor, the GABAA receptor, or the NMDAR receptor.

Thus, in a further aspect, the condition that may be treated in accordance herewith can be any receptor mediated disorder, including, for example, a 5-$HT_{1A}$ receptor-mediated disorder, a 5-$HT_{2A}$ receptor-mediated disorder, a 5-$HT_{1B}$ receptor-mediated disorder, a 5-$HT_{2B}$ receptor-mediated disorder, a 5-$HT_{3A}$ receptor-mediated disorder, a ADRA2A receptor-mediated disorder, a AVPR1A receptor-mediated disorder, a CHRM1 receptor-mediated disorder, a CHRM2 receptor-mediated disorder, a CNR1 receptor-mediated disorder, a DRD1 receptor-mediated disorder, a DRD2S receptor-mediated disorder, a OPRD1 receptor-mediated disorder, a GABAA receptor-mediated disorder, or a NMDAR receptor-mediated disorder. Such disorders include, but are not limited to schizophrenia, psychotic disorder, attention deficit hyperactivity disorder, autism, and bipolar disorder.

In some embodiments, upon having contacted a receptor and a receptor, the compound may modulate the receptor. However at the same time other receptors may not be modulated. e.g., a compound may activate or inhibit a first receptor, e.g., a 5-$HT_{1A}$ receptor, however the compound may at the same time not modulate a second receptor, e.g., a 5-$HT_{2A}$ receptor, or upon having contacted a first 5-$HT_{2A}$ receptor and a second 5-$HT_{1A}$ receptor, the compound may modulate the first 5-$HT_{2A}$ receptor, e.g., activate or inhibit the 5-$HT_{2A}$ receptor, however the compound may at the same time not modulate the second 5-$HT_{1A}$ receptor.

In one embodiment, in an aspect, upon administration the compounds of the present disclosure can interact with a transmembrane transport protein in the subject to thereby modulate the transmembrane transport protein and exert a pharmacological effect. Such contacting includes bringing a compound of the present disclosure and transmembrane protein together under in vitro conditions, for example, by introducing the compounds in a sample containing a transmembrane transport protein, for example, a sample containing a purified transmembrane transport protein, or a sample containing cells comprising a transmembrane transport protein. Contacting further includes bringing a compound of the present disclosure and a transmembrane transport protein together under in vivo conditions. Such in vivo conditions include the administration to an animal or human subject, for example, of a pharmaceutically effective amount of the compound of the present disclosure, when the compound is formulated together with a pharmaceutically active carrier, diluent, or excipient, as hereinbefore described, to thereby treat the subject.

In one embodiment, in an aspect, the transmembrane transport protein can be a dopamine active transporter (DAT), a norephedrine transporter (NET) or a serotonin transporter (SERT) transmembrane transport protein.

It is noted that in one embodiment, in an aspect, upon administration the compound having formula (I) may be in vivo hydrolyzed to form a compound having chemical formula (VI):

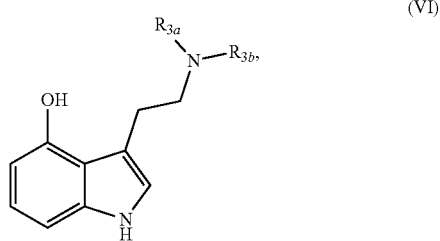

(VI)

wherein $R_{3a}$ and $R_{3b}$ are each independently a hydrogen atom, an alkyl group, or an aryl group, and wherein the compound having chemical formula (VI) interacts with a receptor to thereby modulate the receptor in the subject and exert a pharmacological effect. In this respect, the compounds of the present disclosure may be formulated as a pro-drug pharmaceutical formulation, i.e., a formulation wherein it is not the formulated compound itself that mediates a pharmacological effect, but rather a compound that is obtained following in vivo hydrolyzation of the formulated compound by the subject. Hydrolyzation may occur, for example, in the gastro-intestinal tract of a person upon oral delivery of a pro-drug pharmaceutical formulation.

Turning now to methods of making the $C_4$-carbonothioate-substituted tryptamine derivative compounds of the present disclosure, it is initially noted, by way of general comment that the $C_4$-carbonothioate-substituted tryptamine derivative compounds of the present disclosure may be prepared in any suitable manner, including by any organic chemical synthesis methods, biosynthetic methods, or a combination thereof.

Figure 3A:
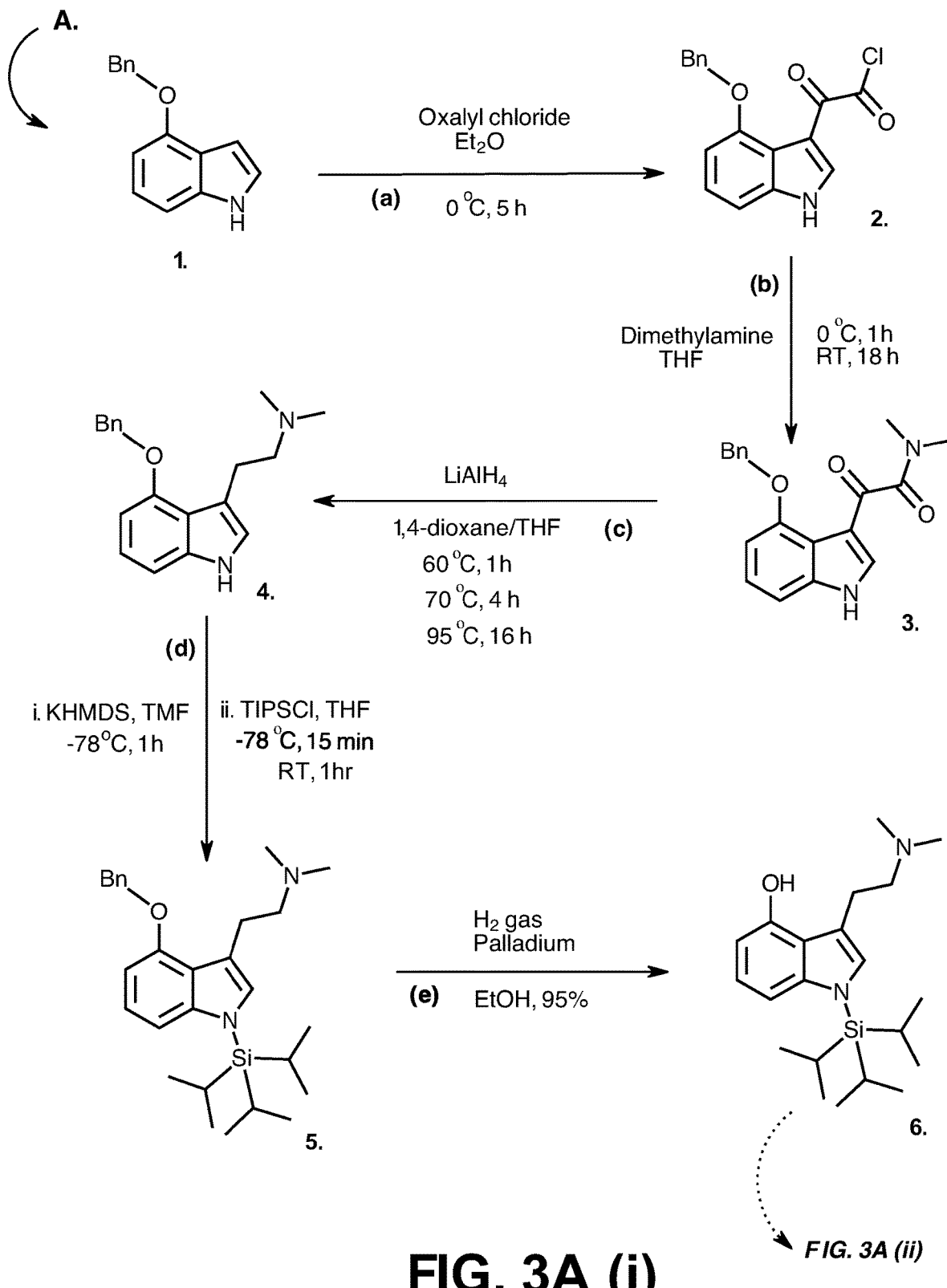
FIGS. 3A (i), 3A (ii), 3A (iii), 3B, 3C, 3D, 3E, 3F, 3G, 3H, 3I, 3J, 3K, 3L, 3M (i), 3M (ii), 3M (iii), 3N (i), 3N (ii), 3O (i), 3O (ii), 3P, 3Q, 3R, 3S (i) and 3S (ii) depict example chemical reactions to make an example chemical compound provided by the present disclosure, namely a compound having chemical formula E(VI) (FIGS. 3A (i) and 3A (ii) together depicting example synthesis pathway A, and FIG. 3A (iii) depicting example synthesis pathway B), and various graphs representing certain experimental results (FIGS. 3B-3S (ii)), notably, graphs obtained in the performance of experimental assays to evaluate the efficacy of an example compound having chemical formula E(VI), notably, a cell viability assay (FIGS. 3B, 3C) a saturation binding assay for [$^3$H]ketanserin at the 5-HT$_{2A}$ receptor (FIG. 3D); a competition assay for psilocin as a positive control (binding) (FIG. 3E); a competition assay for tryptophan as a negative control (no binding) (FIG. 3F); a competition assay for a compound with formula E(VI), designated "E-VI" (FIG. 3G); a cAMP assay in the presence of varying concentrations of the compound having chemical formula E(VI), designated "E-VI" in +5HT$_{1A}$ cells and −5HT$_{1A}$ cells, (FIG. 3H); a cAMP assay in the presence of varying concentrations of tryptophan in +5HT$_{1A}$ cells and −5HT$_{1A}$ cells with 4 µM forskolin (FIG. 3I); a cAMP assay in the presence of varying concentrations of psilocin in +5HT$_{1A}$ cells and −5HT$_{1A}$ cells stimulated with 4 µM forskolin (FIG. 3J); a cAMP assay in the presence of varying concentrations of serotonin in +5HT$_{1A}$ cells and −5HT$_{1A}$ cells stimulated with 4 µM forskolin (FIG. 3K); a cAMP assay in the presence of varying concentrations of the compound having chemical formula E(VI), designated "E-VI" in +5HT$_{1A}$ cells and −5HT$_{1A}$ cells with 4 µM forskolin (FIG. 3L); psilocybin metabolic conversion assays (FIGS. 3M (i)-3M (iii)); assay controls for psilocin metabolic release assays (FIGS. 3N (i)-3N (ii)); metabolic stability assays for a compound with formula E(VI) (FIGS. 3O (i)-3O (ii)); and drug-induced Head Twitch Response (HTR) assays using the compound having formula E(VI), designated "E-VI" (FIG. 3P); mouse PK studies analyzing plasma psilocybin levels after 1 mg/kg i.v. dose of psilocybin (FIG. 3Q); mouse PK studies analyzing plasma psilocin levels after oral dosing of various levels of psilocybin (FIG. 3R); and mouse PK studies using a chemical compound having formula E(VI) (FIGS. 3S (i) and 3S (ii)).

Examples of suitable chemical reactions that may be performed in accordance herewith are depicted in FIGS. 3A (i), 3A (ii), 3A (iii) and 4A (Panel I.), and are further additionally detailed hereinafter in the Example section.

In general, as is known to those of skill in the art, in order to perform chemical synthetic reactions selected reactants are reacted under reaction conditions suitable for the reactants to chemically react with each other and form a product, i.e., the $C_4$-carbonothioate-substituted tryptamine derivative compounds of the present disclosure. Such suitable reactions conditions may be selected, adjusted, and optimized as known by those of skill in the art. The reactions may be conducted in any suitable reaction vessel (e.g., a tube, bottle). Suitable solvents that may be used are polar solvents such as, for example, dichloromethane, dimethylformamide, dichloroethane, toluene, and so called participating solvents such as acetonitrile and diethyl ether. Suitable temperatures may range from, for example, e.g., from about −78° C. to about 60° C. Furthermore, catalysts, also known as promoters, may be included in the reaction such as iodonium dicollidine perchlorate (IDCP), any silver or mercury salts, trimethylsilyl trifluoromethanesulfonate (TMS-triflate, TMSOTf), or trifluoronmethanesulfonic acid (triflic acid, TfOH), N-iodosuccinimide, methyl triflate. Furthermore, reaction times may be varied. As will readily be appreciated by those of skill in the art, the reaction conditions may be optimized, for example, by preparing several reactant preparations and reacting these in separate reaction vessels under different reaction conditions, for example, different temperatures, using different solvents etc., evaluating the obtained $C_4$-carboxylic acid-substituted tryptamine derivative compounds product, adjusting reaction conditions, and selecting a desired reaction condition.

Referring to FIGS. 3A (i) and 3A (ii), in one embodiment, the compound having formula (I) can be a compound having formula E(VI):

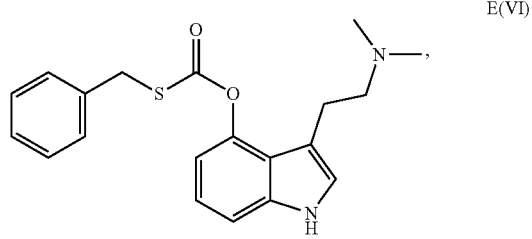 [SMILES: CN(C)CCc1c[nH]c2cccc(OC(=O)SCc3ccccc3)c12]

E(VI)

and the method of making the compound having formula E(VI) can involve the performance of chemical reaction (h):

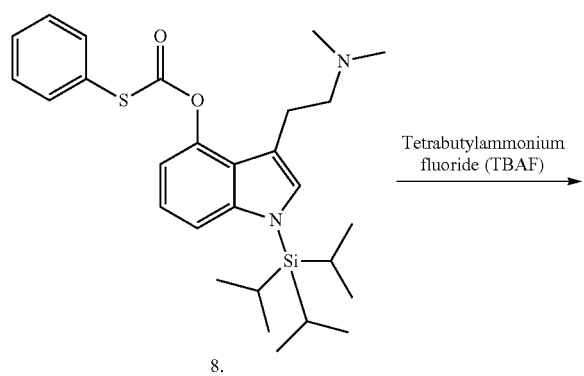

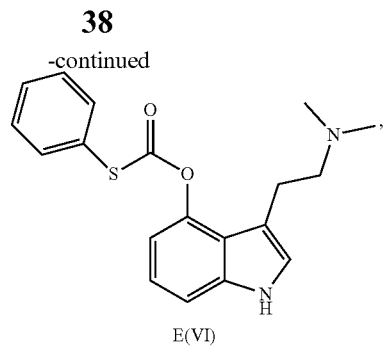

E(VI)

wherein the chemical reaction is performed under conditions suitable to convert compound 8 and form E(VI).

Suitable and sufficient reaction conditions for the performance of chemical reaction (h) include conducting reaction (h) in the presence of from about 0.1 M-1.5 M tetrabutylammonium fluoride (TBAF), including for example, about 0.75, 0.9 M, 1 M, 1.1 m or 1.25 M TBAF in tetrahydrofuran (THF). Thus, for example, TBAF, may be added dropwise at 0° C., and after 30 min, water can be added, and the aqueous layer can be separated and extracted with dichloromethane DCM to obtain E(VI).

Referring to FIG. 3A (ii), chemical reaction (h) can be said to be a final reaction to synthesize compound 9 (corresponding with compound E(VI)) from compound 8 in a chemical synthesis pathway A. Thus, referring further to FIG. 3A (ii), it will be clear that additional chemical reactions may performed to make compound E(VI). For example, additionally compound 7 may be selected to perform chemical reaction (g) depicted in FIG. 3A (ii) to synthesize compound 8, which in turn may be used to synthesize compound 9 by the performance of chemical reaction (h). Thus, by way of another example, compound 6 may be selected to perform chemical reaction (f) depicted in FIG. 3A (ii) to synthesize compound 7, which in turn may be used to synthesize compound 8 by the performance of chemical reaction (g), which in turn may be used to synthesize compound 9 by the performance of chemical reaction h. Thus, similarly, referring to FIG. 3A (i), any one of compounds 1, 2, 3, 4 or 5 may be selected, and one or more suitable chemical reactions may be selected from depicted reactions (a), (b), (c), (d), and (e), and performed to obtain chemical compound 6, which, as noted, may be used to synthesize compound 7, which in turn may be used to synthesize compound 8, which in turn may be used to synthesize compound 9.

Thus, in one example embodiment, preceding reaction (h), chemical reaction (g) can be performed (in the indicated consecutive (i.e., alphabetical) order).

In one example embodiment, preceding reaction (h), chemical reactions (f) and (g) can be sequentially performed (in the indicated consecutive (i.e., alphabetical) order).

In one example embodiment, preceding reaction (h), chemical reactions (e), (f), and (g) can be sequentially performed (in the indicated consecutive (i.e., alphabetical) order).

In one example embodiment, preceding reaction (h), chemical reactions (d), (e), (f), and (g) are sequentially performed (in the indicated consecutive (i.e., alphabetical) order).

In one example embodiment, preceding reaction (h), chemical reactions (c), (d), (e), (f), and (g) can be sequentially performed (in the indicated consecutive (i.e., alphabetical) order).

In one example embodiment, preceding reaction (h), chemical reactions (b), (c), (d), (e), (f), and (g) can be sequentially performed (in the indicated consecutive (i.e., alphabetical) order).

In one example embodiment, in preceding reaction (h), chemical reactions (a), (b), (c), (d), (e), (f), and (g) can be sequentially performed (in the indicated consecutive (i.e., alphabetical) order).

Referring next to FIG. 3A (iii), in one embodiment, the compound having formula (I) can be a compound having formula E(VI):

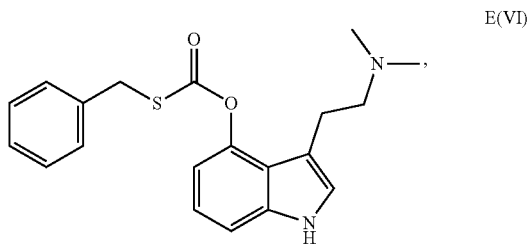 [SMILES: CN(C)CCc1c[nH]c2cccc(OC(=O)SCc3ccccc3)c12]

E(VI)

and the method of making the compound having formula E(VI) can involve the performance of chemical reaction (l):

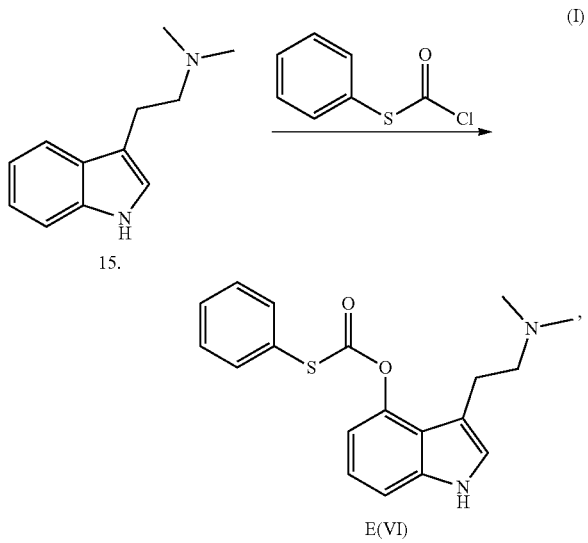

wherein the chemical reaction is performed under conditions suitable to convert compound 15 and form E(VI).

Suitable and sufficient reaction conditions for the performance of chemical reaction (l) include conducting reaction (l) by adding to solution of compound 15 and potassium carbonate in dimethyl formamide (DMF), a solution of benzylchlorothioformate in DMF, and reacting reactants 15 and benzylchlorothioformate, for example, at room temperature, for example for a period of at least 6 hours, e.g., for about 6 hours, 9 hours, 12 hours, 15, hours, 18, hours or 24 hours, to form E(VI).

Referring to FIG. 3A (iii), chemical reaction (l) is a final reaction to synthesize compound 9 (corresponding with compound E(VI)) from compound 15 in a chemical synthesis pathway B. Thus it will be clear that additional chemical reactions may performed to make compound E(VI). Thus, for example, additionally compound 14 may be selected to perform chemical reaction (k) depicted in FIG. 3A (iii) to synthesize compound 15, which in turn may be used to synthesize compound 9 by performing chemical reaction (l). Thus, by way of another example, compound 13 may be selected to perform chemical reaction (j) depicted in FIG. 3A (iii) to synthesize compound 14 by performing chemical reaction (k), which in turn may be used to synthesize compound 15, which in turn may be used to synthesize compound 9 by performing chemical reaction (l). Thus, similarly, referring to FIG. 3A (iii), it will be clear that compound 12 may be selected, and one or more suitable chemical reactions may be selected by referring to FIG. 3A (iii) and performed to obtain chemical compound 13, which, as noted, may be used to synthesize compound 14, which in turn may be used to synthesize compound 15, which in turn may be used to synthesize compound 9. It is noted that additionally compound 11 is used to perform the reaction to form compound 9 from compound 15. Compound 11 may optionally be synthesized from compound 10 in accordance with chemical reaction (m) depicted in FIG. 3A (iii).

Thus, in one example embodiment, preceding reaction (l), chemical reaction (k) is performed (in alphabetical order).

In one example embodiment, preceding reaction (l), chemical reactions (j) and (k) can be sequentially performed (in the indicated consecutive (i.e., alphabetical) order).

In one example embodiment, preceding reaction (l), chemical reactions (i), (j), and (k) can be sequentially performed (in the indicated consecutive (i.e., alphabetical) order).

In one example embodiment, optionally preceding chemical reaction (l), reaction (m) can be performed.

In some embodiments, the chemical compounds referred to herein, including, without limitation, the $C_4$-carbonothioate-substituted tryptamine derivatives having chemical formulas E(I), E(II), E(III), E(IV), E(V), E(VI), E(VII), E(VIII), E(IX), E(X), E(XI), E(XII), E(XIII), E(XIV), E(XV), E(XVI), E(XVII), E(XVIII), E(XIX), or E(XX), may be isolated in pure or substantially pure form. Thus the compounds referred to herein may be, for example, at least 90%, 95%, 96%, 97%, or 98%, or at least 99% pure.

It will now be clear from the foregoing that novel $C_4$-carbonothioate-substituted tryptamine derivatives are disclosed herein. the $C_4$-carbonothioate-substituted tryptamine derivatives may be formulated for use as a pharmaceutical drug or recreational drug. Example embodiments and implementations of the present disclosure are further illustrated by the following examples.

EXAMPLES

Example 1—Synthesis and Analysis of a First $C_4$-Carbonothioate-Substituted Tryptamine Derivative This Example 1 initially discusses example methods for the synthesis of an example compound disclosed herein, in particular, synthesis of an example $C_4$-carbonothioate substituted tryptamine having chemical formula E(VI) with reference to FIGS. 3A (i), 3A (ii) and FIG. 3A (iii). FIGS. 3A (i) and 3A (ii) together depict a first example synthesis pathway A including chemical reactions (a), (b), (c), (d), (e), (f), (g) and (h). FIG. 3A (iii) depicts a second example synthesis pathway B including chemical reactions (i), (j), (k), (l), and (m).

Thus, referring initially to FIG. 3A (i), a dry, 3-neck RBF was charged with 4-benzyloxyindole 1 (14.0 g, 62.7 mmol)

and Et$_2$O (327 mL) under Ar. The mixture was cooled down to 0° C. in an ice bath. An Argon sparge was placed on the RBF and into the reaction mixture to purge out the HCl gas released from the reaction. Oxalyl chloride (10.9 mL, 129 mmol) was added dropwise over 40 min, while maintaining the cold temperature. The mixture was stirred for 5 h at 0° C. (see: reaction (a)). The argon sparge was removed, and dimethylamine (157 mL, 314 mmol) (2 M in THF) was added dropwise at 0° C. over 1 h using an addition funnel. The mixture was allowed to warm up to RT and stir overnight (see: reaction (b)). Diethyl ether (200 mL) was added, and the mixture was cooled down to 0° C. The resulting precipitate (crude 3) was filtered and transferred to an Erlenmeyer flask. The solid was suspended in water (300 mL) and stirred for 30 min. Then, it was filtered and washed with more H$_2$O to remove residual salts. The crude solid was further dried in vacuo and used in the next step without further purification.

Lithium aluminum hydride (LiAlH$_4$) (60.2 mL, 120 mmol) (2M in THF) was added to a dry 3-neck flask under argon. The flask was fitted with a reflux condenser and an addition funnel. Dry 1,4-dioxane (100 mL) was added, and the mixture was heated to 60° C. in an oil bath. In a separate flask, compound 3 (7.46 g, 23.1 mmol) was dissolved in a mixture of THF (60 mL) and 1,4-dioxane (120 mL). With rapid stirring, this solution was added dropwise to the reaction flask over 1 h using an addition funnel. The oil bath temperature was held at 70° C. for 4 h, followed by vigorous reflux overnight (16 h) in an oil bath temperature of 95° C. The reaction was placed in an ice bath, and a solution of distilled H$_2$O (25 mL) in THF (65 mL) was added dropwise to quench LiAlH$_4$, resulting in a gray flocculent precipitate. Et$_2$O (160 mL) was added to assist breakup of the complex and improve filtration. This slurry was stirred for 1 h and the mixture was then filtered using a Buchner funnel. The filter cake was washed on the filter with warm Et$_2$O (2×200 mL) and was broken up, transferred back into the reaction flask, and vigorously stirred with additional warm Et$_2$O (300 mL). This slurry was filtered, and the cake was washed on the filter with Et$_2$O (120 mL) and hexane (2×120 mL). All the organic filtrates were combined and dried (MgSO$_4$). After the drying agent was removed by filtration, the filtrate was concentrated under vacuum and dried under high vacuum. The crude residue was triturated with EtOAc/hexanes (1:9, 25 mL) to afford the crude product (4) which was used in the next step without further purification (see: reaction ©).

To a solution of 4 (5.00 g, 17.0 mmol) in dry THF (100 mL) cooled to −78° C. under argon was added dropwise a 1 M solution of potassium bis(trimethylsilyl)amide (KHMDS) (18.7 mL, 18.7 mmol) in THF. After stirring at −78° C. for 1 h, a solution of triisopropylsilyl chloride (TIPSCl) (3.82 mL, 17.8 mmol) in THF (19.0 mL) was added dropwise over 15 minutes, and the reaction mixture was allowed to warm up to RT. After stirring at RT for 1 h, the reaction was quenched with H$_2$O (40 mL), THF was evaporated under reduced pressure, and the aqueous solution was further diluted with H$_2$O (75 mL) and extracted with DCM (3×100 mL). The organic layers were combined and washed with brine, dried over Na$_2$SO$_4$, filtered, and concentrated under reduced pressure. The crude product was purified by flash column chromatography (MeOH/DCM 5:95 to 10:90) to afford the pure product as a light brown oil (6.99 g, 91%). Product (5) was confirmed as follows: $^1$H NMR (400 MHz, CDCl$_3$) δ 7.58-7.51 (m, 2H), 7.44-7.39 (m, 2H), 7.38-7.33 (m, 1H), 7.12 (dd, J=8.4, 0.8 Hz, 1H), 7.08-6.99 (m, 1H), 6.94 (s, 1H), 6.60 (dd, J=7.7, 0.7 Hz, 1H), 5.20 (s, 2H), 3.12-3.04 (m, 2H), 2.67-2.58 (m, 2H), 2.16 (s, 6H), 1.69 (h, J=7.5 Hz, 3H), 1.16 (d, J=7.5 Hz, 18H) (see: reaction (d)).

To a stirring solution of 5 (6.99 g, 15.5 mmol) dissolved in EtOH, 95% (310 mL), was added 10% palladium on carbon (1.65 g, 1.55 mmol). This mixture was put under vacuum for five minutes, then alternately purged with H$_2$ gas until pressurized hydrogen atmosphere was established, then allowed to stir for 75 minutes at room temperature. The palladium on carbon was removed by filtration through celite, the filtrate dried with anhydrous magnesium sulphate, and concentrated under reduced pressure to yield 6 (4.67 g, 84%) as an off-white solid. Data confirming 6 are as follows: MS-ESI: calculated: 361.2670; observed: 361. 2668 m/z [M+H]$^+$. $^1$H NMR (400 MHz, MeOD) δ 6.98 (d, J=8.6 Hz, 2H), 6.91 (dd, J=8.4, 7.5 Hz, 1H), 6.42 (dd, J=7.5, 0.8 Hz, 1H), 3.06 (t, J=6.9 Hz, 2H), 2.77 (t, J=6.9 Hz, 2H), 2.39 (s, 6H), 1.72 (p, J=7.5 Hz, 3H), 1.16 (d, J=7.5 Hz, 18H). Notably, the organosilyl substituent on N1 of compound 6 can be abbreviated as TIPS (triisopropyl silyl). Thus, compound 6 may be referred to as TIPS-psilocin (see: reaction (e)).

Referring next to FIG. 3A (ii), a solution of compound 6 (100 mg, 277 μmol) and 4-nitrophenyl chloroformate (58.7 mg, 291 μmol) in dichloromethane (DC (1.39 mL) was cooled down to 0° C., and to it was added N,N-diisopropylethylamine (96.6 μL, 555 μmol) dropwise. The reaction was warmed up to RT and stirred for 2 h. After 2 h, TLC (MeOH/DCM 12:88) showed almost complete conversion to the desired product 7 (see: reaction (f)). To the reaction mixture (crude 7) was added a solution of benzyl mercaptan (49.3 μL, 416 μmol) and N,N-diisopropylethylamine (96.5 μL, 554 μmol) with vigorous stirring at RT. After 2 h, volatiles were removed in vacuo and the crude residue 8 was used in the next step without further purification (see: reaction (g)). To a solution of crude 8 (141 mg, 276 μmol) in dry THF (1.38 mL) was added tetrabutylammonium fluoride (TBAF) solution (1 M in tetrahydrofuran (THF), 414 μL, 414 μmol) dropwise at 0° C. After 30 min, water (2 mL) was added, the aq. layer was separated and extracted with DCM (3×15 mL). The combined organic layers were washed with brine, dried over anhydrous Na$_2$SO$_4$, filtered and concentrated. The crude product was purified by flash chromatography using silica gel (MeOH/DCM 1:9) to afford the pure product as a yellow waxy solid (33 mg, 34%). The following data were acquired for structural confirmation: MS-ESI, calculated: 355.1475; observed: 355.1467 m/z [M+H]*. $^1$H NMR (400 MHz, CDCl$_3$) δ 8.32 (s, 1H), 7.41-7.26 (m, 5H), 7.21 (d, J=8.2 Hz, 1H), 7.15-7.05 (m, 1H), 6.99-6.94 (m, 1H), 6.88 (dd, J=7.6, 0.8 Hz, 1H), 4.20 (s, 2H), 2.92 (dd, J=9.0, 6.7 Hz, 2H), 2.66-2.58 (m, 2H), 2.30 (s, 6H). These data confirmed the structure of a compound with the chemical formula 9 (see: reaction (h)). Purity of compound 9 was assessed at 95%. It is noted that the compound having formula 9 corresponds with E(VI).

Compound 9 (formula E(VI)) can also be synthesized using an alternative route without production of a psilocin intermediate according to example synthesis methods depicted in FIG. 3A (iii). Referring next to FIG. 3A (iii), to a mixture of triphosgene 10 (0.50 g, 1.68 mmol) and triethylamine (694 μL, 4.96 mmol) in DCM (19.0 mL) at −10° C. (NaCl/water/ice bath) was added benzyl mercaptan (582 μL, 4.96 mmol) in DCM (1.5 mL). The mixture was warmed up to RT and stirred for 2 hours. Two-thirds of the volatiles were removed under reduced pressure, and hexane (25 mL) was added to the residue. The resulting precipitate was filtered, and the filtrate was concentrated in vacuo to give the crude product 11 as a yellow oil which was used in the next step without further purification (see: reaction (m)). Psilocin (15) synthesis has been described previously (Shirota et al., J. Nat. Prod. 2003, 66:885-887; Kargbo et al., ACS Omega 2020, 5:16959-16966) but is shown for clarity and completeness in FIG. 3A (iii)) (see: reactions (i), (j), and (k)). To a solution of psilocin 15 (50.0 mg, 245 µmol) and potassium carbonate (33.8 mg, 245 µmol) in DMF (1.00 mL) was added a solution of 11 (137 mg, 734 µmol, 3 eq.) in dimethyl formamide (DMF) (500 µL). The resulting mixture was stirred at room temperature for 18 hours. TLC analysis (MeOH/DCM 15:85, UV and KMnO4 stain) against an authentic standard of 9 (i.e., compound E(VI)) showed ~60% conversion to compound 9 ($R_f$: 0.4) and ~40% remaining psilocin (see: reaction (l)).

It is noted that there are several ways to introduce a thiocarbonate moiety on a molecule, including: (1) formation of an activated p-nitrophenyl carbonate, followed by displacement of the p-nitrophenol with the desired thiol (see: reactions (f) and (g) in FIG. 3A (ii)); or (2) using different thiocarbonylating reagents, namely an alkylchlorothioformate (e.g., compound 11 in FIG. 3A (iii)) or an alkylimidazolothioformate (16):

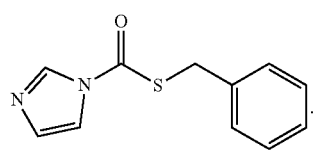

(16)

Due to the presence of competing nucleophilic sites on psilocin (4-OH and indolic nitrogen), the above thiocarbonylating reagents show different reactivities towards this molecule. To obtain an optimized synthesis route for installing a thiocarbonate moiety, synthesis reactions using various reagents (e.g., compounds 11, 16) and reactions (e.g., reactions ((f), (g)), or (l)) may be conducted and compared in different synthesis routes, for example, with respect to yield, ease of operation, and a preferred reagent and reaction may be selected.

It is noted that a difference between the synthesis pathway shown in FIGS. 3A (i) and 3A (ii) (pathway A), on the one hand, and FIG. 3A (iii) (pathway B), on the other hand, is that in synthesis pathway A the aromatic nitrogen requires protection to achieve the desired reactivity between a p-nitrophenylformylating reagent and psilocin, hence the use of $N^{indole}$-TIPS intermediate (compound 6). However, in synthesis pathway B the use of reagent 11 does not necessitate the protection of the aromatic indole nitrogen atom, resulting in a synthesis pathway requiring the performance of a smaller number of total steps.

Assessment of Cell Viability Upon Treatment of a Psilocin Derivative.

Figure 3B:
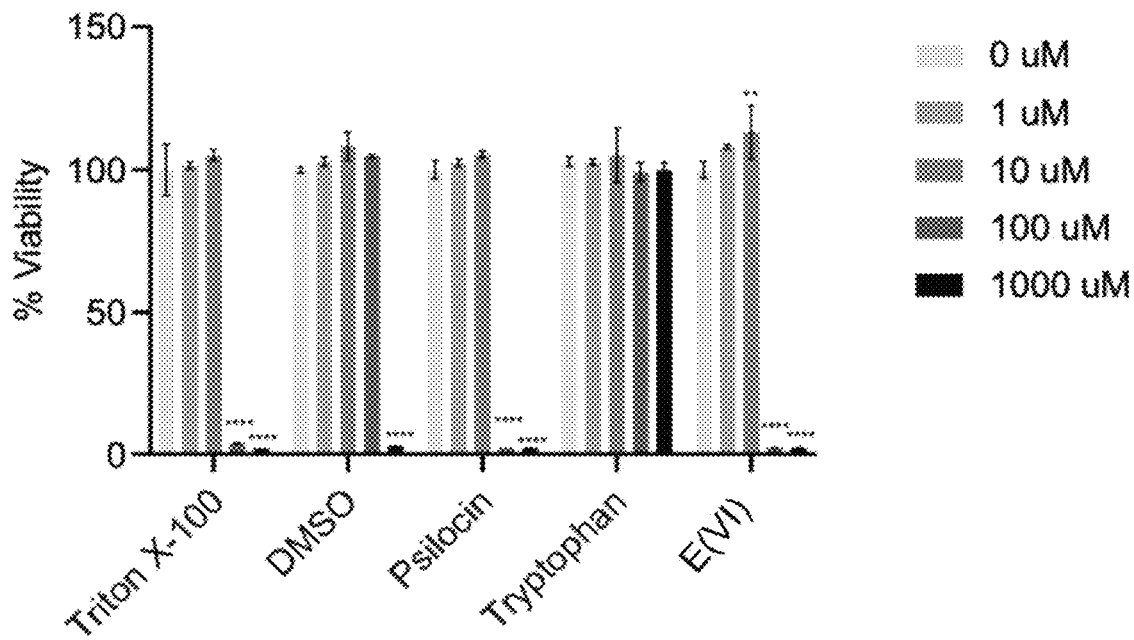

To establish suitable ligand concentrations for competitive binding assays, PrestoBlue assays were first performed. The PrestoBlue assay measures cell viable activity based on the metabolic reduction of the redox indicator resazurin, and is a preferred method for routine cell viability assays (Terrasso et al., 2017, J. Pharmacol. Toxicol. Methods 83: 72). Results of these assays were conducted using both control ligands (e.g., psilocybin, psilocin, DMT) and novel derivatives, in part as a pre-screen for any remarkable toxic effects on cell cultures up to concentrations of 1 mM. A known cellular toxin (Triton X-100, Pyrgiotakis G. et al., 2009, Ann. Biomed. Eng. 37: 1464-1473) was included as a general marker of toxicity. Drug-induced changes in cell health within simple in vitro systems such as the HepG2 cell line are commonly adopted as first-line screening approaches in the pharmaceutical industry (Weaver et al., 2017, Expert Opin. Drug Metab. Toxicol. 13: 767). HepG2 is a human hepatoma that is most commonly used in drug metabolism and hepatotoxicity studies (Donato et al., 2015, Methods Mol Biol 1250: 77). Herein, HepG2 cells were cultured using standard procedures using the manufacture's protocols (ATCC, HB-8065). Briefly, cells were cultured in Eagle's minimum essential medium supplemented with 10% fetal bovine serum and grown at 37° C. in the presence of 5% $CO_2$. To test the various compounds with the cell line, cells were seeded in a clear 96-well culture plate at 20,000 cells per well. After allowing cells to attach and grow for 24 hours, compounds were added at 1 mM, 10 mM, 100 mM, and 1 mM. Methanol was used as vehicle, at concentrations 0.001, 0.01, 0.1, and 1%. As a positive control for toxicity, TritonX concentrations used were 0.0001, 0.001, 0.01 and 0.1%. Cells were incubated with compounds for 48 hours before assessing cell viability with the PrestoBlue assay following the manufacture's protocol (ThermoFisher Scientific, P50200). PrestoBlue reagent was added to cells and allowed to incubate for 1 hour before reading. Absorbance readings were performed at 570 nm with the reference at 600 nm on a SpectraMax iD3 plate reader. Non-treated cells were assigned 100% viability. Bar graphs show the mean+/−SD, n=3. Significance was determined by 2-way ANOVA followed by Dunnett's multiple comparison test and is indicated by * ($P<0.0001$), ($P<0.001$), *($P<0.005$). Data acquired for the derivative having chemical formula E(VI) is displayed as "E(VI)" on the x-axis in FIGS. 3B and 3C.

Radioligand Receptor Binding Assays.

Figure 3C:
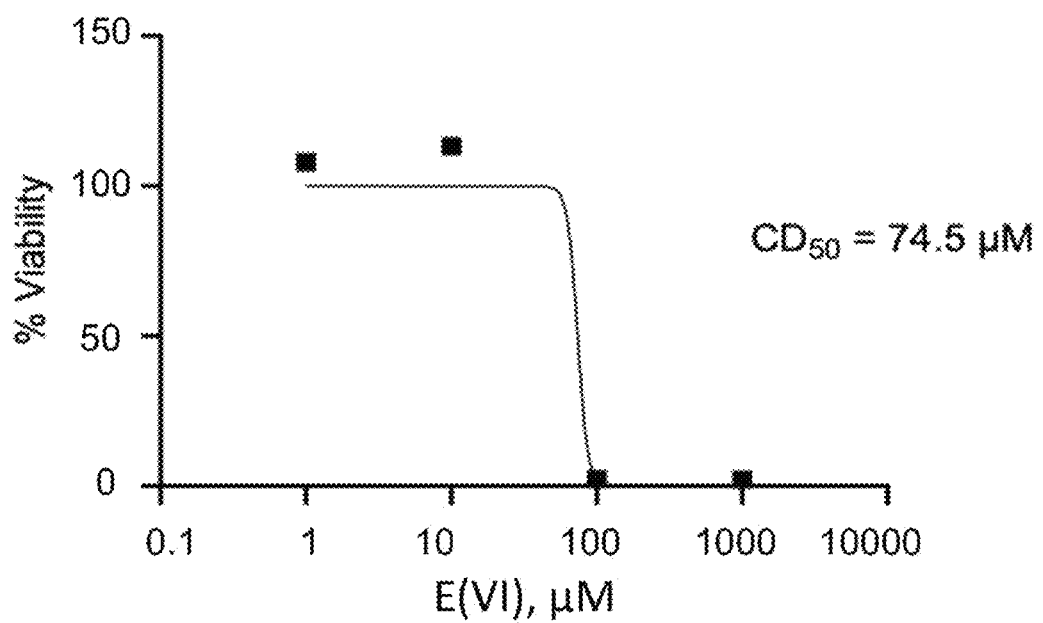
Figure 3D:
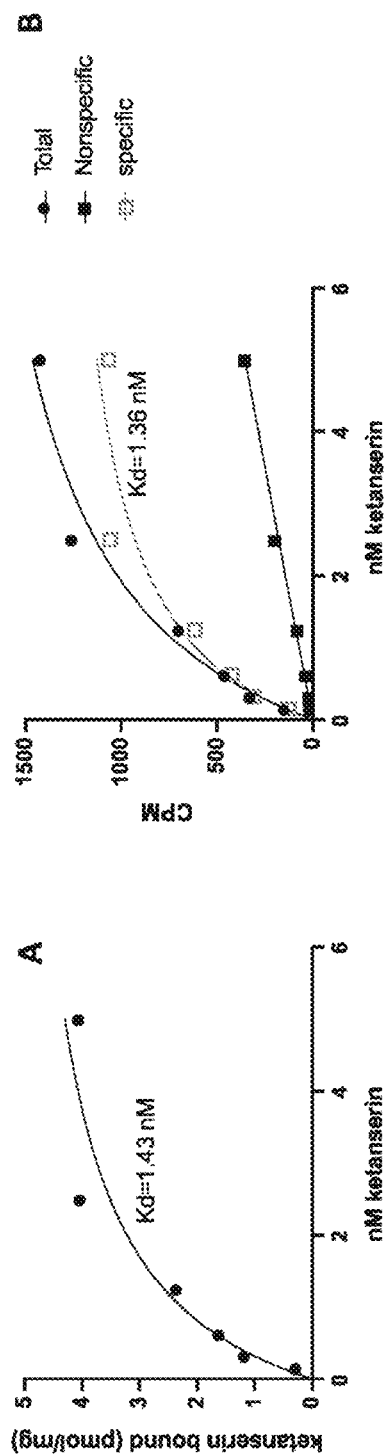
Figure 3E:
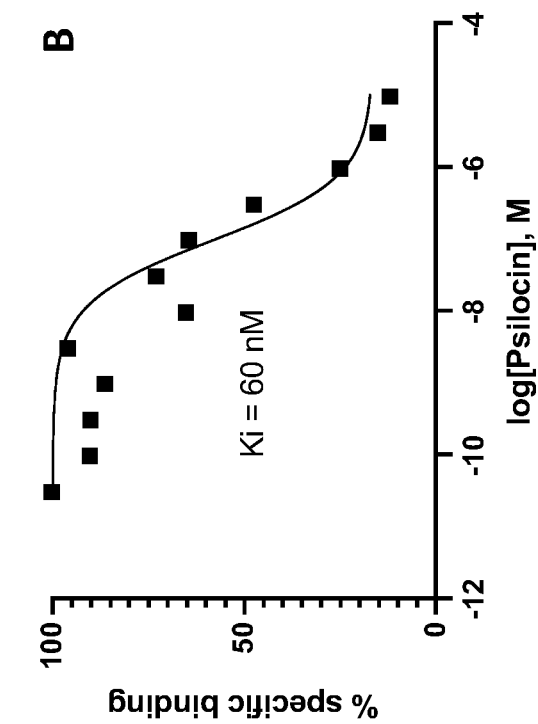
Figure 3E:
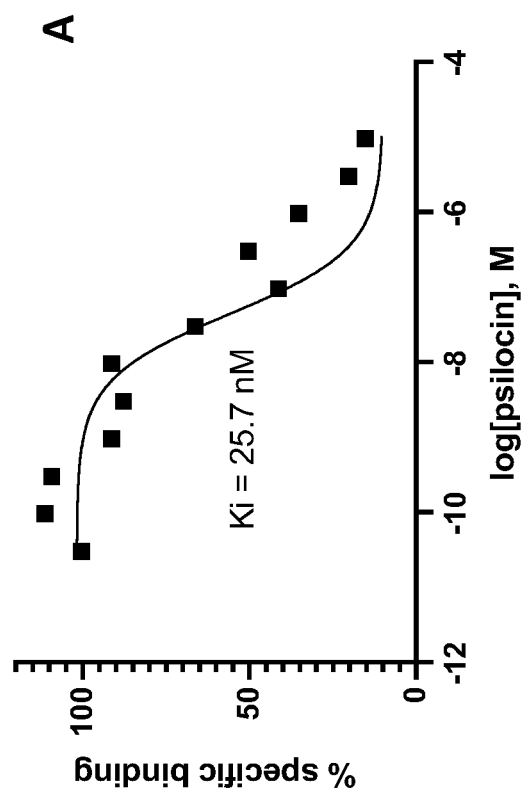
Figure 3F:
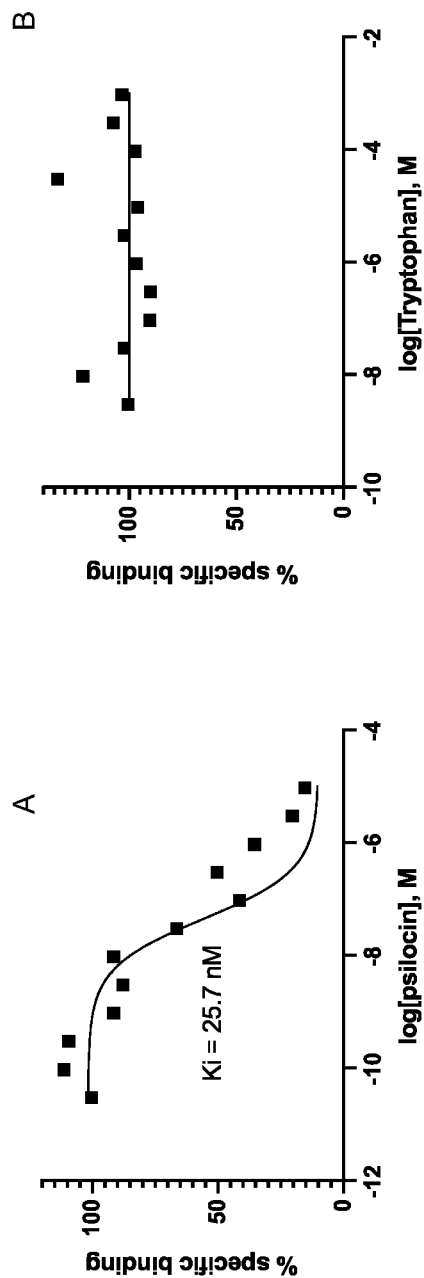
Figure 3G:
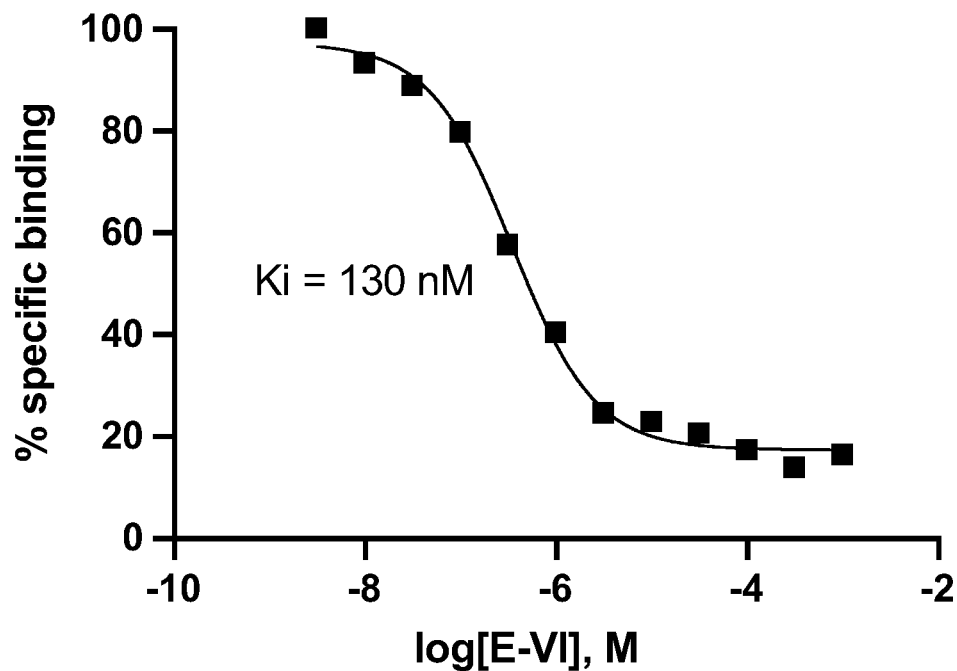

Activity at $5-HT_{2A}$ receptor was assessed as described as follows. Evaluation of drug binding is an essential step to characterization of all drug-target interactions (Fang 2012, Exp. Opin. Drug Discov. 7:969). The binding affinity of a drug to a target is traditionally viewed as an acceptable surrogate of its in vivo efficacy (Núñez et al., 2012, Drug Disc. Today 17: 10). Competition assays, also called displacement or modulation binding assays, are a common approach to measure activity of a ligand at a target receptor (Flanagan 2016, Methods Cell Biol 132: 191). In these assays, standard radioligands acting either as agonists or antagonists are ascribed to specific receptors. In the case of G protein-coupled receptor $5-HT_{2A}$, [$^3$H]ketanserin is a well-established antagonist used routinely in competition assays to evaluate competitive activity of novel drug candidates at the $5-HT_{2A}$ receptor (Maguire et al., 2012, Methods Mol Biol 897: 31). Thus, to evaluate activity of novel $C_4$-carbonothioate-substituted tryptamine derivatives at the $5-HT_{2A}$ receptor, competition assays using [$^3$H]ketanserin were employed as follows. SPA beads (RPNQ0010), [$^3$H] ketanserin (NET1233025UC), membranes containing $5-HT_{2A}$ (ES-313-M400UA), and isoplate-96 microplate (6005040) were all purchased from PerkinElmer. Radioactive binding assays were carried out using Scintillation Proximity Assay (SPA). For saturation binding assays, mixtures of 10 ug of membrane containing $5-HT_{2A}$ receptor was pre-coupled to 1 mg of SPA beads at room temperature in a tube rotator for 1 hour in binding buffer (50 mM Tris-HCl pH7.4, 4 mM $CaCl_2$, 1 mM ascorbic acid, 10 mM pargyline HCl). After pre-coupling, the beads and membrane were aliquoted in an isoplate-96 microplate with increasing amounts of [$^3$H]ketanserin (0.1525 nM to 5 nM) and incubated for two hours at room temperature in the dark with shaking. After incubation, the samples were read on a MicroBeta 2 Microplate Counter (Perkin Elmer). Determination of non-specific binding was carried out in the presence of 20 mM of spiperone (S7395-250MG, Sigma). Equilibrium binding constants for ketanserin ($K_d$) were determined from saturation binding curves using the 'one-site saturation binding analysis' method of GraphPad PRISM software (Version 9.2.0). Competition binding assays were performed using fixed (1 nM) [$^3$H]ketanserin and different concentrations of tryptophan (3 nM to 1 mM), psilocin (30 µM to 10 mM) or unlabeled test compound (3 nM to 1 mM) similar to the saturation binding assay. $K_i$ values were calculated from the competition displacement data using the competitive binding analysis from GraphPad PRISM software. Tryptophan was included as a negative control as it has no activity at the 5-$HT_{2A}$ receptor. In contrast, psilocin was used as a positive control since it has established binding activity at the 5-$HT_{2A}$ receptor (Kim et al., 2020, Cell 182: 1574). FIG. 3D depicts the saturation binding curves for [$^3$H]ketanserin at the 5-$HT_{2A}$ receptor. Panel A shows the specific saturation ligand binding of [$^3$H]ketanserin (from 0.1525 nM to 5 nM) to membranes containing 5-$HT_{2A}$ receptor, which was obtained after subtracting non-specific binding values (shown in Panel B). Specific binding in counts per minute (cpm) was calculated by subtracting non-specific binding from total binding. Specific binding (pmol/mg) was calculated from pmol of [$^3$H]ketanserin bound per mg of protein in the assay. The $K_d$ was calculated by fitting the data with the one-site binding model of PRISM software (version 9.2.0). FIG. 3E shows the results of two independent trials (Panels A and B) yielding two competition binding curves for psilocin as a positive control (binding). FIG. 3F shows the competition binding curves for psilocybin (Panel A) and tryptophan (Panel B). Psilocybin is known to release the 5-$HT_{2A}$-binding metabolite psilocin in vivo; however, the intact psilocybin molecule itself displays very weak (McKenna and Peroutka 1989, J. Neurosci. 9: 3482) or arguably negligible (PDSP Certified Data; https://pdsp.unc.edu/databases/pdsp.php) binding at 5-$HT_{2A}$. Tryptophan is included as a negative control (no binding). The competition binding curve for compound with formula E(VI), designated "E-VI" shown in FIG. 3G.

Cell Lines and Control Ligands Used to Assess Activity at 5-$HT_{1A}$.

CHO-K1/$Ga_{15}$ (GenScript, M00257) (−5-$HT_{1A}$) and CHO-K1/5-$HT_{1A}$/$Ga_{15}$ (GenScript, M00330) (+5-$HT_{1A}$) cells lines were used. Briefly, CHO-K1/$Ga_{15}$ is a control cell line that constitutively expresses $Ga_{15}$ which is a promiscuous $G_q$ protein. This control cell line lacks any transgene encoding 5-$HT_{1A}$ receptors, but still responds to forskolin; thus, cAMP response to forskolin should be the same regardless of whether or not 5-$HT_{1A}$ agonists are present. Conversely, CHO-K1/5-$HT_{1A}$/$Ga_{15}$ cells stably express 5-$HT_{1A}$ receptor in the CHO-K1 host background. Notably, $Ga_{15}$ is a promiscuous G protein known to induce calcium flux response, present in both control and 5-$HT_{1A}$ cell lines. In +5-$HT_{1A}$ cells, $Ga_{15}$ may be recruited in place of $G_{ai/o}$, which could theoretically dampen cAMP response (Rojas and Fiedler 2016, Front Cell Neurosci. 10: 272). Thus, we included two known 5-$HT_{1A}$ agonists, psilocin (Cameron and Olson 2018, ACS Chem Neurosci. 9: 2344) and serotonin (Rojas and Fiedler 2016, Front Cell Neurosci. 10: 272) as positive controls to ensure sufficient cAMP response was observed, thereby indicating measurable recruitment of $G_{ai/o}$ protein to activated 5-$HT_{1A}$ receptors. In contrast, tryptophan is not known to activate 5-$HT_{1A}$ receptors, and was thus used as a negative control. Cells were maintained in complete growth media as recommended by supplier (GenScript) which is constituted as follows: Ham's F12 Nutrient mix (HAM's F12, GIBCO #11765-047) with 10% fetal bovine serum (FBS) (Thermo Scientific #12483020), 200 mg/ml zeocin (Thermo Scientific #R25005) and/or 100 mg/ml hygromycin (Thermo Scientific #10687010). The cells were cultured in a humidified incubator with 37° C. and 5% $CO_2$. Cells maintenance was carried out as recommended by the cell supplier. Briefly, vials with cells were removed from the liquid nitrogen and thawed quickly in 37° C. water bath. Just before the cells were completely thawed the vial's outside was decontaminated by 70% ethanol spray. The cell suspension was then retrieved from the vial and added to warm (37° C.) complete growth media, and centrifuged at 1,000 rpm for 5 minutes. The supernatant was discarded, and the cell pellet was then resuspended in another 10 ml of complete growth media, and added to the 10 cm cell culture dish (Greiner Bio-One #664160). The media was changed every third day until the cells were about 90% confluent. The ~90% confluent cells were then split 10:1 for maintenance or used for experiment.

Evaluation of 5-$HT_{1A}$ Receptor Modulation.

Figure 3H:
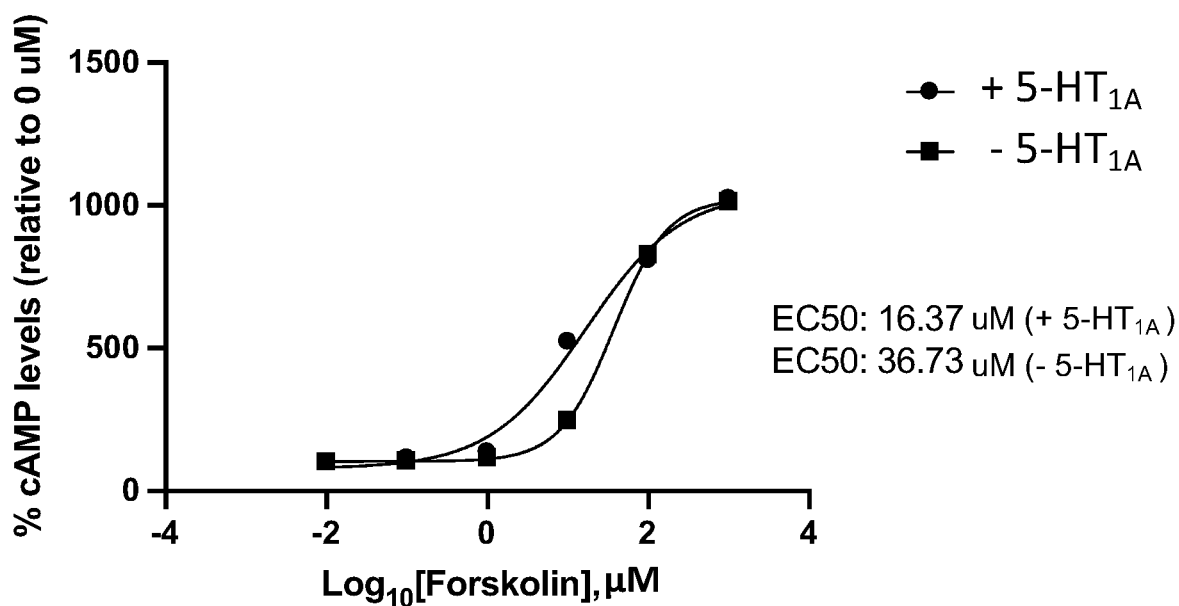
Figure 3I:
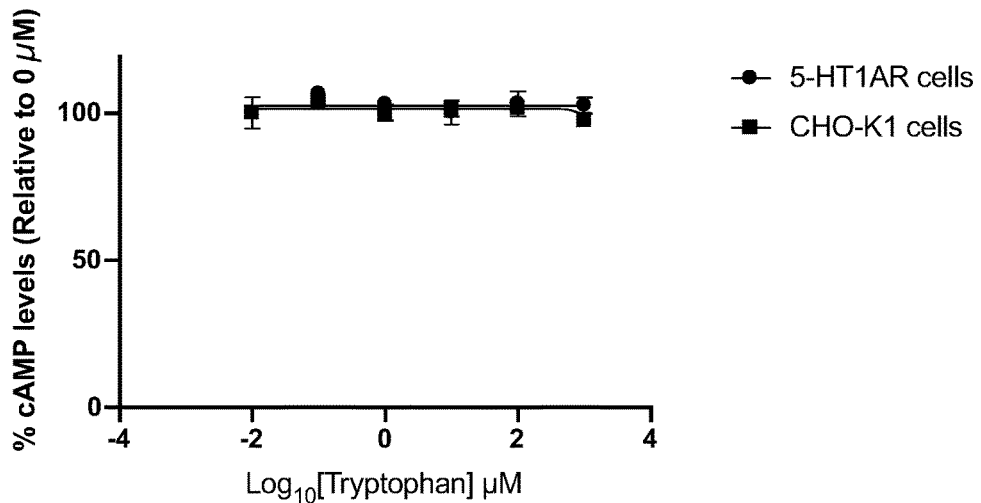
Figure 3J:
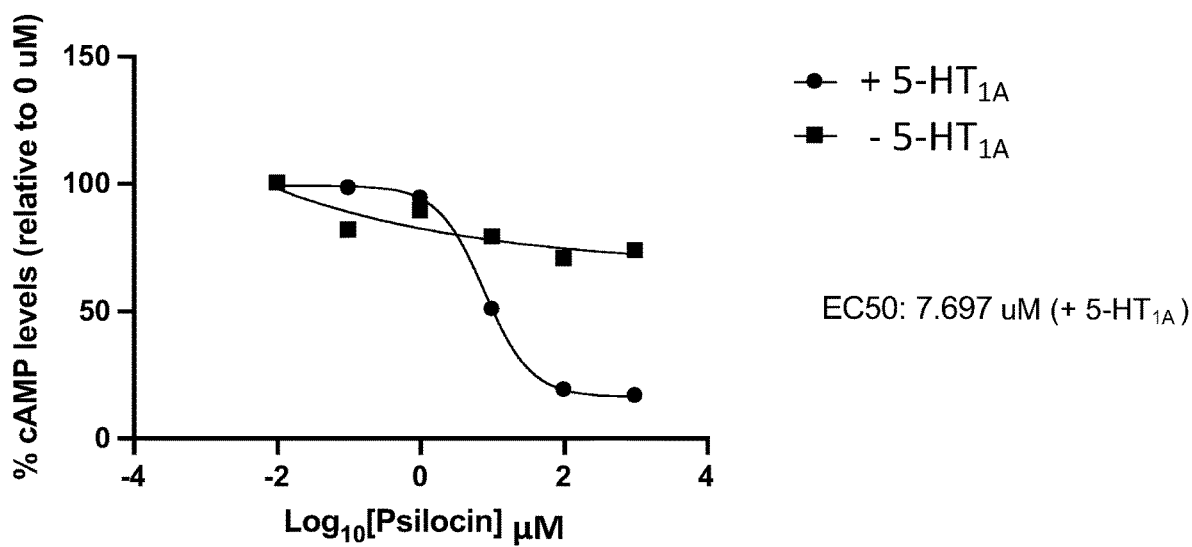
Figure 3K:
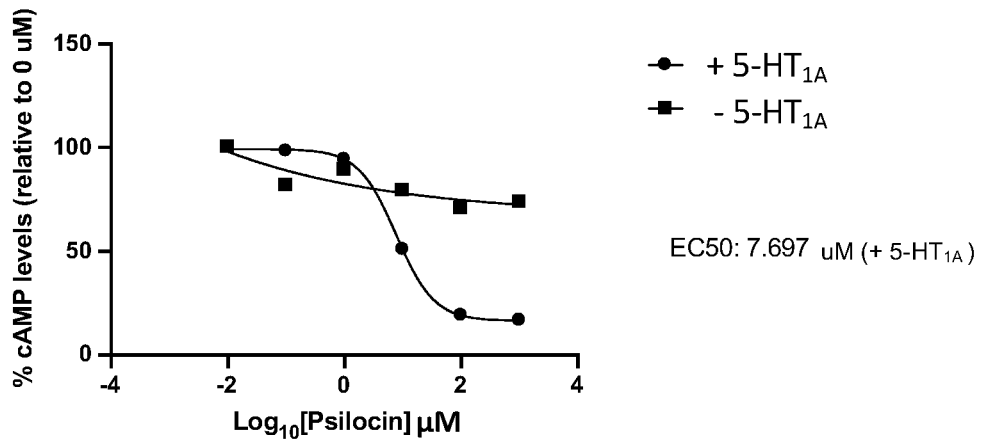
Figure 3L:
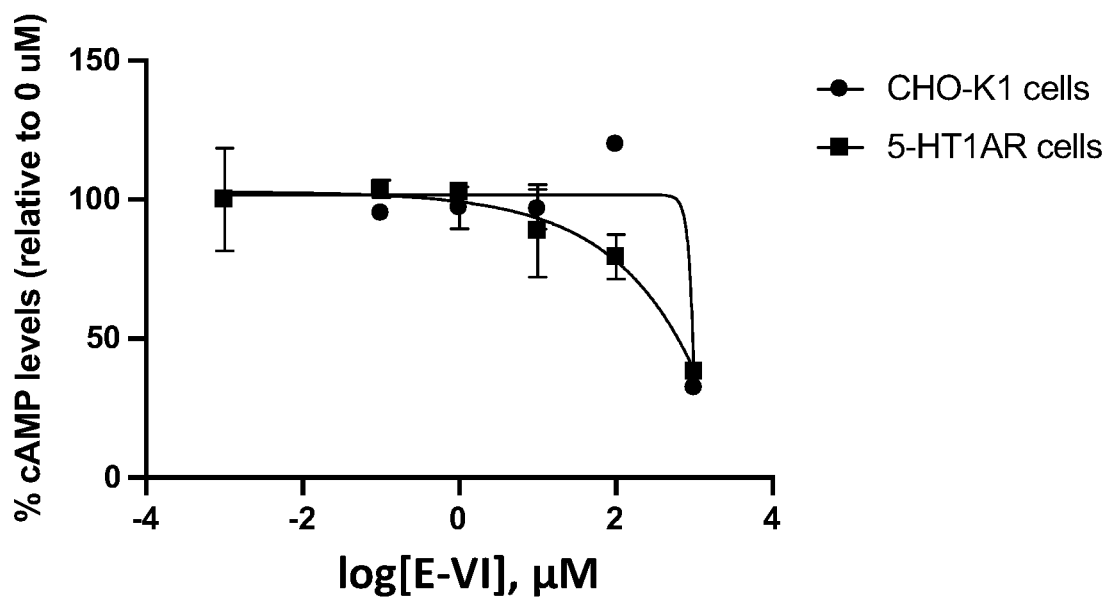
Figure 3:
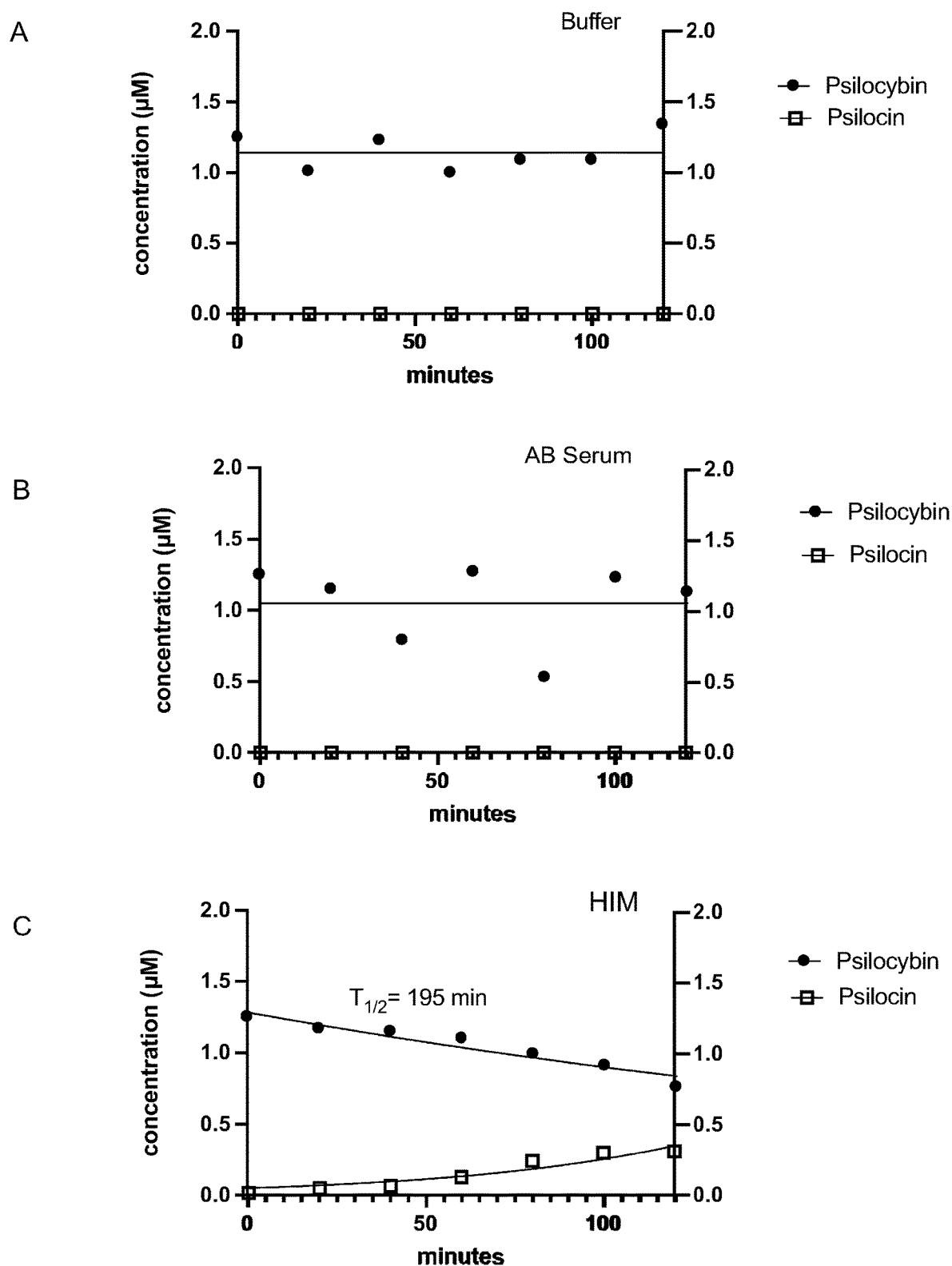

As 5-$HT_{1A}$ activation inhibits cAMP formation, the agonist activity of test molecules on 5-$HT_{1A}$ was measured via the reduction in the levels of cAMP produced due to application of 4 mM forskolin. The change in intracellular cAMP levels due to the treatment of novel molecules was measured using cAMP-Glo Assay kit (Promega #V1501). Briefly, +5-$HT_{1A}$ cells were seeded on 1-6 columns and base −5-$HT_{1A}$ cells were seeded on columns 7-12 of the white walled clear bottom 96-well plate (Corning, #3903). Both cells were seeded at the density of 30,000 cells/well in 100 ml complete growth media and cultured 24 hrs in humidified incubator at 37° C. and 5% $CO_2$. On the experiment day, the media of cells was replaced with serum/antibiotic free culture media. Then the cells were treated for 20 minutes with test molecules dissolved in induction medium (serum/antibiotic free culture media containing 4 mM forskolin, 500 mM IBMX (isobutyl-1-methylxanthine, Sigma-Aldrich, Cat. #17018) and 100 mM (RO 20-1724, Sigma-Aldrich, Cat. #B8279)). Forskolin induced cAMP formation whereas IBMX and RO 20-1724 inhibited the degradation of cAMP. The level of luminescence in cells incubated with induction medium (containing 4 mM forskolin) without test molecules was normalized to represent 100% cAMP in this assay. PKA was added to the lysate, mixed, and subsequently the substrate of the PKA was added. PKA was activated by cAMP, and the amount of ATP consumed due to PKA phosphorylation directly corresponded to cAMP levels in the lysate. Reduced ATP caused reduced conversion of luciferin to oxyluciferin, conferring diminished luminescence as the result of 5-$HT_{1A}$ activation. FIG. 3H shows increasing levels of cAMP in cultured cells incubated with increasing concentrations of forskolin independent of 5-$HT_{1A}$ expression. FIG. 3I illustrates no reduction in cellular cAMP levels in either cell culture (+5-$HT_{1A}$ and −5-$HT_{1A}$) stimulated with induction medium and treated with increasing doses of tryptophan, indicating a lack of 5-$HT_{1A}$ activity by this molecule in +5-$HT_{1A}$ cells. FIG. 3J illustrates reduction in cAMP levels in 5-$HT_{1A}$ receptor expressing cells (+5-$HT_{1A}$) stimulated with 4 mM forskolin as levels of psilocin increase, indicating 5-$HT_{1A}$ receptor binding by psilocin in these cells. Conversely, this trend of decreasing % cAMP levels with increasing psilocin is not observed in cells lacking expression of 5-$HT_{1A}$ receptor. FIG. 3K illustrates reduction in cAMP levels in 5-$HT_{1A}$ receptor expressing cells stimulated with 4 mM forskolin as levels of serotonin (5-HT) increase, indicating 5-HT$_{1A}$ receptor binding by serotonin (5-HT) in these cells. Conversely, this trend of decreasing % cAMP levels with increasing serotonin (5-HT) is not observed in cells lacking expression of 5-HT$_{1A}$ receptor. 5-HT$_{1A}$ receptor binding evaluation for compound with formula E(VI) (designated simply "E-VI" along the x-axis) is shown in FIG. 3L. Comparison of data acquired in +5-HT$_{1A}$ cultures with those acquired in −5-HT$_{1A}$ cultures suggests mild receptor modulation at higher ligand concentrations.

In Vitro Metabolic Stability Assays Using Intestinal Fractions, Liver Fractions, Serum Fractions, Alkaline Phosphatase Buffer, Esterase Buffer, and Control Buffer.

A fundamental evaluation in drug development is the assessment of absorption, distribution, metabolism, excretion, and pharmacokinetics (ADME/PK) (Eddershaw et al., 2000, Drug Discovery Today 5(9): 409-414). The first ADME screen that a novel chemical entity is subjected to is an in vitro metabolic stability screen (Ackley et al., 2004, Methods in Pharmacology and Toxicology Optimization in Drug Discovery (in vitro methods), Yan Z, Caldwell G. W. Eds; Humana Press Inc, New Jersey, pp. 151-164). Drug stability upon exposure to human liver microsomes and liver S9 cellular fractions is a common in vitro assay to approximate in vivo, liver-based drug metabolism (Richardson et al., 2016 Drug Metabolism Letters 10:83-90). First-pass metabolism is also often approximated in vitro using intestinal microsome and cellular S9 fractions (Hatley et al., 2017, Biopharmaceuticals & Drug Disposition, 38(2):155-160). Further, it is well known that human serum, and particularly circulating serum esterases can contribute to systemic drug metabolism (Williams, F M 1987, Pharmacology and Therapeutics, 34:99-109). Many pharmacological agents are classified as prodrugs, as they undergo metabolic transformation in vivo upon administration to release the active drug compound into the systemic compartment (Zawilska J B, et al. 2013, Pharmacological Reports, 65:1-14). Psilocybin, a serotonergic psychedelic agent, is well known prodrug that is metabolized into the psychoactive product, psilocin (Dinis-Oliveira, R J 2017, Drug Metabolism Reviews, 49(1):84-91). To evaluate the capacity of test molecules to similarly serve as prodrugs of psilocin, time-dependent, metabolic stability assays using human AB serum, human intestinal microsomes (HIM), human intestinal S9 fractions (HIS9), human liver microsomes (HLM), human liver S9 fractions (HLS9), human alkaline phosphatase, and porcine esterase were performed. Assays in enzyme-free buffer were also performed for control purposes, and for general assessment of compound stability. Liquid chromatography coupled mass spectrometry (LC-MS) was employed to track the conversion of the test molecules into psilocin. All intestinal and liver fractions and NADPH RapidStart reagent was purchased from Sekisui/XenoTech. Human AB serum was purchased from Sigma. For intestine and liver metabolism assays, 2.5 µM candidate compounds were incubated in 400 µg/ml of each cellular fraction (HLM, HLS9, HIM, or HIS9) in 50 mM potassium phosphate buffer (pH 7.4) containing 3 mM MgCl$_2$ and 1 mM EDTA supplemented with NADPH RapidStart at 37° C. Samples were taken at the start of the assay, and at every 20 minutes for 2 hours. Time-point samples were precipitated with 1:1 volume of acetonitrile to quench the reaction before centrifugation at 4000×g for 20 minutes. Supernatants were analyzed for the presence of candidate prodrugs (parent molecule) and psilocin (the predicted metabolite) using Orbitrap LC-MS (Thermo Scientific) using previously described methods (Menéndez-Perdomo et al., 2021, J. Mass Spectrom., 56: e4683). The serum assays were carried out in 10% human AB serum in 50 mM potassium phosphate buffer (pH 7.4) containing 3 mM MgCl$_2$ and 1 mM EDTA. Bovine alkaline phosphatase assays were carried out using one unit of purified enzyme in 50 mM potassium phosphate buffer (pH 7.4) containing 3 mM MgCl$_2$ and 1 mM EDTA. Porcine esterase assays were carried out using one unit of purified enzyme in 50 mM potassium phosphate buffer (pH 7.4) containing 3 mM MgCl$_2$ and 1 mM EDTA. Assay concentrations (µM) of both parent 'prodrug' molecule and psilocin metabolite, as quantified through LC-MS using routine standard curve procedures, were plotted as functions of assay time (minutes). The metabolism rate ($T_{1/2}$) was determined from the metabolism curve plot using the one phase decay feature of GraphPad PRISM software (Version 9.2.0). The quantity of parent prodrug at time zero was set as 100%.

Positive controls were first tested to ensure that assays were functioning properly. Psilocybin is known to be metabolized to psilocin in the intestine and through alkaline phosphatase (Dinis-Oliveira, 2017 Drug Metab. Rev. 49: 84-91) and thus served as a positive control for HIM, HIS9 and alkaline phosphatase assays. Procaine is known to be metabolized to 4-amino benzoic acid in serum, liver, and through esterase (Henrikus and Kampffmeyer, 1992, Xenobiotica 22: 1357-1366) and thus served as a positive control for AB serum, HLM and esterase assays. Verapamil is known to be metabolized into a variety of metabolites in liver (Hanada et al., 2008, Drug Metab. Dispos. 36: 2037-2042) (catabolites not examined in this study) and thus served as an additional control for HLS9 and HLM assays.

Figure 3N:
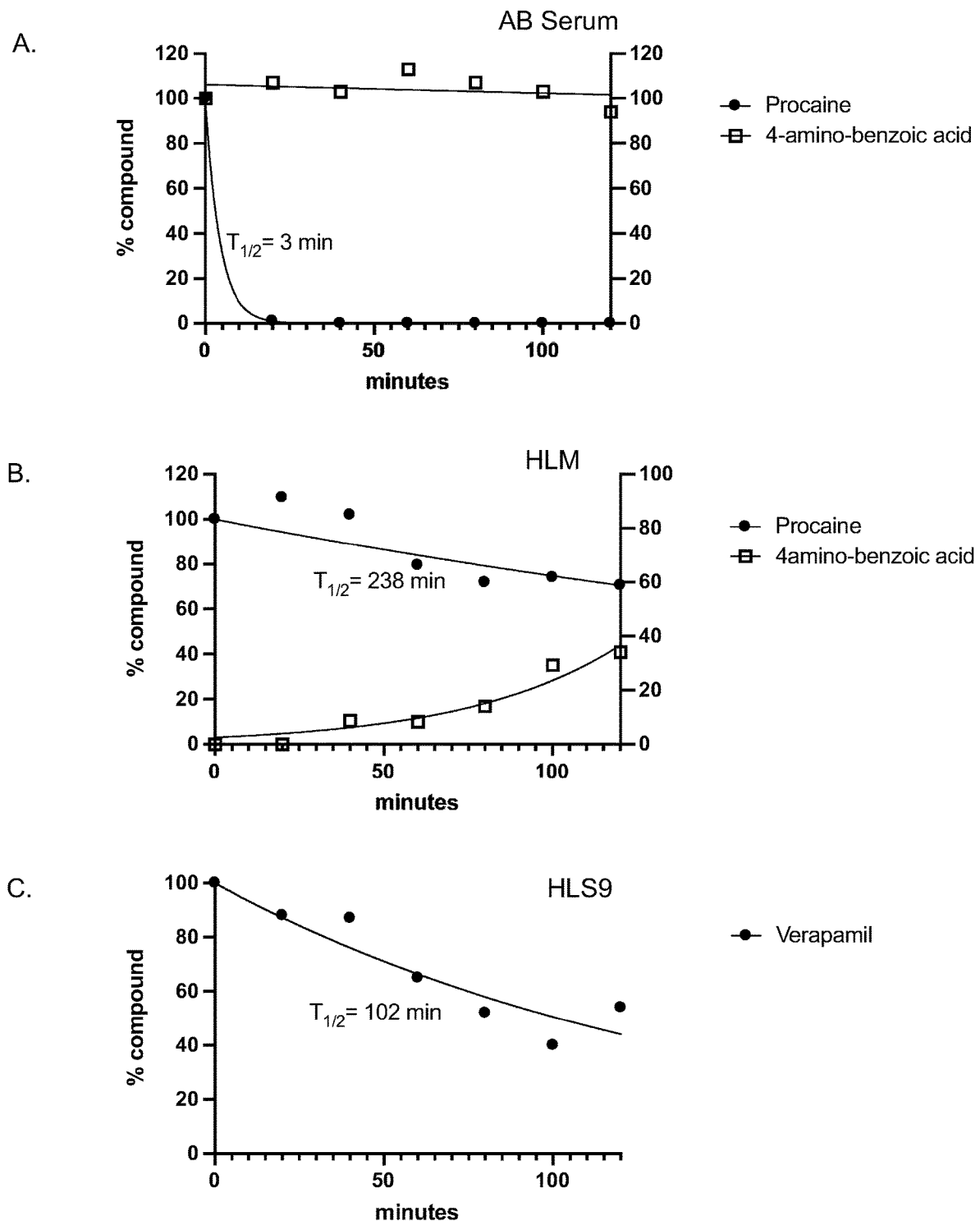
Figure 3O:
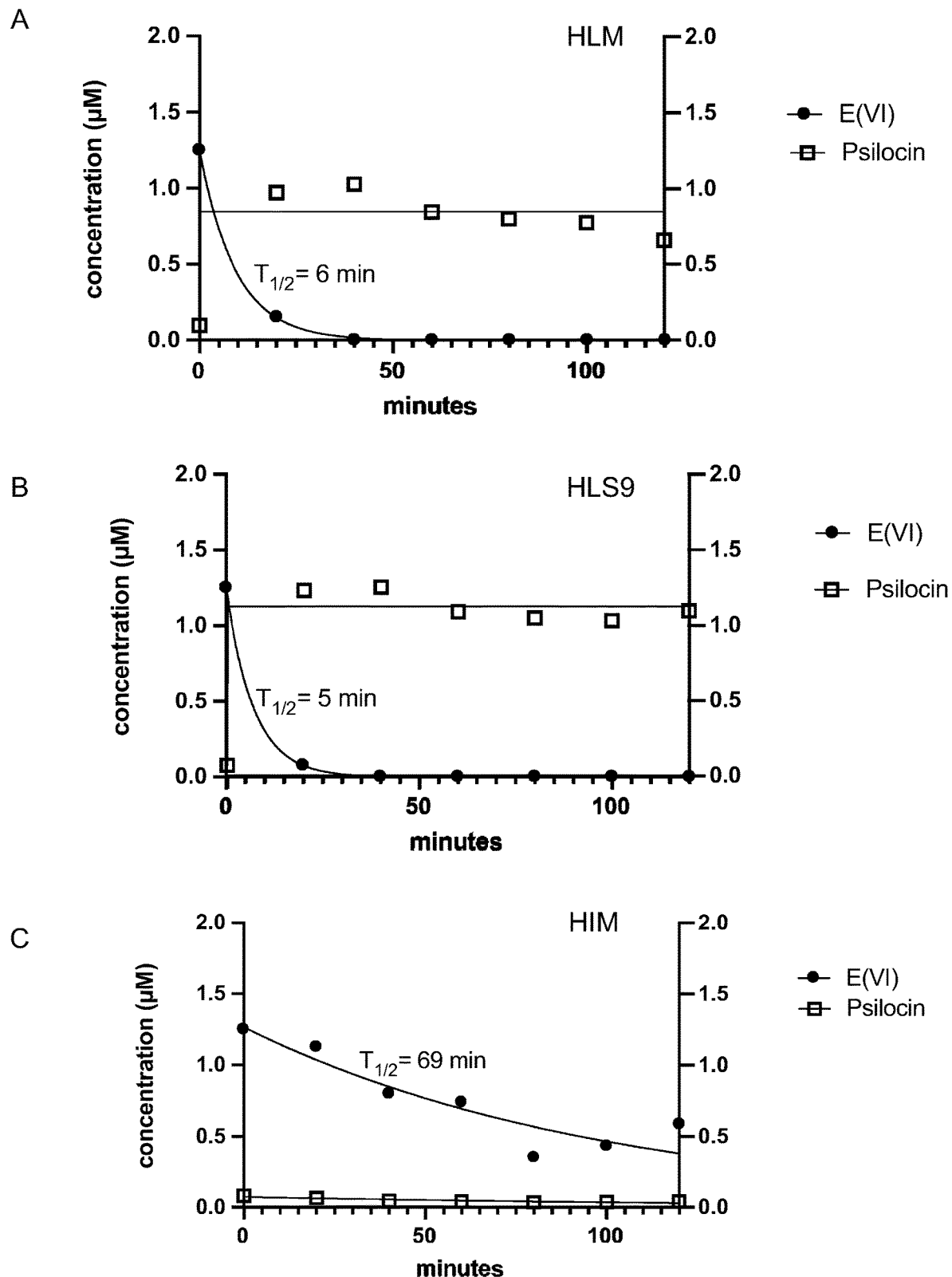

FIGS. 3M (i), 3M (ii) and 3M (iii) illustrate results of 'psilocin-release' metabolic conversion assays using psilocybin as the parent prodrug control for HIM (Panel C), HIS9 (Panel D) and alkaline phosphatase (Panel E) assays. For context, psilocybin was further submitted to negative control buffer assay (Panel A), AB serum (Panel B), HLM (Panel F), and HLS9 (Panel G) assays. Notably, these plots demonstrate psilocybin is stable in liver fractions with no conversion to psilocin. Further, the stability of psilocybin was confirmed in assay buffer, confirming that transformation of this molecule is due to enzymes within the cellular fractions rather than due to buffer components. Finally, these results demonstrate psilocybin is stable in serum with no conversion to psilocin. FIGS. 3N (i) and 3N (ii) illustrate results of additional controls for assay verification: procaine and AB serum (Panel A); procaine and HLM (Panel B); verapamil and HLS9 (Panel C); procaine and esterase (Panel D); verapamil and HLM (Panel E). FIGS. 3O (i) and 3O(ii) show the metabolic stability curves for compound with formula E(VI), designated "E(VI)," in HLM (Panel A), HLS9 (Panel B), HIM (Panel C), HIS9 (Panel D), AB serum (Panel E), and buffer control (Panel F).

In Vivo Evaluation of 5-HT$_{2A}$ Receptor Agonism in Mice.

Drug-induced Head Twitch Response (HTR), a rapid, involuntary movement of the mouse's head with little or no involvement of the trunk, is an established in vivo model behavior used to measure neuronal 5-HT$_{2A}$ receptor (5-HT2AR) activation by established and novel hallucinogenic compounds (Canal and Morgan 2012, Drug Testing Analysis, 4:556-576). Indeed, HTR is widely utilized as a behavioral proxy in mice and rats to predict human hallucinogenic potential and can reliably differentiate between hallucinogenic and non-hallucinogenic 5-HT2AR agonists (Halberstadt and Geyer 2013, Psychopharmacology 227: 727-739; Gonzalez-Maeso et al., 2007, Neuron 53:439-452).

Figure 3P:
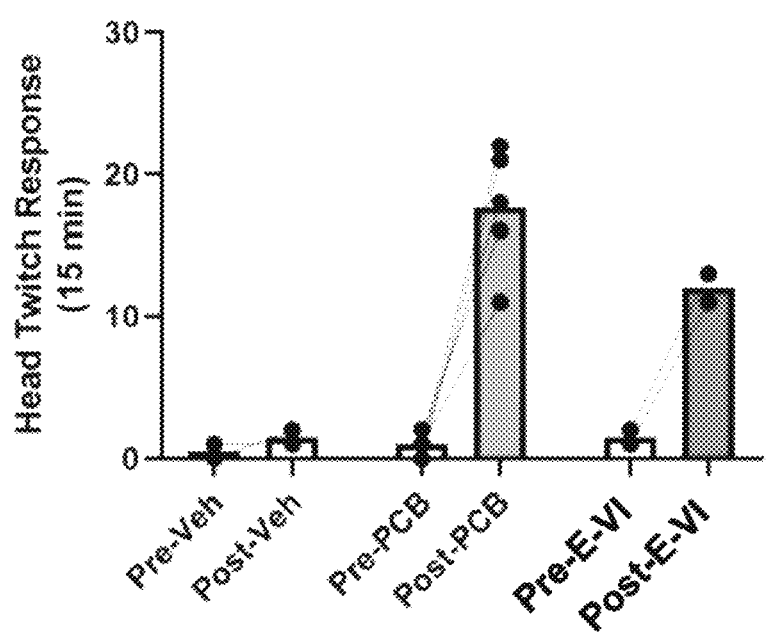

To evaluate 5-HT2AR agonisms in vivo, HTR was measured in mice treated with a control and test compounds over a fixed window of time post-administration. All experiments were approved by the University of Calgary Animal Care and Use Committee in accordance with Canadian Council on Animal Care guidelines. Briefly, 8-week old C57BL/6-Elite male and female mice were obtained from Charles River. Prior to compound administration, all mice were group-housed, then single-housed on a 12:12 h light/dark schedule (lights on at 07:00 hours) with ad libitum access to food and water. Before any behavioral screening, mice were handled and exposed to the testing chamber for at least 5 min each day for three successive days and habituated to the experimental room 1 h before testing. The testing chamber was cleaned with a 70% ethanol solution between experiments. Control and test compounds, which were prepared at stock concentrations of 100 mM in DMSO, were diluted in sterile saline solution (0.9% NaCl). Prior to drug administration, mice were video monitored for 30 minutes in a plexiglass testing chamber (25.5×12.5×12.5 cm [L×W×H]) to allow for acclimation to the testing environment and to examine pre-drug spontaneous HTRs. After 30 minutes, compounds were administered via intraperitoneal (i.p.) injection at 1 mg/kg and mice were video monitored for 30 minutes then returned to their home cage. HTR analysis was conducted by an individual blinded to the subject treatment group using Behavioral Observation Research Interactive Software (BORIS, version 7, DOI: 10.1111/2041-210X.12584). Pre-drug behavior was examined during the 15-to-30-minute window prior to drug administration. Post-drug behavior was analyzed during the 15-to-30-minute window following drug administration. HTR associated with i.p. administration of psilocybin was included as a positive control measure. HTR associated with i.p. administration of vehicle (0.9% NaCl) was included as a negative control measure. Elevated incidences of HTR within the defined period of monitoring was observed in (1) psilocybin-treated mice, and (2) those treated with compound E(VI), relative to control mice treated with i.p. injected vehicle (0.9% NaCl). These results are illustrated in FIG. 3P, wherein vehicle is designated "veh," psilocybin is designated "PCB," compound with formula E(VI) is designated "E-VI," pre-drug data is designated "pre-", and post-drug data is designated "pro-." Each replicate mouse is shown as a black dot along the corresponding vertical bars (N=2-6 per compound).

Mouse Pharmacokinetic (PK) Evaluation of Drug Metabolism to Psilocin.

Prodrugs are molecules with little or no pharmacological activity in their own right but have a built in structural lability, whether by chance or by design, that permits bioconversion in vivo. Psilocybin was recognized as a natural prodrug of the active agent psilocin shortly after the identification and chemical synthesis of the former compound in 1957 (Coppola et al., 2022 J Xenobiot. 12: 41-52).

To further explore the potential of novel $C_4$-carboxylic acid-substituted tryptamine derivatives for use as psilocin prodrugs, a mouse PK study was performed. The aim of this study was to evaluate the time-dependent, in vivo conversion of novel derivative ("parent molecule") to active psilocin metabolite. Specifically, the study was conducted using both PO (per os, by mouth) and IV (intravenous) dosing. Briefly, the procedure was as follows. For every compound (i.e., parent molecule), N=12 male C57Bl/6 mice were administered a single IV does (1 mg/kg) or a single oral dose (1, 3, or 10 mg/kg), with N=3 mice per dose group. Serial blood sampling via tail snip was performed at 8 time points up to 24 hours post-dosing. Samples were collected in $K_2$EDTA tubes, plasma was separated, and all samples were frozen until bioanalysis for parent compound and psilocin metabolite. Psilocybin was also assessed as a parent compound using this same protocol to establish a control benchmark PK profile. LC-MS/MS methodology was developed for (1) each parent compound, and (2) psilocin metabolite, using a 6-8 point calibration curve in singlet (75% of standards within +/−25% accuracy (+/−25% LLOQ)). Sample processing and analysis included 96 plasma and 4 dosing solutions per compound, with two calibration curves bracketing the sample batch. Nominal analyte concentrations were calculated for dosing solutions based on the quantity of weighed analyte dissolved in exact volume of dosing solution. However, to account for any analyte instability or other confounding factors, dosing solutions were sampled by LC-MS immediately prior to animal administration to obtain "measured" analyte quantity. Measured dose was considered the same as nominal dose when the formulation concentration was within 20% of nominal concentration. However, if the measured dose was outside this window, this new "measured" dose was used in all calculations. Each mouse was designated its own number (e.g., M01, M02 . . . ). Calculated values were as follows: $T_{max}$ is the time at which maximum analyte concentration was observed; $C_{max}$ is the maximum observed concentration; Apparent $t_{1/2}$ is the apparent terminal half-life; $AUC_{0-tlast}$ is the area under the "concentration versus time curve" from time zero to the time of the last measurable concentration; $AUC_{0-int}$ is the area under the "concentration versus time curve" from time zero to infinity; $MRT_{0-inf}$ is the mean residence time from time zero to infinity; $V_{ss}$ is the steady-state volume of distribution; F (%) is bioavailability= $(Dose^{iv}*AUCP^{po})/(Dose^{po}*AUC^{iv})*100$. SD signifies significant deviation with N=3 unless indicated otherwise. A further detailed description of the methodology that was used to perform the foregoing mouse PK study can be found at: https://intervivo.com/pk-safety-studies/#pk-bridge; accessed Jul. 19, 2022.

Figure 3Q:
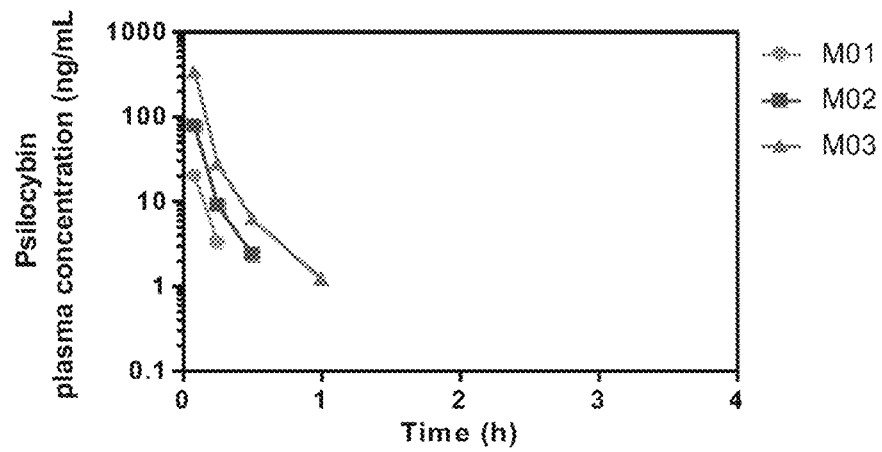
Figure 3R:
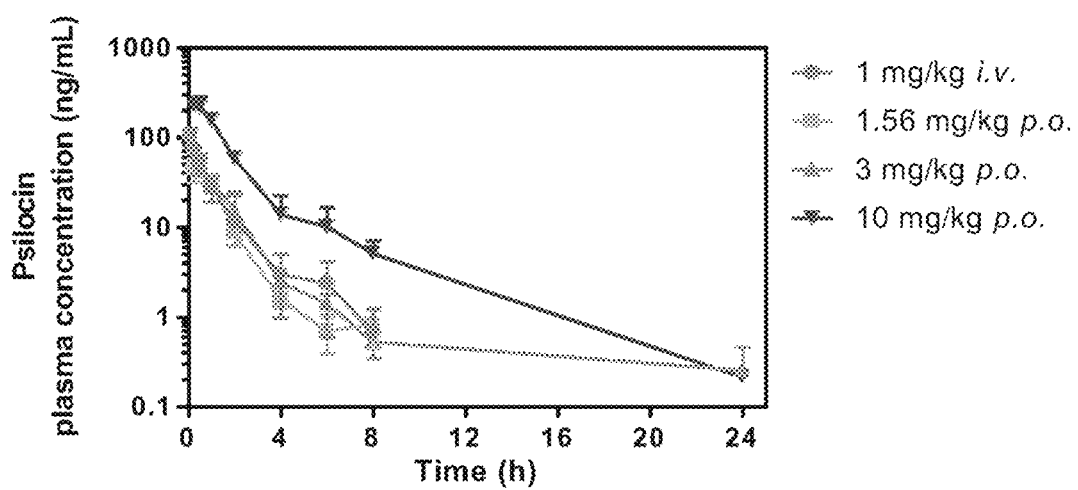

Results for psilocybin PK following psilocybin administration are found in Tables 1A-1B, and FIG. 3Q. Notably, psilocybin was only detectable in i.v. administered animals; conversely, it was not detectable in orally administered animals at any dose, suggesting a degree of instability and/or quick conversion to psilocin. Results for psilocin PK following psilocybin administration are found in Tables 2A-2B (1 mg/kg IV dose), Tables 3A-3B (1 mg/kg oral dose), Tables 4A-4B (3 mg/kg oral dose), Tables 5A, B (10 mg/kg oral dose), Table 6 (psilocin exposure) and FIG. 3R.

TABLE 1A

Plasma concentrations of psilocybin following 1 mg/kg i.v. administration of psilocybin.

| Experimental | Plasma concentration (ng/mL) | | | |
|---|---|---|---|---|
| time (h) | M01 | M02 | M03 | Mean ± SD |
| 0.0833 | 19.7 | 76.8 | 334 | 144 ± 167 |
| 0.25 | 3.32 | 8.95 | 27.2 | 13.2 ± 12.5 |
| 0.5 | No Peak | 2.35 | 6.21 | 4.28 (n = 2) |
| 1 | No Peak | No Peak | 1.21 | 1.21 (n = 1) |
| 2 | No Peak | No Peak | No Peak | n/a |

TABLE 1A-continued

Plasma concentrations of psilocybin following 1 mg/kg i.v. administration of psilocybin.

| Experimental time (h) | Plasma concentration (ng/mL) | | | |
|---|---|---|---|---|
| | M01 | M02 | M03 | Mean ± SD |
| 4 | No Peak | No Peak | No Peak | n/a |
| 6 | No Peak | No Peak | No Peak | n/a |
| 8 | No Peak | No Peak | 2.54 | n/a |

'No Peak' denotes no detectable compound by LC-MS; n/a denotes not applicable.
Bolded value was considered an outlier and not included in calculations.

TABLE 1B

Summary of plasma PK parameters for psilocybin following 1 mg/kg i.v. administration of psilocybin

| | Parameter estimate for each animal | | | |
|---|---|---|---|---|
| Parameter | M01 | M02 | M03 | Mean ± SD |
| $t_{max}$ (h) | 0.0833 | 0.0833 | 0.0833 | 0.0833 ± 0.00 |
| $C_{max}$ (ng/mL) | 19.7 | 76.8 | 334 | 144 ± 167 |

TABLE 2A

Plasma concentrations of psilocin following 1 mg/kg i.v. administration of psilocybin.

| Experimental time (h) | Plasma concentration (ng/mL) | | | |
|---|---|---|---|---|
| | M01 | M02 | M03 | Mean ± SD |
| 0.0833 | 76.5 | 106 | 124 | 102 ± 24.0 |
| 0.25 | 84.5 | 61.3 | 73.5 | 73.1 ± 11.6 |
| 0.5 | 43.6 | 43.5 | 62.4 | 49.8 ± 10.9 |
| 1 | 36.7 | 25.5 | 20.5 | 27.6 ± 8.30 |
| 2 | 5.16 | 26.9 | 3.16 | 11.7 ± 13.2 |
| 4 | 1.98 | 5.36 | 1.70 | 3.01 ± 2.04 |
| 6 | 4.33 | 2.01 | 0.810 | 2.38 ± 1.79 |
| 8 | 0.439 | 0.250 | 1.32 | 0.670 ± 0.571 |

TABLE 2B

Summary of plasma PK parameters for psilocin, following 1 mg/kg i.v. administration of psilocybin[a].

| | Parameter estimate for each animal | | | |
|---|---|---|---|---|
| Parameter | M01 | M02 | M03 | Mean ± SD |
| $t_{max}$ (h) | 0.250 | 0.0833 | 0.0833 | 0.139 ± 0.0962 |
| $C_{max}$ (ng/mL) | 84.5 | 106 | 124 | 105 ± 19.8 |
| $C_{max}$/Dose[a] (kg*ng/mL/mg) | 84.5 | 106 | 124 | 105 ± 19.8 |
| Apparent $t_{1/2}$ (h) | nc[b] | 0.905 | nc | 0.905 (n = 1) |
| $AUC_{0-tlast}$ (h*ng/mL) | 84.5 | 109 | 75.5 | 89.8 ± 17.5 |
| $AUC_{0-tlast}$/Dose[a] (h*kg*ng/mL/mg) | 84.5 | 109 | 75.5 | 89.8 ± 17.5 |
| $AUC_{0-inf}$ (h*ng/mL) | n/a[c] | 110 | n/a | 110 (n = 1) |
| $MRT_{0-inf}$ (h) | n/a | 1.64 | n/a | 1.64 (n = 1) |

[a]Psilocybin dose was used.
[b]nc denotes not calculable as the terminal phase is not well defined.
[c]n/a denotes not applicable.

TABLE 3A

Plasma concentrations of psilocin following 1.56 mg/kg oral administration of psilocybin

| Experimental time (h) | Plasma concentration (ng/mL) | | | |
|---|---|---|---|---|
| | M04 | M05 | M06 | Mean ± SD |
| 0.25 | 50.2 | 53.8 | 29.6 | 44.5 ± 13.1 |
| 0.5 | 40.5 | 52.5 | 57.2 | 50.1 ± 8.61 |
| 1 | 26.8 | 31.2 | 37.9 | 32.0 ± 5.59 |
| 2 | 11.3 | 7.04 | 7.50 | 8.61 ± 2.34 |
| 4 | 1.64 | 1.86 | 1.25 | 1.58 ± 0.309 |
| 6 | 0.445 | 1.05 | 0.611 | 0.702 ± 0.313 |
| 8 | 1.24 | 0.511 | 0.738 | 0.830 ± 0.373 |
| 24 | BLQ | BLQ | BLQ | n/a |

BLQ denotes below the lower limit of quantitation (0.2 ng/mL).
n/a denotes not applicable.

TABLE 3B

Summary of plasma PK parameters for psilocin, following 1.56 mg/kg oral administration of psilocybin[a].

| | Parameter estimate for each animal | | | |
|---|---|---|---|---|
| Parameter | M04 | M05 | M06 | Mean ± SD |
| $t_{max}$ (h) | 0.250 | 0.250 | 0.500 | 0.333 ± 0.144 |
| $C_{max}$ (ng/mL) | 50.2 | 53.8 | 57.2 | 53.7 ± 3.50 |
| $C_{max}$/Dose[a] (kg*ng/mL/mg) | 32.2 | 34.5 | 36.7 | 34.4 ± 2.24 |
| Apparent $t_{1/2}$ (h) | nc[b] | 2.15[c] | nc | 2.15 (n = 1) |
| $AUC_{0-tlast}$ (h*ng/mL) | 65.6 | 68.8 | 66.9 | 67.1 ± 1.61 |
| $AUC_{0-tlast}$/Dose[a] (h*kg*ng/mL/mg) | 42.1 | 44.1 | 42.9 | 43.0 ± 1.03 |
| $AUC_{0-inf}$ (h*ng/mL) | n/a[d] | 70.4 | n/a | 70.4 (n = 1) |
| $MRT_{0-inf}$ (h) | n/a | 1.53 | n/a | 1.53 (n = 1) |

[a]Administered dose of psilocybin (1.56 mg/kg) was used.
[b]nc denotes not calculable as the terminal phase is not well defined.
[c]Apparent $t_{1/2}$ estimate may not be accurate; sampling interval during the terminal phase <2 × $t_{1/2}$.
[d]n/a denotes not applicable.

TABLE 4A

Plasma concentrations of psilocin following 3 mg/kg oral administration of psilocybin.

| Experimental time (h) | Plasma concentration (ng/mL) | | | |
|---|---|---|---|---|
| | M07 | M08 | M09 | Mean ± SD |
| 0.25 | 52.6 | 53.0 | 41.5 | 49.0 ± 6.53 |
| 0.5 | 55.3 | 62.0 | 35.0 | 50.8 ± 14.1 |
| 1 | 23.2 | 35.5 | 36.2 | 31.6 ± 7.31 |
| 2 | 13.1 | 10.5 | 23.2 | 15.6 ± 6.71 |
| 4 | 2.28 | 1.93 | 3.16 | 2.46 ± 0.634 |
| 6 | 1.43 | 1.04 | 1.79 | 1.42 ± 0.375 |
| 8 | 0.734 | 0.368 | 0.493 | 0.532 ± 0.186 |
| 24 | BLQ | *0.111* | 0.402 | 0.257 (n = 2) |

BLQ denotes below the lower limit of quantitation (0.2 ng/mL).
Value in italics is below the lower limit of quantitation (BLQ, 0.2 ng/mL) but was included in calculations.

TABLE 4B

Summary of plasma PK parameters for psilocin, following 3 mg/kg oral administration of psilocybin[a].

| Parameter | Parameter estimate for each animal | | | |
|---|---|---|---|---|
| | M07 | M08 | M09 | Mean ± SD |
| $t_{max}$ (h) | 0.500 | 0.500 | 0.250 | 0.417 ± 0.144 |
| $C_{max}$ (ng/mL) | 55.3 | 62.0 | 41.5 | 52.9 ± 10.5 |
| $C_{max}$/Dose[a] (kg*ng/mL/mg) | 18.4 | 20.7 | 13.8 | 17.6 ± 3.48 |
| Apparent $t_{1/2}$ (h)[b] | 2.45 | 6.58 | nc[c] | 4.51 (n = 2) |
| $AUC_{0-tlast}$ (h*ng/mL) | 74.3 | 83.0 | 95.8 | 84.4 ± 10.8 |
| $AUC_{0-tlast}$/Dose[a] (h*kg*ng/mL/mg) | 24.8 | 27.7 | 31.9 | 28.1 ± 3.61 |
| $AUC_{0-inf}$ (h*ng/mL) | 76.9 | 84.1 | n/a[d] | 80.5 (n = 2) |
| $MRT_{0-inf}$ (h) | 1.84 | 2.24 | n/a | 2.04 (n = 2) |

[a] Psilocybin dose was used.
[b] For M07, apparent $t_{1/2}$ estimate may not be accurate; sampling interval during the terminal phase <2 × $t_{1/2}$.
[c] nc denotes not calculable as the terminal phase is not well defined.
[d] n/a denotes not applicable.

TABLE 5A

Plasma concentrations of psilocin following 10 mg/kg oral administration of psilocybin.

| Experimental time (h) | Plasma concentration (ng/mL) | | | |
|---|---|---|---|---|
| | M10 | M11 | M12 | Mean ± SD |
| 0.25 | 238 | 234 | 202 | 225 ± 19.7 |
| 0.5 | 202 | 289 | 156 | 216 ± 67.5 |
| 1 | 145 | 156 | 166 | 156 ± 10.5 |
| 2 | 53.9 | 54.7 | 66.6 | 58.4 ± 7.11 |
| 4 | 8.32 | 23.5 | 10.2 | 14.0 ± 8.28 |
| 6 | 3.51 | 16.8 | 10.3 | 10.2 ± 6.65 |
| 8 | 3.13 | 5.18 | 7.06 | 5.12 ± 1.97 |
| 24 | 0.258 | 0.201 | *0.186* | 0.215 ± 0.0380 |

BLQ denotes below the lower limit of quantitation (0.2 ng/mL).
Value in italics is below the lower limit of quantitation (BLQ, 0.2 ng/mL) but was included in calculations.

TABLE 5B

Summary of plasma PK parameters for psilocin following 10 mg/kg oral administration of psilocybin[a].

| Parameter | Parameter estimate for each animal | | | |
|---|---|---|---|---|
| | M10 | M11 | M12 | Mean ± SD |
| $t_{max}$ (h) | 0.250 | 0.500 | 0.250 | 0.333 ± 0.144 |
| $C_{max}$ (ng/mL) | 238 | 289 | 202 | 243 ± 43.7 |
| $C_{max}$/Dose[a] (kg*ng/mL/mg) | 23.8 | 28.9 | 20.2 | 24.3 ± 4.37 |
| Apparent $t_{1/2}$ (h) | 4.64 | 3.02 | 3.09 | 3.58 ± 0.920 |
| $AUC_{0-tlast}$ (h*ng/mL) | 348 | 457 | 387 | 397 ± 55.5 |
| $AUC_{0-tlast}$/Dose[a] (h*kg*ng/mL/mg) | 34.8 | 45.7 | 38.7 | 39.7 ± 5.55 |
| $AUC_{0-inf}$ (h*ng/mL) | 349 | 458 | 388 | 398 ± 55.1 |
| $MRT_{0-inf}$ (h) | 2.14 | 2.44 | 2.60 | 2.39 ± 0.236 |

[a] Psilocybin dose was used.

TABLE 6

Summary of mean plasma exposure of psilocin as a function of psilocybin dose.

| Parameter | Psilocybin dose | | | |
|---|---|---|---|---|
| | 1 mg/kg i.v. | 1.56 mg/kg p.o. | 3 mg/kg p.o. | 10 mg/kg p.o. |
| $C_{max}$/Dose[a] (kg*ng/mL/mg) | 105 ± 19.8 | 34.4 ± 2.24 | 17.6 ± 3.48 | 24.3 ± 4.37 |
| Apparent $t_{1/2}$ (h) | 0.905 (n = 1) | 2.15 (n = 1) | 4.51 (n = 2) | 3.58 ± 0.920 |
| $AUC_{0-tlast}$/Dose[a] (h*kg*ng/mL/mg) | 89.8 ± 17.5 | 43.0 ± 1.03 | 28.1 ± 3.61 | 39.7 ± 5.55 |

Results for compound E(VI) PK following E(VI) administration are found in Tables 7A and 7B. Notably, only plasma from animals intravenously administered E(VI) revealed detectable levels of E(VI). Conversely, plasma from animals orally administered E(VI) did not yield any detectable levels of E(VI). As seen in Tables 7A and 7B, mean E(VI) plasma concentrations were associated with relatively high standard deviations (SD), perhaps resulting from difficulties in quantitation (see Table 7A notes).

TABLE 7A

Plasma concentrations of E(VI) following 1 mg/kg i.v. administration of E(VI).

| Experimental time (h) | Plasma concentration (ng/mL)[a] | | | |
|---|---|---|---|---|
| | M13 | M14 | M15 | Mean ± SD |
| 0.0833 | 3.20 | 59.0 | 11.1 | 24.4 ± 30.2 |
| 0.25 | 72.1 | 110 | 7.79 | 63.3 ± 51.7 |
| 0.5 | 13.1 | 9.29 | 1.03 | 7.81 ± 6.17 |
| 1 | 3.14 | 5.84 | No Peak | 4.49 (n = 2) |
| 2 | *0.776* | *0.594* | No Peak | 0.685 (n = 2) |
| 4 | BLQ | BLQ | No Peak | n/a |
| 6 | No Peak | BLQ | No Peak | n/a |
| 8 | No Peak | No Peak | No Peak | n/a |

[a] freshly spiked calibration curve was used for quantification as E(VI) is not stable in plasma; concentrations are not considered accurate.
Values in italics are below the lower limit of quantitation (BLQ, 1 ng/mL) but were included in calculations.
BLQ denotes below the lower limit of quantitation (1 ng/mL).
n/a denotes not applicable.

TABLE 7B

Summary of plasma PK parameters for E(VI) following 1 mg/kg i.v. administration of E(VI).

| Parameter | Parameter estimate for each animal | | | |
|---|---|---|---|---|
| | M13 | M14 | M15 | Mean ± SD |
| $C_0$ (ng/mL) | 3.20 | 59.0 | 13.2 | 25.1 ± 29.7 |
| Apparent $t_{1/2}$ (h) | 0.382 | 0.365 | nc[a] | 0.374 ± 0.0118 |
| $AUC_{0\text{-}tlast}$ (h*ng/mL) | 20.4 | 35.2 | 3.40 | 19.7 ± 15.9 |
| $AUC_{0\text{-}tlast}$/Dose (h*kg*ng/mL/mg) | 20.4 | 35.2 | 3.40 | 19.7 ± 15.9 |
| $AUC_{0\text{-}inf}$ (h*ng/mL) | 20.8 | 35.5 | n/a[b] | 28.2 (n = 2) |
| CL (mL/h/kg) | 48084 | 28159 | n/a | 38100 (n = 2) |
| $MRT_{0\text{-}inf}$ (h) | 0.497 | 0.360 | n/a | 0.429 (n = 2) |
| $V_{ss}$ (mL/kg) | 23899 | 10146 | n/a | 17000 (n = 2) |

[a] n/c denotes not calculable as terminal phase is not well defined.
[b] n/a denotes not applicable.

Figure 3S:
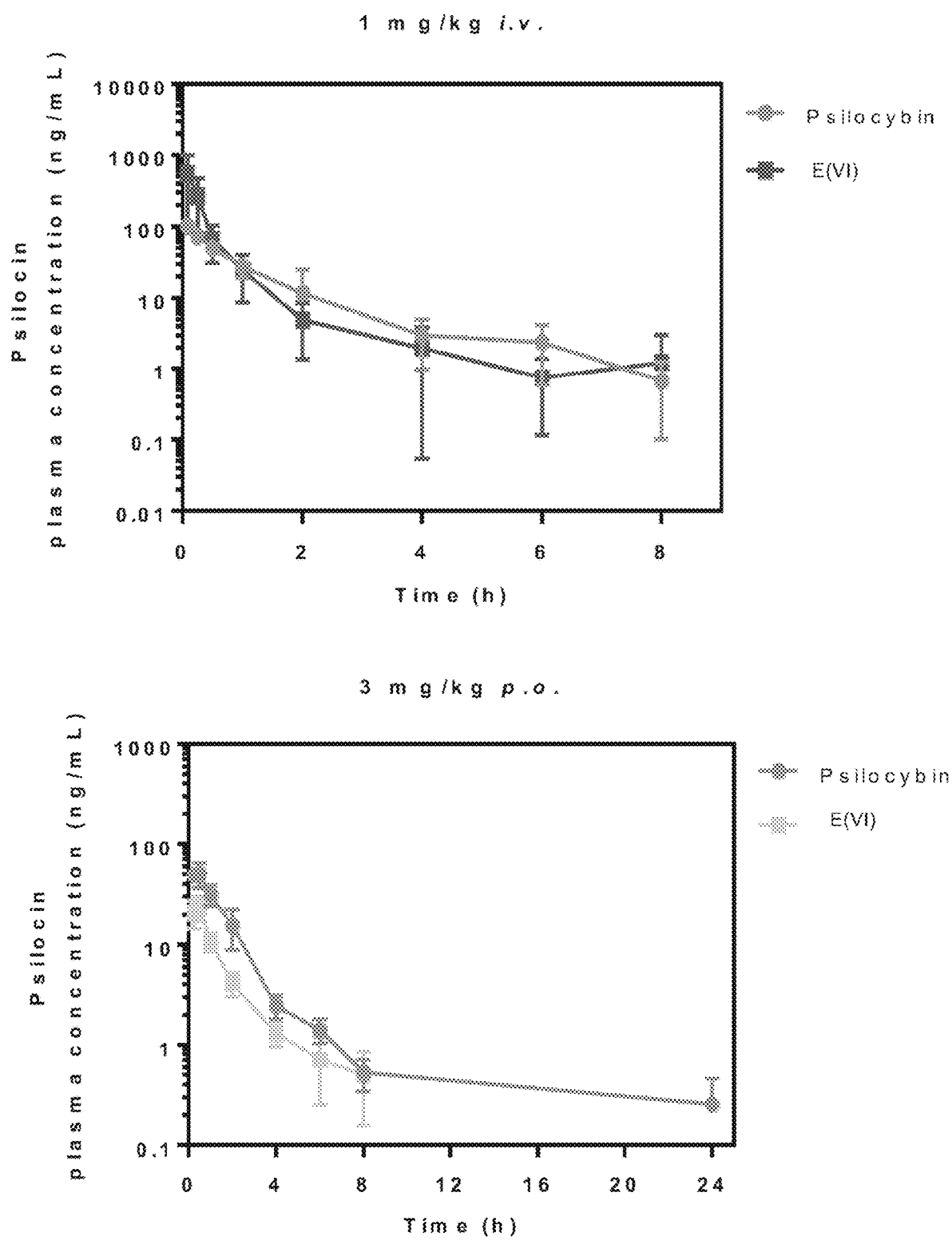

Results for psilocin PK following E(VI) administration are found in Tables 8A-8B (1 mg/kg IV dose), Tables 9A-9B (1 mg/kg oral dose), Tables 10A-10B (3 mg/kg oral dose), Tables 11A-11B (10 mg/kg oral dose), Table 12 (comparative summary for IV data), Table 13 (comparative summary for oral data), Table 14 (psilocin exposure) and FIGS. 3S (i) and 3S (ii).

TABLE 8A

Plasma concentrations of psilocin following 1 mg/kg i.v. administration of E(VI).

| Experimental time (h) | M13 | M14 | M15 | Mean ± SD |
|---|---|---|---|---|
| 0.0833 | 732 | 882 | 47.4 | 554 ± 445 |
| 0.25 | 408 | 363 | 41.0 | 271 ± 200 |
| 0.5 | 82.6 | 91.7 | 25.8 | 66.7 ± 35.7 |
| 1 | 31.4 | 36.3 | 6.56 | 24.8 ± 15.9 |
| 2 | 8.50 | 5.03 | 1.31 | 4.95 ± 3.60 |
| 4 | 4.07 | 1.53 | 0.313 | 1.97 ± 1.92 |
| 6 | 0.712 | 1.38 | *0.132* | 0.741 ± 0.625 |
| 8 | *0.160* | 3.32 | *0.136* | 1.21 ± 1.83 |

Values in italics are below the lower limit of quantitation (BLQ, 0.2 ng/mL) but were included in calculations.

TABLE 8B

Summary of plasma PK parameters for Psilocin following 1 mg/kg i.v. administration of MM590 (Group 5).

| Parameter | Parameter estimate for each animal | | | |
|---|---|---|---|---|
| | M13 | M14 | M15 | Mean ± SD |
| $t_{max}$ (h) | 0.0833 | 0.0833 | 0.0833 | 0.0833 ± 0.00 |
| $C_{max}$ (ng/mL) | 732 | 882 | 47.4 | 554 ± 445 |
| $C_{max}$/Dose[a] (kg*ng/mL/mg) | 732 | 882 | 47.4 | 554 ± 445 |
| Apparent $t_{1/2}$ (h) | 0.857 | nc[b] | 1.81 | 1.33 (n = 2) |
| $AUC_{0\text{-}tlast}$ (h*ng/mL) | 234 | 243 | 29.9 | 169 ± 121 |
| $AUC_{0\text{-}tlast}$/Dose[a] (h*kg*ng/mL/mg) | 234 | 243 | 29.9 | 169 ± 121 |
| $AUC_{0\text{-}inf}$ (h*ng/mL) | 235 | n/a[b] | 30.3 | 132 (n = 2) |
| $MRT_{0\text{-}inf}$ (h) | 0.586 | n/a | 0.835 | 0.711 (n = 2) |

[a] MM590 dose was used.
[b] n/c denotes not calculable as terminal phase is not well defined.
[c] n/a denotes not applicable.

TABLE 9A

Plasma concentrations of psilocin following 1 mg/kg oral administration of E(VI).

| Experimental time (h) | Plasma concentration (ng/mL) | | | |
|---|---|---|---|---|
| | M16 | M17 | M18 | Mean ± SD |
| 0.25 | 8.32 | 5.06 | 6.75 | 6.71 ± 1.63 |
| 0.5 | 4.64 | 5.14 | 5.91 | 5.23 ± 0.640 |
| 1 | 3.64 | 3.66 | 2.60 | 3.30 ± 0.606 |
| 2 | 1.56 | 2.52 | 1.75 | 1.94 ± 0.508 |
| 4 | 0.752 | 0.466 | 0.608 | 0.609 ± 0.143 |
| 6 | 0.348 | *0.183* | 0.767 | 0.433 ± 0.301 |
| 8 | *0.149* | BLQ | 0.227 | 0.188 (n = 2) |
| 24 | No Peak | No Peak | No Peak | n/a |

BLQ denotes below the lower limit of quantitation (0.2 ng/mL).
Values in italics are below the lower limit of quantitation (BLQ, 0.2 ng/mL) but were included in calculations.
n/a denotes not applicable.

TABLE 9B

Summary of plasma PK parameters for psilocin following 1 mg/kg oral administration of E(VI).

| Parameter | Parameter estimate for each animal | | | |
|---|---|---|---|---|
| | M16 | M17 | M18 | Mean ± SD |
| $t_{max}$ (h) | 0.250 | 0.500 | 0.250 | 0.333 ± 0.144 |
| $C_{max}$ (ng/mL) | 8.32 | 5.14 | 6.75 | 6.74 ± 1.59 |
| $C_{max}$/Dose[a] (kg*ng/mL/mg) | 8.32 | 5.14 | 6.75 | 6.74 ± 1.59 |
| Apparent $t_{1/2}$ (h) | 1.71 | 1.06 | 2.21 | 1.66 ± 0.577 |
| $AUC_{0\text{-}tlast}$ (h*ng/mL) | 10.9 | 10.2 | 11.0 | 10.7 ± 0.442 |
| $AUC_{0\text{-}tlast}$/Dose[a] (h*kg*ng/mL/mg) | 10.9 | 10.2 | 11.0 | 10.7 ± 0.442 |
| $AUC_{0\text{-}inf}$ (h*ng/mL) | 11.2 | 10.5 | 11.7 | 11.1 ± 0.641 |
| $MRT_{0\text{-}inf}$ (h) | 2.18 | 1.76 | 2.78 | 2.24 ± 0.515 |

[a] MM590 dose was used.

TABLE 10A

Plasma concentrations of psilocin following 3 mg/kg oral administration of E(VI).

| Experimental time (h) | Plasma concentration (ng/mL) | | | |
|---|---|---|---|---|
| | M19 | M20 | M21 | Mean ± SD |
| 0.25 | 25.7 | 13.5 | 23.3 | 20.8 ± 6.46 |
| 0.5 | 30.5 | 22.6 | 18.0 | 23.7 ± 6.32 |
| 1 | 13.2 | 11.0 | 8.57 | 10.9 ± 2.32 |
| 2 | 3.39 | 5.39 | 3.60 | 4.13 ± 1.10 |
| 4 | 1.02 | 1.21 | 1.70 | 1.31 ± 0.351 |
| 6 | 0.233 | 0.763 | 1.16 | 0.719 ± 0.465 |
| 8 | *0.152* | 0.512 | 0.844 | 0.503 ± 0.346 |
| 24 | No Peak | BLQ | No Peak | n/a |

BLQ denotes below the lower limit of quantitation (0.2 ng/mL).
Value in italics is below the lower limit of quantitation (BLQ, 0.2 ng/mL) but was included in calculations.
n/a denotes not applicable.

TABLE 10B

Summary of plasma PK parameters for psilocin following 3 mg/kg oral administration of E(VI).

| | Parameter estimate for each animal | | | |
|---|---|---|---|---|
| Parameter | M19 | M20 | M21 | Mean ± SD |
| $t_{max}$ (h) | 0.500 | 0.500 | 0.250 | 0.417 ± 0.144 |
| $C_{max}$ (ng/mL) | 30.5 | 22.6 | 23.3 | 25.5 ± 4.37 |
| $C_{max}$/Dose[a] (kg*ng/mL/mg) | 10.2 | 7.53 | 7.77 | 8.49 ± 1.46 |
| Apparent $t_{1/2}$ (h)[b] | 1.28 | 1.84 | 2.93 | 2.02 ± 0.836 |
| $AUC_{0-tlast}$ (h*ng/mL) | 33.2 | 30.9 | 30.0 | 31.4 ± 1.63 |
| $AUC_{0-tlast}$/Dose[a] (h*kg*ng/mL/mg) | 11.1 | 10.3 | 10.0 | 10.5 ± 0.544 |
| $AUC_{0-inf}$ (h*ng/mL) | 33.5 | 33.3 | 34.8 | 33.9 ± 0.835 |
| $MRT_{0-inf}$ (h) | 1.27 | 2.09 | 3.02 | 2.13 ± 0.874 |

[a] MM590 dose was used.
[b] For M20 and M21, apparent $t_{1/2}$ estimate may not be accurate; sampling interval during the terminal phase <2 × $t_{1/2}$.

TABLE 11A

Plasma concentrations of psilocin following 10 mg/kg oral administration of E(VI).

| Experimental | Plasma concentration (ng/mL) | | | |
|---|---|---|---|---|
| time (h) | M22 | M23 | M24 | Mean ± SD |
| 0.25 | 53.8 | 34.9 | 78.6 | 55.8 ± 21.9 |
| 0.5 | 66.2 | 61.1 | 113 | 80.1 ± 28.6 |
| 1 | 41.7 | 43.6 | 45.2 | 43.5 ± 1.75 |
| 2 | 32.0 | 23.6 | 15.1 | 23.6 ± 8.45 |
| 4 | 5.58 | 4.19 | 2.62 | 4.13 ± 1.48 |
| 6 | 1.24 | 8.11 | 3.34 | 4.23 ± 3.52 |
| 8 | 0.764 | 4.19 | 4.24 | 3.06 ± 1.99 |
| 24 | BLQ | BLQ | BLQ | n/a |

BLQ denotes below the lower limit of quantitation (0.2 ng/mL).
n/a denotes not applicable.

TABLE 11B

Summary of plasma PK parameters for psilocin following 10 mg/kg oral administration of E(VI).

| | Parameter estimate for each animal | | | |
|---|---|---|---|---|
| Parameter | M22 | M23 | M24 | Mean ± SD |
| $t_{max}$ (h) | 0.500 | 0.500 | 0.500 | 0.500 ± 0.00 |
| $C_{max}$ (ng/mL) | 66.2 | 61.1 | 113 | 80.1 ± 28.6 |
| $C_{max}$/Dose[a] (kg*ng/mL/mg) | 6.62 | 6.11 | 11.3 | 8.01 ± 2.86 |
| Apparent $t_{1/2}$ (h) | 1.39 | nc[b] | nc | 1.39 (n = 1) |
| $AUC_{0-tlast}$ (h*ng/mL) | 123 | 122 | 126 | 123 ± 2.31 |
| $AUC_{0-tlast}$/Dose[a] (h*kg*ng/mL/mg) | 12.3 | 12.2 | 12.6 | 12.3 ± 0.231 |
| $AUC_{0-inf}$ (h*ng/mL) | 124 | n/a[c] | n/a | 124 (n = 1) |
| $MRT_{0-inf}$ (h) | 1.77 | n/a | n/a | 1.77 (n = 1) |

[a] MM590 dose was used.
[b] n/c denotes not calculable as terminal phase is not well defined.
[c] n/a denotes not applicable.

TABLE 12

Summary of mean plasma exposure of psilocin as a function of E(VI).

| | MM590 dose | | | |
|---|---|---|---|---|
| Parameter | 1 mg/kg i.v. | 1 mg/kg p.o. | 3 mg/kg p.o. | 10 mg/kg p.o. |
| $C_{max}$/Dose[a] (kg*ng/mL/mg) | 554 ± 445 | 6.74 ± 1.59 | 8.49 ± 1.46 | 8.01 ± 2.86 |
| Apparent $t_{1/2}$ (h) | 1.33 (n = 2) | 1.66 ± 0.577 | 2.88 ± 1.29 | 1.39 (n = 1) |
| $AUC_{0-tlast}$/Dose[a] (h*kg*ng/mL/mg) | 169 ± 121 | 10.7 ± 0.442 | 10.5 ± 0.544 | 12.3 ± 0.231 |

[a] MM590 dose.

In Vitro Survey of Pharmacological Interaction Profiles at Receptors, Transporters and Enzymes Linked to Targeted Health Conditions.

To expand pharmacological profiling to include a broader range of targets with known involvement in, or connection to, brain neurological disorders, compound E(VI) was evaluated with respect to receptor interaction (https://www.eurofinsdiscoveryservices.com/). Specifically, the cell-based screening assay panel known as "SAFETYscan E/IC150 ELECT" was used to generate data regarding interaction of derivative molecules with 20 different proteins, including 12 GPCR receptors (ADRA1A, ADRA2A, AVPR1A, CHRM1, CHRM2, CNR1, DRD1, DRD2S, HTR1A (5-HT$_{1A}$), HTR1B (5-HTR1B), HTR2B (5-HT$_{2B}$), OPRD1), 3 ion channels (GABAA, HTR3A (5-HT$_{3A}$), NMDAR), one enzyme (MAO-A), and 3 transporters (DAT, NET, SERT).

i. EFC-Based cAMP Secondary Messenger Assay.

Of the 12 GPCR proteins, 8 were assayed via a cAMP secondary messenger assay: ADRA2A, CHRM2, CNR1, DRD1, DRD2S, HTR1A, HTR1B, OPRD1. Briefly, employed a panel of cell lines stably expressing non-tagged GPCR proteins that endogenously signal through cAMP. These assays monitored the activation of a GPCR through $G_i$ or $G_s$ secondary messenger signaling in a homogenous, non-imaging assay format using a technology termed Enzyme Fragment Complementation (EFC). EFC uses β-galactosidase (β-gal) as the functional endpoint. The β-gal enzyme is split into two complementary portions: Enzyme Acceptor (EA) and Enzyme Donor (ED). In the assay, exogenously introduced ED fused to cAMP (ED-cAMP) competes with endogenously generated cAMP for binding to an anti-cAMP-specific antibody. Active β-gal is formed by complementation of exogenous EA to any unbound EDcAMP. Active enzyme can then convert a chemiluminescent substrate, generating an output signal detectable on a standard microplate reader.

These 8 cAMP-based assays were conducted in both agonist and antagonist modes, either in $G_s$ format (no forskolin) or in $G_i$ format (in the presence of $EC_{80}$ forskolin). For $G_s$ and $G_i$ agonist assays: cell media was aspirated from GPCR-containing cultures and replaced with 15 µl 2:1HBSS/1-mM HEPES:cAMP XS+Ab reagent. Five microlitres of derivative compound, prepared as a stock solution (also containing $EC_{80}$ forskolin in the case of $G_i$ format) were added to the cells at final target concentrations and pre-incubated for 30 minutes. Final assay vehicle concentration was 1%. After pre-incubation, assay signal was generated through the addition of (1) 20 µL cAMP XS+ED/CL lysis cocktail, and (2) 20 µL cAMP XS+EA reagent, allowing incubation periods of one and three hours, respectively. Antagonist assays were performed in the same manner as agonist assays, except pre-incubation entailed exposure to the test derivative (30 minutes) followed by exposure to an established agonist at $EC_{80}$ ("agonist challenge", 30 minutes). In the case of antagonist assays of $G_i$-coupled GPCRs, $EC_{80}$ forskolin was included in assay buffers.

In all 8 cAMP assays (agonist or antagonist mode), the resulting chemiluminescent signal was measured using a PerkinElmer Envision™ instrument. Compound activity was analyzed using CBIS data analysis suite (ChemInnovation, CA). Percent activity (%) was calculated according to standard procedures. For example: in $G_s$ agonist mode assays, percentage activity was calculated using the following formula: % activity=100%×[mean RLU of test derivative−mean RLU of vehicle control]/[mean RLU of control ligand−mean RLU of vehicle control]. For $G_s$ antagonist mode assays, percentage inhibition was calculated using the following formula: % inhibition=100%×[1−[mean RLU of test derivative−mean RLU of vehicle control]/[mean RLU of $EC_{80}$ control ligand−mean RLU of vehicle control]]. For $G_i$ agonist mode assays, percentage activity was calculated using the following formula: % activity=100%×[1−[mean RLU of test derivative−mean RLU of control ligand]/[mean RLU of vehicle control−mean RLU of control ligand]]. For $G_i$ antagonist or negative allosteric mode assays, percentage inhibition was calculated using the following formula: % inhibition=100%×[mean RLU of test compound−mean RLU of $EC_{80}$ control ligand]/[mean RLU of forskolin positive control−mean RLU of $EC_{80}$ control]. For primary screens, percent response was capped at 0% or 100% where calculated percent response returned a negative value or a value greater than 100, respectively. To assess assay performance and establish positive control benchmarks, ligands listed in Table 13 were evaluated alongside test derivatives. Results for EFC-based cAMP secondary messenger assays on GPCRs using compound E(VI) ligand or positive controls are shown in Table 14.

ii. Calcium Secondary Messenger Assay.

Of the 12 GPCR proteins, 4 were assayed via a calcium secondary messenger assay: ADRA1A, AVPR1A, CHRM1, HTR2B. Briefly, the Calcium No WashPLUS assay monitors GPCR activity via $G_q$ secondary messenger signaling in a live cell, non-imaging assay format. Eurofins DiscoverX employed proprietary cell lines stably expressing $G_q$-coupled GPCR proteins. Calcium mobilization was monitored using a calcium-sensitive dye loaded into cells. GPCR activation by a test or control compound resulted in the release of calcium from intracellular stores and an increase in dye fluorescence that is measured in real-time.

The four GPCR proteins assayed via calcium secondary messenger assay were surveyed in both agonist and antagonist modes. Cell lines were expanded from freezer stocks according to standard procedures, seeded into microplates and incubated at 37° C. prior to testing. Assays were performed in 1× dye loading buffer consisting of 1× dye (DiscoverX, Calcium No WashPLUS kit, Catalog No. 90-0091), 1× Additive A and 2.5 mM probenecid in HBSS/20 mM Hepes. Cells were loaded with dye prior to testing. Media was aspirated from cells and replaced with 25 µL dye loading buffer, incubated for 45 minutes at 37° C. and then 20 minutes at room temperature. For agonist determination, cells were incubated with sample compound to induce response. After dye loading, cells were removed from the incubator and 25 µL of 2× compound in HBSS/20 mM Hepes was added using a FLIPR Tetra (MDS). Compound agonist activity was measured on a FLIPR Tetra. Calcium mobilization was monitored for 2 minutes with a 5 second baseline read. For antagonist determination, cells were pre-incubated with sample compound followed by agonist challenge at the $EC_{80}$ concentration. After dye loading, cells were removed from the incubator and 25 µL 2× sample compound was added. Cells were incubated for 30 minutes at room temperature in the dark to equilibrate plate temperature. After incubation, antagonist determination was initiated with addition of 25 µL 1× derivative compound with 3×$EC_{80}$ agonist using FLIPR. Compound antagonist activity was measured on a FLIPR Tetra (MDS). Calcium mobilization was monitored for 2 minutes with a 5 second baseline read. In both agonist and antagonist modes, data analysis was initiated using FLIPR, where area under the curve was calculated for the entire two minute read. Compound activity was analyzed using CBIS data analysis suite (ChemInnovation, CA). For agonist mode assays, percentage activity was calculated using the following formula: % activity=100%×[mean RFU of test compound−mean RFU of vehicle control]/[mean RFU control ligand−mean RFU of vehicle control]. For antagonist mode assays, percentage inhibition was calculated using the following formula: % inhibition=100%×[1−[mean RFU of test compound−mean RFU of vehicle control]/[mean RFU of $EC_{80}$ control−mean RFU of vehicle control]]. For primary screens, percent response was capped at 0% or 100%, where calculated percent response returned a negative value or a value greater than 100, respectively. To assess assay performance and establish positive control benchmarks, ligands listed in Table 13 were evaluated alongside test derivatives. Results for EFC-based cAMP secondary messenger assays on GPCRs using compound E(VI) ligand or positive controls are shown in Table 14.

iii. Ion Channel Assays.

Both 'blocker' and 'opener' activities of putative ligands on three distinct ion channels (GABAA, HTR3A, NMDAR) were surveyed. Briefly, Eurofins DiscoverX was employed in conjunction with the FLIPR Membrane Potential Assay Kit (Molecular Devices) which utilizes a proprietary fluorescent indicator dye in combination with a quencher to reflect real-time membrane potential changes associated with ionchannel activation and ion transporter proteins. Unlike traditional dyes such as DiBAC, the FLIPR Membrane Potential Assay Kit detects bidirectional ion fluxes so both variable and control conditions can be monitored within a single experiment. Cell lines were expanded from freezer stocks according to standard procedures, seeded onto microplates, and incubated at 37° C. Assays were performed in 1× Dye Loading Buffer consisting of 1× Dye and 2.5 mM probenecid when applicable. Cells were loaded with dye prior to testing and incubated for 30-60 minutes at 37° C. For agonist ('Opener') assays, cells were incubated with sample (i.e., containing derivative or control compound; Table 13) to induce response as follows. Dilution of sample stocks was performed to generate 2-5× sample (i.e., containing derivative or control compound) in assay buffer. Next, 10-25 µL of 2-5× sample was added to cells and incubated at 37° C. or room temperature for 30 minutes. Antagonist ('Blocker') assays were performed using the same procedure except that after dye loading, cells were removed from the incubator and 10-25 µL 2-5× sample (i.e., containing derivative or control compound) was added to cells in the presence of $EC_{80}$ agonist. Cells were incubated for 30 minutes at room temperature in the dark to equilibrate plate temperature. Compound activity was measured on a FLIPR Tetra (Molecular Devices). Compound activity was analyzed using CBIS data analysis suite (ChemInnovation, CA). For agonist mode assays, percentage activity was calculated using the following formula: % activity=100%× [mean RLU of test derivative−mean RLU of vehicle control]/[mean control ligand−mean RLU of vehicle control]. For antagonist mode, percentage inhibition was calculated using the following formula: % inhibition=100%×[1−[mean RLU of test derivative−mean RLU of vehicle control]/[mean RLU of $EC_{80}$ control−mean RLU of vehicle control]]. For primary screens, percent response was capped at 0% or 100% where calculated percent response returned a negative value or a value greater than 100, respectively. To assess assay performance and establish positive control benchmarks, ligands listed in Table 13 were evaluated alongside test derivatives. Results for EFC-based cAMP secondary messenger assays on GPCRs using compound E(VI) ligand or positive controls are shown in Table 14.

iv. Neurotransmitter Transporter Uptake Assays.

The Neurotransmitter Transporter Uptake Assay Kit from Molecular Devices was used to examine impact of test compounds on 3 distinct transporters (DAT, NET, SERT). This kit provided a homogeneous fluorescence-based assay for the detection of dopamine, norepinephrine or serotonin transporter activity in cells expressing these transporters. The kit employed a fluorescent substrate that mimics the biogenic amine neurotransmitters that are taken into the cell through the specific transporters, resulting in increased intracellular fluorescence intensity. Cell lines were expanded from freezer stocks according to standard procedures, seeded into microplates and incubated at 37° C. prior to testing. Assays were performed in 1× Dye Loading Buffer consisting of 1× Dye, and 2.5 mM probenecid as applicable. Next, cells were loaded with dye and incubated for 30-60 minutes at 37° C. "Blocker" or antagonist format assays were performed, where cells were pre-incubated with sample (i.e., containing sample derivative or positive control compound) as follows. Dilution of sample stocks (i.e., containing sample derivative or positive control compound; Table 13) was conducted to generate 2-5× sample in assay buffer. After dye loading, cells were removed from the incubator and 10-25 µL 2-5× sample (i.e., containing sample derivative or positive control compound) was added to cells in the presence of $EC_{80}$ agonist as appropriate. Cells were incubated for 30 minutes at room temperature in the dark to equilibrate plate temperature. Compound activity was measured on a FLIPR Tetra (Molecular Devices), and activity was analyzed using CBIS data analysis suite (ChemInnovation, CA). For antagonist ('Blocker') mode, percentage inhibition was calculated using the following formula: % inhibition=100%×[1−[mean RLU of test sample−mean RLU of vehicle control]/[mean RLU of $EC_{80}$ control−mean RLU of vehicle control]]. For primary screens, percent response was capped at 0% or 100% where calculated percent response returned a negative value or a value greater than 100, respectively. To assess assay performance and establish positive control benchmarks, ligands listed in Table 13 were evaluated alongside test derivative. Results for EFC-based cAMP secondary messenger assays on GPCRs using compound E(VI) ligand or positive controls are shown in Table 14.

v. MAO-A Enzyme Assay.

For the MAO-A assay, all chemicals and enzyme preparations were sourced from Sigma. Briefly, enzyme and test compound (i.e., derivative or control compound; see Table 13) were preincubated for 15 minutes at 37° C. before substrate addition. The reaction was initiated by addition of kynuramine and incubated at 37° C. for 30 minutes. The reaction was terminated by addition of NaOH. The amount of 4-hydroquinoline formed was determined through spectrofluorimetric readout with the emission detection at 380 nm and excitation wavelength 310 nm. For each assay, microplates were transferred to a PerkinElmer Envision™ instrument for readouts as per standard procedures. Compound activity was analyzed using CBIS data analysis suite (ChemInnovation, CA). Percentage inhibition was calculated using the following formula: % inhibition=100%×[1−[mean RLU of test sample−mean RLU of vehicle control]/[mean RLU of positive control−mean RLU of vehicle control]]. For primary screens, percent response was capped at 0% or 100% where calculated percent response returned a negative value or a value greater than 100, respectively. To assess assay performance and establish positive control benchmarks, ligands listed in Table 13 were evaluated alongside test derivative. Results for EFC-based cAMP secondary messenger assays on GPCRs using compound E(VI) ligand or positive controls are shown in Table 14.

TABLE 13

Control ligands used for target assays (GPCR, G-protein coupled receptor; IC, ion channel; EN, enzyme; TR, transporter).

| Target | Assay | Type | Control ligand/modulator |
|---|---|---|---|
| ADRA1A | Agonist | GPCR | A 61603 Hydrobromide |
| ADRA1A | Antagonist | GPCR | Tamsulosin |
| ADRA2A | Agonist | GPCR | UK 14304 |
| ADRA2A | Antagonist | GPCR | Yohimbine |
| AVPR1A | Agonist | GPCR | [Arg8]-Vasopressin |
| AVPR1A | Antagonist | GPCR | SR 49059 |
| CHRM1 | Agonist | GPCR | Acetylcholine chloride |
| CHRM1 | Antagonist | GPCR | Atropine |
| CHRM2 | Agonist | GPCR | Acetylcholine chloride |
| CHRM2 | Antagonist | GPCR | Atropine |
| CNR1 | Agonist | GPCR | CP 55940 |
| CNR1 | Antagonist | GPCR | AM 251 |
| DRD1 | Agonist | GPCR | Dopamine |
| DRD1 | Antagonist | GPCR | SCH 39166 |
| DRD2S | Agonist | GPCR | Dopamine |
| DRD2S | Antagonist | GPCR | Risperidone |
| HTR1A | Agonist | GPCR | Serotonin hydrochloride |
| HTR1A | Antagonist | GPCR | Spiperone |
| HTR1B | Agonist | GPCR | Serotonin hydrochloride |
| HTR1B | Antagonist | GPCR | SB 224289 |
| HTR2B | Agonist | GPCR | Serotonin hydrochloride |
| HTR2B | Antagonist | GPCR | LY 272015 |
| OPRD1 | Agonist | GPCR | DADLE |
| OPRD1 | Antagonist | GPCR | Naltriben |
| GABAA | Opener | IC | GABA |
| GABAA | Blocker | IC | Picrotoxin |
| HTR3A | Opener | IC | Serotonin hydrochloride |
| HTR3A | Blocker | IC | Bemesetron |
| MAO-A | Inhibitor | EN | Clorgyline |
| DAT | Blocker | TR | GBR 12909 |

TABLE 13-continued

Control ligands used for target assays (GPCR, G-protein coupled receptor; IC, ion channel; EN, enzyme; TR, transporter).

| Target | Assay | Type | Control ligand/modulator |
|---|---|---|---|
| NET | Blocker | TR | Desipramine |
| SERT | Blocker | TR | Clomipramine |
| NMDAR | Blocker | IC | (+)-MK 801 |
| NMDAR | Opener | IC | L-Glutamic acid |

TABLE 14

Data summary table of target assays for compound E(VI) and control (C) ligands. Potency ($EC_{50}$ or $IC_{50}$) is provided in units of μM. AGN, agonist; ANT, antagonist; OP, opener; BL, blocker; IN, inhibitor.

| Target name | Target type | Assay type | $EC_{50}$ C | $IC_{50}$ C | $EC_{50}$ E(VI) | $IC_{50}$ E(VI) |
|---|---|---|---|---|---|---|
| ADRA1A | GPCR | AGN | 5.00E−05 | — | >100 | — |
| ADRA1A | GPCR | ANT | — | 9.60E−04 | — | 1.09 |
| ADRA2A | GPCR | AGN | 4.00E−05 | — | >100 | — |
| ADRA2A | GPCR | ANT | — | 3.10E−03 | — | 19.78 |
| AVPR1A | GPCR | AGN | 4.20E−04 | — | >100 | — |
| AVPR1A | GPCR | ANT | — | 1.60E−03 | — | >100 |
| CHRM1 | GPCR | AGN | 9.70E−03 | — | >100 | — |
| CHRM1 | GPCR | ANT | — | 6.10E−03 | — | 15.1 |
| CHRM2 | GPCR | AGN | 2.70E−02 | — | >100 | — |
| CHRM2 | GPCR | ANT | — | 3.20E−03 | — | 51.24 |
| CNR1 | GPCR | AGN | 1.00E−05 | — | >100 | — |
| CNR1 | GPCR | ANT | — | 6.20E−04 | — | 96.99 |
| DRD1 | GPCR | AGN | 9.10E−02 | — | >100 | — |
| DRD1 | GPCR | ANT | — | 7.10E−04 | — | 7.11 |
| DRD2S | GPCR | AGN | 5.10E−04 | — | >100 | — |
| DRD2S | GPCR | ANT | — | 9.60E−04 | — | 13.28 |
| HTR1A | GPCR | AGN | 1.70E−03 | — | 11.36 | — |
| HTR1A | GPCR | ANT | — | 4.60E−02 | — | >100 |
| HTR1B | GPCR | AGN | 9.00E−05 | — | 2.36E−01 | — |
| HTR1B | GPCR | ANT | — | 5.80E−03 | — | >100 |
| HTR2B | GPCR | AGN | 6.30E−04 | — | >100 | — |
| HTR2B | GPCR | ANT | — | 4.00E−04 | — | 8.57E−02 |
| OPRD1 | GPCR | AGN | 5.00E−05 | — | 28.52 | — |
| OPRD1 | GPCR | ANT | — | 5.80E−04 | — | >100 |
| GABAA | Ion channel | OP | 6.2 | — | >100 | — |
| GABAA | Ion channel | BL | — | 4.6 | — | 32.17 |
| HTR3A | Ion channel | OP | 3.00E−01 | — | >100 | — |
| HTR3A | Ion channel | BL | — | 1.90E−03 | — | 1.87 |
| MAO-A | Enzyme | IN | — | 2.90E−03 | — | >100 |
| DAT | transporter | BL | — | 1.40E−03 | — | 1 |
| NET | transporter | BL | — | 6.70E−03 | — | 9.25 |
| SERT | transporter | BL | — | 1.80E−03 | — | 9.06 |
| NMDAR | Ion channel | BL | — | 8.00E−02 | — | 15 |
| NMDAR | Ion channel | OP | 4.40E−01 | — | >100 | — |

Figure 4A:
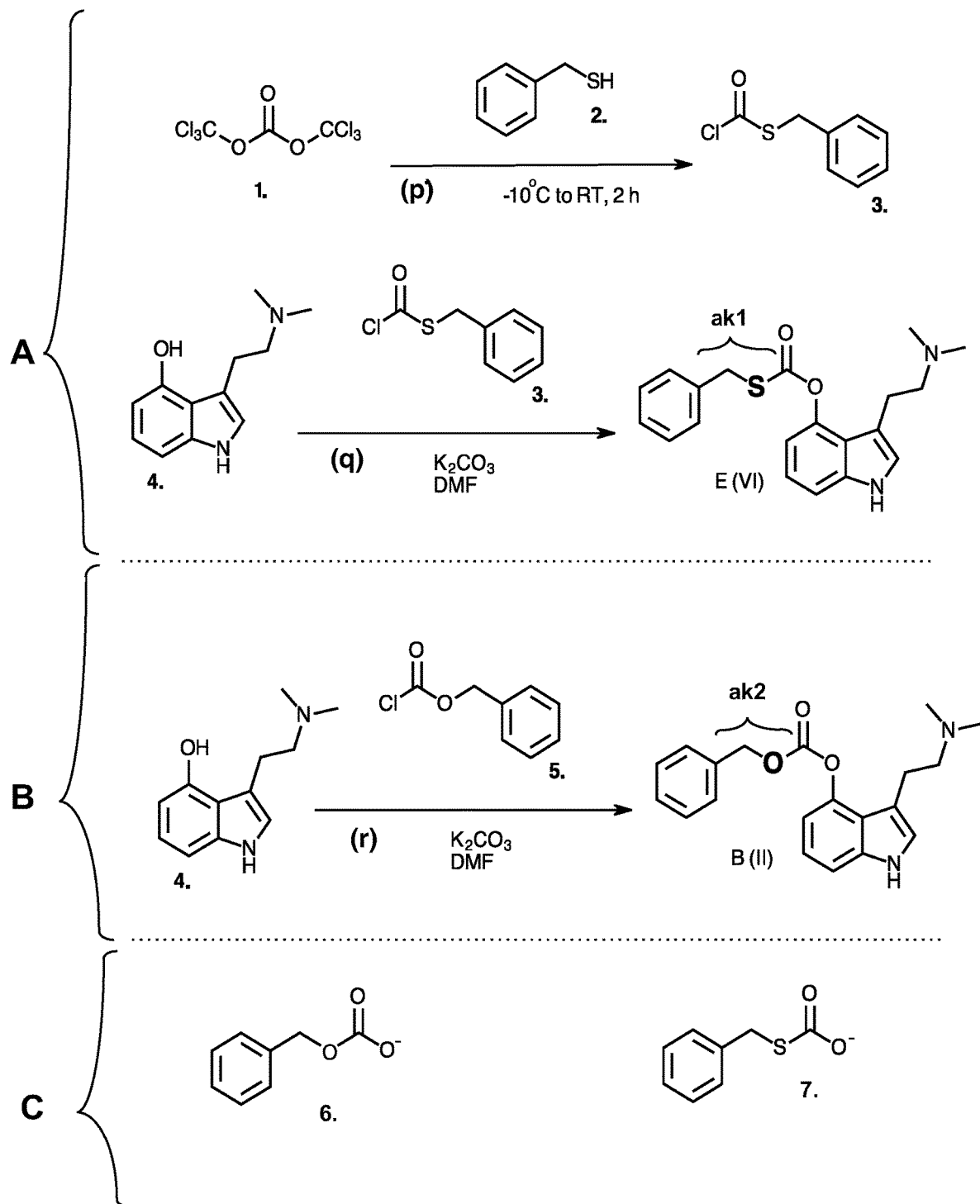
FIGS. 4A, 4B, 4C, 4D (i), 4D (ii), 4E, and 4F depict example chemical reactions to make an example chemical compound provided by the present disclosure, namely in FIG. 4A a compound having chemical formula E(VI) (Portion A, FIG. 4A); for comparative purposes, another chemical reaction and compound having chemical formula B(II) (Portion B, FIG. 4A); and chemical compounds relevant to the example chemical reactions ((Portion C, FIG. 4A)), and various graphs representing certain experimental results (FIGS. 4B-3F), notably, graphs obtained in the performance of experimental assays to evaluate the efficacy of an example compound having chemical formula B(II), notably, a competition assay for a compound with formula B(II), designated "B-II" (FIG. 4B), a cAMP assay in the presence of varying concentrations of the compound having chemical formula B(II), designated "B-II" in +5HT$_{1A}$ cells and −5HT$_{1A}$ cells with 4 µM forskolin (FIG. 4C); metabolic stability assays for a compound with formula B(II) (FIGS. 3D (i) and 3D (ii)); side-by-side metabolic stability assays for compounds with formula E(VI) and B(II), designated "E(VI)" and "B(II)", respectively (FIG. 3E); and side-by-side drug-induced Head Twitch Response (HTR) assays using the compounds having formula E(VI) and B(II), designated "E(VI)" and "B(II)", respectively (FIG. 4F).

Example 2—Comparative Evaluation of a $C_4$-Carbonothioate-Substituted Tryptamine Derivative and a $C_4$-Carbonic Ester-Substituted Tryptamine Derivative Referring to FIG. 4A (comprising figure portions: Portion A, Portion B, and Portion C), shown therein in are example chemical synthetic reactions (p), (q), (see: Portion A) and (r) (see: Portion B), and various example chemical compounds relating to the chemical synthetic reactions (p), (q), and (r) notably, compounds 1, 2, 3, 4, and E (VI) (see: Portion A); compounds 4, 5 and B(II) (see: Portion B); and compounds 6 and 7 (see: Portion C). The compound having chemical formula B(II) (see: Portion B) and the compound having chemical formula E(VI) (see: Portion A) (hereinafter referred to simply as B(II) and E(VI), respectively) can be said to be a $C_4$-carbonic ester-substituted tryptamine derivative and a $C_4$-carbonothioate-substituted tryptamine derivative, respectively. It is noted that the chemical structures of B(II) and E(VI) differ from one another on account of a single atom. In particular, whereas in the alkylene chain ak2 extending from the carboxyl moiety of the $C_4$-substituent group in B(II) a carbon atom is substituted by an oxygen atom (shown in bold font in Portion B), in E(VI) in the alkylene chain ak1 extending from the carboxyl moiety a carbon atom is substituted by a sulfur atom (shown in bold font in Portion A).

It is noted that benzylcarbonate moieties (see: Portion C, compound 6) (as possessed by B(II)) are routinely and extensively used as a protecting group for alcohols and amines in organic synthetic reactions. However, by contrast, there exists a paucity of equivalent reports using benzylthiocarbonate moieties (see: Portion C, compound 7) (as possessed by E(VI)) for this purpose.

Furthermore, once installed, a benzylcarbonate (see: Portion C, compound 6) (as possessed by B(II)) can be robustly deprotected using hydrogen gas under reductive conditions to reveal the unprotected alcohol, while a benzylthiocarbonate (see: Portion C, compound 7) (as possessed by E(VI)) may be cleaved under oxidative conditions (e.g., $H_2O_2$) or using nucleophilic fluoride (Greene's Protective Groups in Organic Synthesis, 5$^{th}$ Edition, P. G. M. Wuts, Wiley, 2014).

Furthermore, referring to Portion B in FIG. 4A, the reagent required to install a benzylcarbonate moiety in the synthesis of B(II) in accordance with synthesis reaction (r)—namely benzylchloroformate 5—is widely commercially available. By contrast, referring to Portion A in FIG.

4A, benzylchlorothioformate 3, the reagent needed to introduce a benzylthiocarbonate moiety in the synthesis of E(VI) in accordance with synthesis reaction (q), generally initially needs its own laboratory synthesis from phosgene or triphosgene 1 (see: reaction (p)), rendering its general application as a protecting group limited.

Furthermore, with respect to chemical stability, the carbonothioate 7 and carbonic ester 6 functional groups are known to display substantially different rates of hydrolysis (Pharmaceutical Research, 1993, 10, 639-648).

Furthermore, functional pharmacological attributes of B(II) and E(VI) were evaluated and will hereinafter be described.

To further compare B(II) and E(VI), B(II) was subjected to the same pharmacological assays as E(VI). The first series of assays, namely (1) cell viability assays, (2) radioligand receptor binding assays, and (3) evaluation of 5-$HT_{1A}$ receptor modulation revealed very little difference between B(II) and E(VI). Briefly, the results were as follows. First, cell viability was assessed as described for Example 1, except B(II) was evaluated in place E(VI). It was determined that cytotoxicity was relatively similar for these two compounds, with a result of $CD_{50}$=65.9 µM for B(II) and $CD_{50}$=74.5 µM for E(VI) (FIG. 3C). Second, activity at 5-$HT_{2A}$ receptor was assessed as described for Example 1, except the compound with formula B(II) was evaluated in place of the compound with formula E(VI). It was determined that 5-$HT_{2A}$ receptor binding was similar to that of E(VI), with $K_i$ values of 277 nM and 130 nM (FIG. 3G), respectively. Third, experimental procedures assessing modulation of 5-$HT_{1A}$ were performed as described in Example 1, except that compound B(II) was evaluated in place of E(VII). It was determined that neither molecule engaged 5-$HT_{1A}$ with sufficient potency to calculate an EC50 value (refer to FIG. 3H for E(VI) data).

Figure 4B:
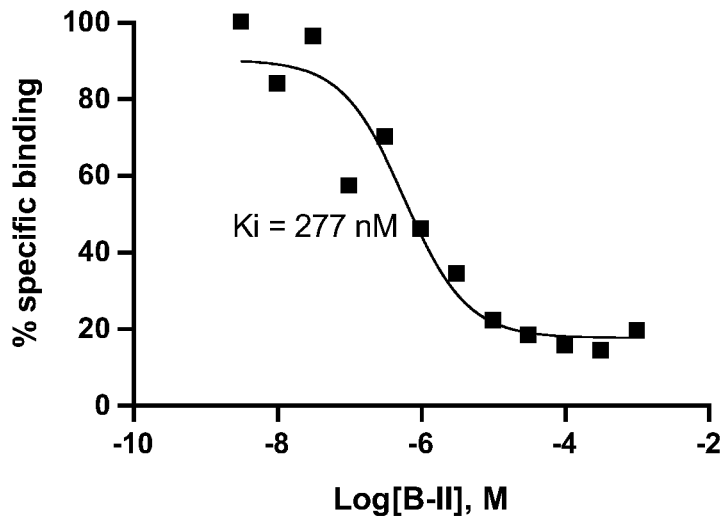
Figure 4C:
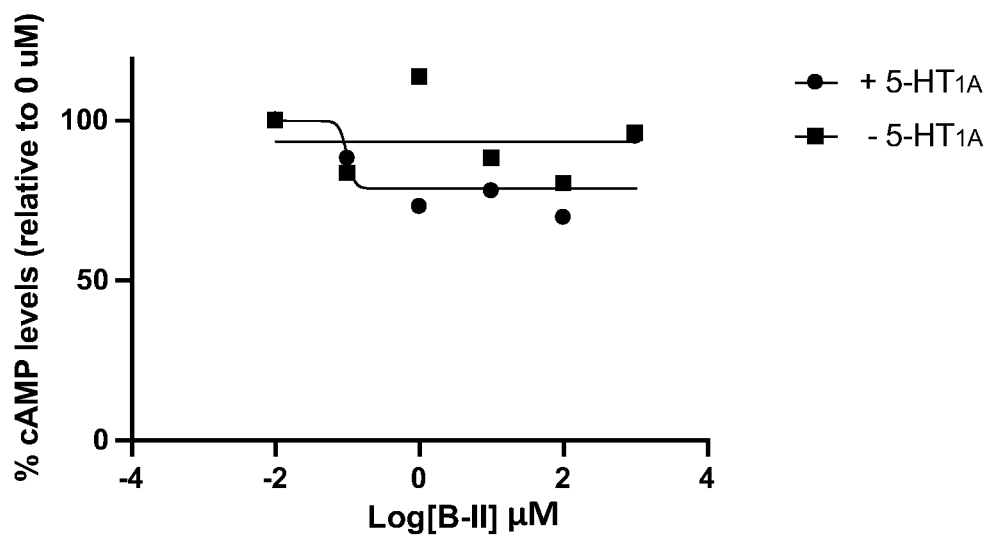
Figure 4D:
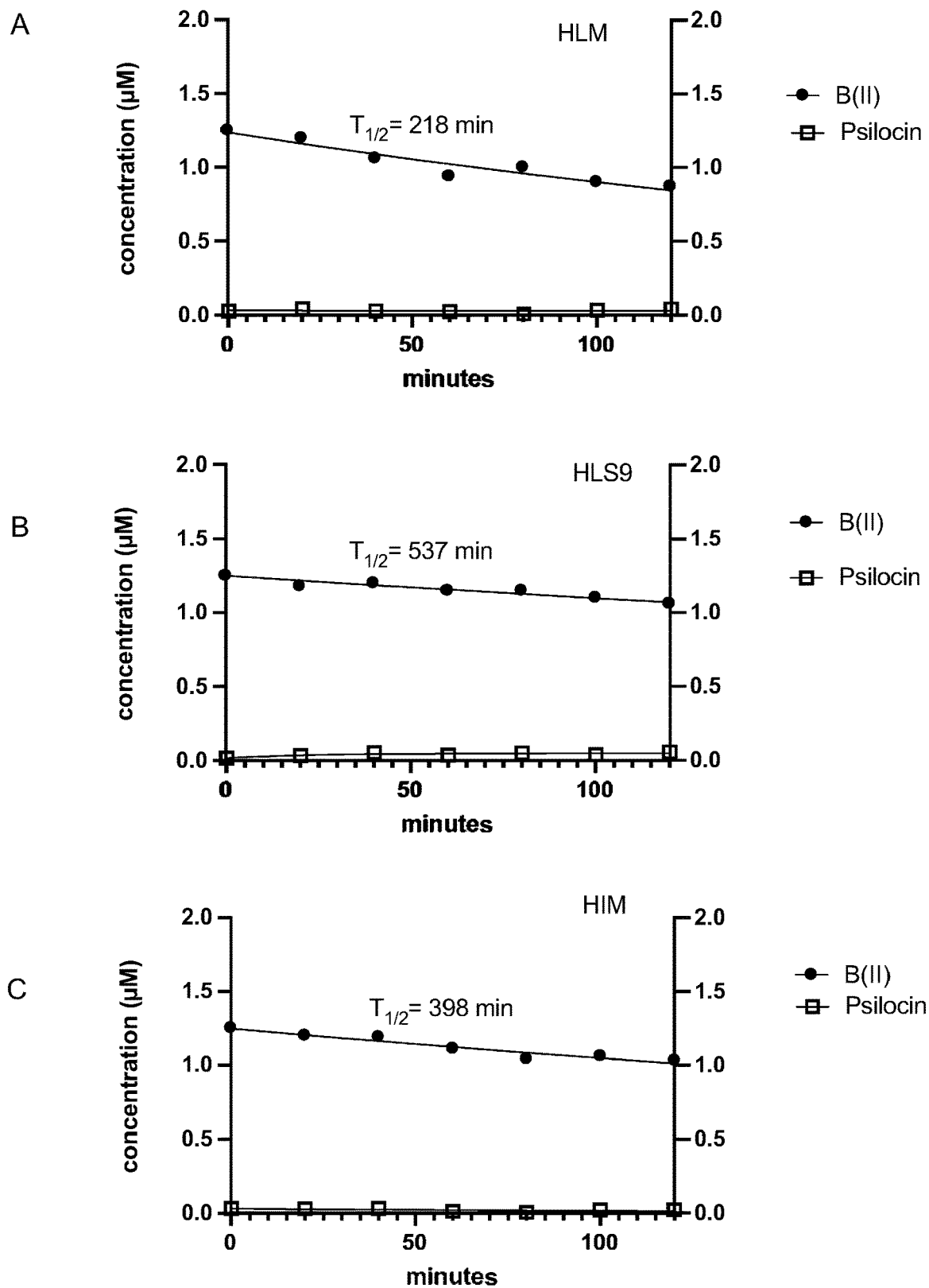
Figure 4E:
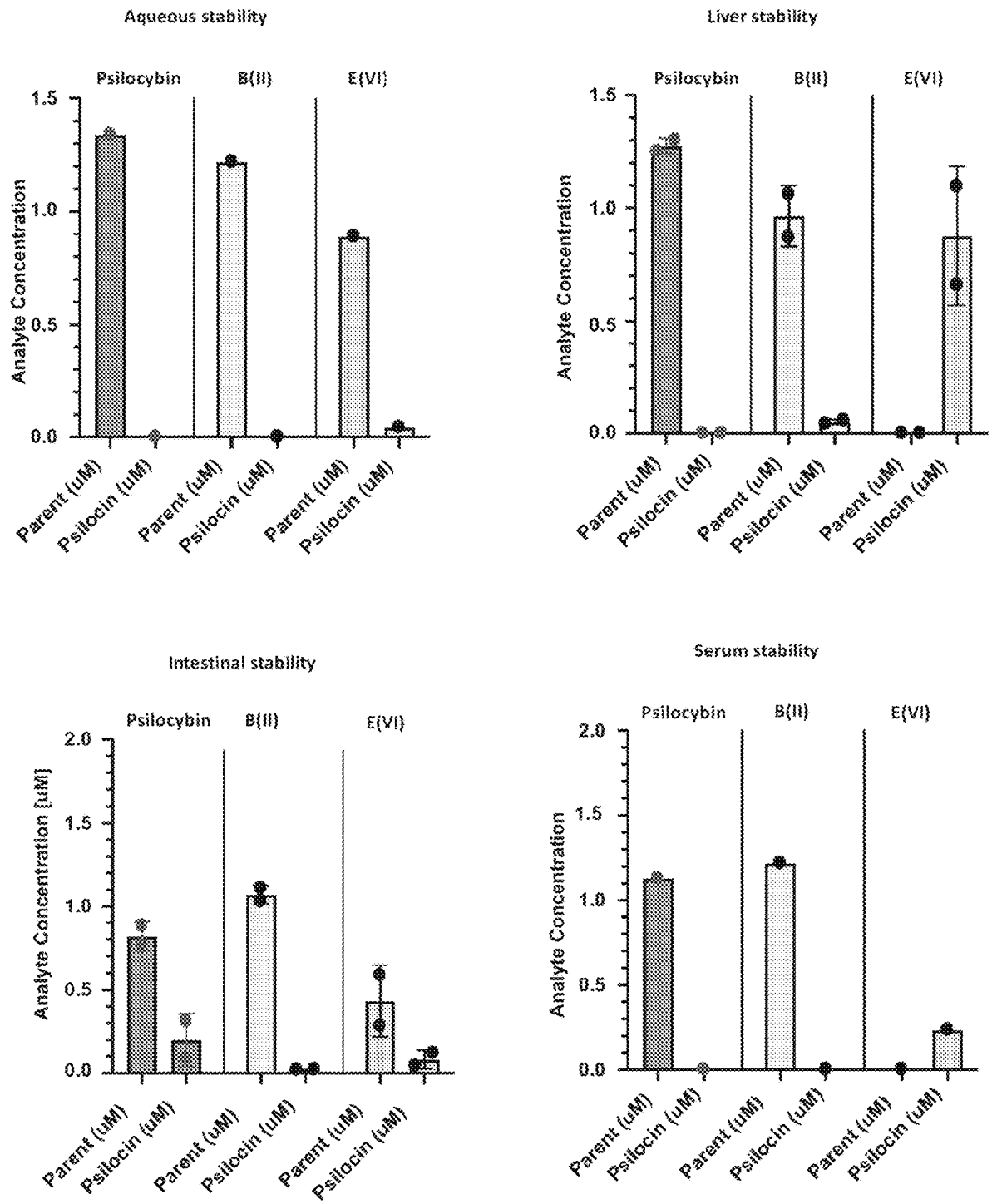

However, unexpected differences between B(II) and E(VI) were observed upon conducting in vitro metabolic stability assays. Evaluations of metabolic stability and capacity of novel molecules to release psilocin under various in vitro conditions were performed as described in Example 1, except that compound B(II) was used in place of compound E(VI). FIGS. 4D (i), 4D (ii) show the metabolic stability curves B(II) in HLM (Panel A), HLS9 (Panel B), HIM (Panel C), HIS9 (Panel D), AB serum (Panel E), and buffer control (Panel F). These results showed the unexpected stability of B(II), which did not readily dissociate to psilocin under any conditions. By contrast, E(VI) was quickly converted to psilocin in liver fractions and serum (FIGS. 3O (i), 3O (ii)). Whereas B(II) displayed half-lives ($T_{1/2}$) of 218 and 537 minutes in HLM and HLS9 fractions respectively, E(VI) was metabolized far more quickly (i.e., $T_{1/2}$ of 6 and 5 minutes in HLM and HLS9 fractions respectively). An even more pronounced difference was notable in AB serum, wherein B(II) failed completely to dissociate, but E(VI) rapidly metabolized ($T_{1/2}$ 14 minutes). For ease of comparison, B(II) and E(VI) data are summarized side-by-side in FIG. 4E, along with psilocybin control data. This summary clearly illustrates unique and different metabolic conversion profiles for psilocybin, B(II) and E(VI).

Figure 4F:
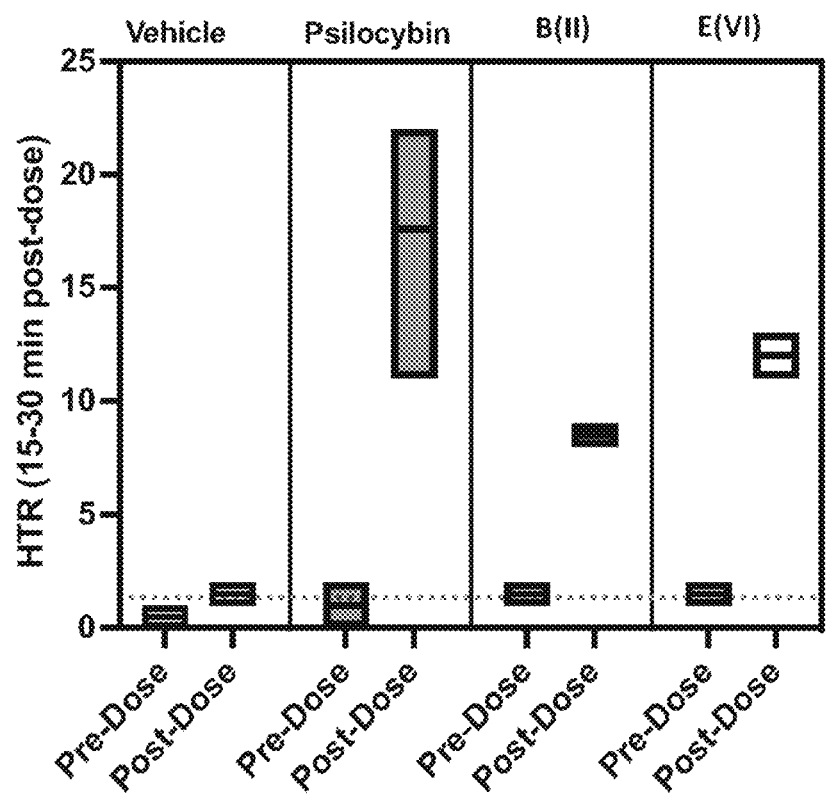

Further potentially meaningful differences between B(II) and E(VI) were observed during in vivo evaluation of 5-$HT_{2A}$ receptor agonism in mice. Evaluation of in vivo HTR was conducted as described in Example 1, except that compound B(II) was used in place of compound E(VI). For ease of comparison, B(II) and E(VI) data are summarized side-by-side in FIG. 4F, along with psilocybin control data. Although both molecules elicit head twitching, an elevated response was observed in mice treated with E(VI) compared to B(II).

In support of the in vitro metabolic conversion data, in vivo mouse pharmacokinetic (PK) evaluation of drug metabolism to psilocin revealed key differences between B(II) and E(VI). Pharmacokinetic (PK) evaluations were performed in the same manner as described in Example 1, except compound B(II) was used in place of compound E(VI). Congruent with in vitro data (FIGS. 4B, 4C), in vivo PK results highlight the relative stability of B(II) compared with E(VI) in mice orally dosed with 3 mg/kg and 10 mg/kg. Data in Table 15 show that B(II) resides in plasma up to 4 hours post-dosing (10 mg/kg) whereas E(VI) is never detected at any timepoint, suggesting slow metabolism of B(II) but quick metabolism of E(VI). Unfortunately, comparisons were not possible in mice orally dosed at 1 mg/kg as neither B(II) nor E(VI) were detected in plasma. Further, data featuring large standard deviations (e.g., Tables 7A, 7B) prevented meaningful comparison between mice dosed intravenously.

The PK profile of psilocin was also different in mice dosed with B(II) compared with E(VI). Data in Tables 16 and 17 show higher psilocin levels in B(II)-treated mice, leading to overall greater psilocin exposure in these animals during the sampling period. That B(II) displays greater stability than E(VI) under a variety of in vitro and in vivo conditions, yet mice treated with B(II) appear to harbour greater psilocin levels, can be reconciled in a number of possible ways. First, it's possible that E(VI) instability in plasma (FIGS. 3O (i) 3O (ii), 4E) caused rapid degradation to psilocin, which in turn was sufficiently metabolized such that the "peak" psilocin concentration ($C_{max}$) occurred prior to the first sampling time (0.25 hours post-dosing). As B(II) is comparatively stable in plasma, relying instead on slow metabolism in liver and/or intestines (FIGS. 4D (i), 4D (ii), 4E), sampling between 0.25 and 24 hours may have allowed a more accurate estimate of $C_{max}$ and exposure. Secondly, E(VI) may not be converted directly, or exclusively, to psilocin. It is possible that intermediate or off-pathway catabolites occur. In support of this notion, E(VI) nearly completely disappears upon in vitro exposure to AB serum, but yields low quantities of psilocin far from the expected 1:1 molar ratio of E(VI):psilocin (FIGS. 3O (i), 3O (ii)). In turn, B(II) may catabolize in greater abundance to psilocin and avoid off-target pathways or intermediates.

Yet further differences between B(II) and E(VI) were observed upon an in vitro survey of pharmacological interaction profiles. All assays were performed as described using "SAFETYscan E/IC150 ELECT" (https://www.eurofinsdiscoveryservices.com/) except compound B(II) was used in place of E(VI). For ease of comparison, Table 18 summarizes data for both B(II) and E(VI), respectively. Several assays revealed differences between B(II) and E(VI) behavior. For example, B(II) failed to elicit a response ($EC_{50}$>100 µM, or $IC_{50}$>100 µM; Table 18) in CHRM2 (antagonist mode) and OPRD1 (agonist mode) assays, whereas E(VI) elicited a response in both cases ($IC_{50}$=51.24 µM and $EC_{50}$=28.52 µM, respectively). Furthermore, E(VI) failed to elicit a response ($IC_{50}$>100 µM; Table 18) in AVPR1A (antagonist mode) and MAO-A (inhibitor mode) assays, whereas B(II) elicited a response in both cases ($IC_{50}$=42.64 µM and $IC_{50}$=21.86 µM, respectively).

Thus, in summary, this Example 2 documents substantive differences in chemical as well as pharmacological attributes when compounds E(VI) and B(II) are compared. Notably, when E(VI) and B(II) are evaluated in various pharmacological assays, the two compounds exhibit unexpectedly substantially different pharmacological attributes. These differences in pharmacological attributes are deemed particularly surprising in light of the structural similarities between E(VI) and B (II).

TABLE 15

Mean plasma concentrations of B(II) or E(VI) derivative (ng/mL) following oral administration of B(II) or E(VI) derivative. Fields marked (nd) indicate compound was either not detected or fell below acceptable limits of detection. Mean values ± SD were derived from n = 3 mice unless otherwise indicated.

| Time | 3 mg/kg | | 10 mg/kg | |
|---|---|---|---|---|
| (h) | B(II) | E(VI) | B(II) | E(VI) |
| 0.25 | 0.162 (n = 2) | nd | 0.994 ± 0.145 | nd |
| 0.5 | 0.162 (n = 1) | nd | 0.584 ± 0.186 | nd |
| 1 | nd | nd | 0.272 ± 0.123 | nd |
| 2 | nd | nd | 0.141 (n = 2) | nd |
| 4 | nd | nd | 0.164 (n = 1) | nd |
| 6 | nd | nd | nd | nd |
| 8 | nd | nd | nd | nd |
| 24 | nd | nd | nd | nd |

TABLE 16

Mean plasma concentrations of psilocin (ng/ml) following oral administration of B(II) or E(VI) derivative. Fields marked (nd) indicate psilocin was either not detected or fell below acceptable limits of detection. Mean ± SD were derived from n = 3 mice unless otherwise indicated.

| Time | 1 mg/kg | | 3 mg/kg | | 10 mg/kg | |
|---|---|---|---|---|---|---|
| (h) | B(II) | E(VI) | B(II) | E(VI) | B(II) | E(VI) |
| 0.25 | 19.7 ± 5.50 | 6.71 ± 1.63 | 55.6 ± 8.67 | 20.8 ± 6.46 | 306 ± 34.6 | 55.8 ± 21.9 |
| 0.5 | 11.9 ± 2.03 | 5.23 ± 0.640 | 32.3 ± 4.98 | 23.7 ± 6.32 | 125 ± 16.3 | 80.1 ± 28.6 |
| 1 | 4.63 ± 0.788 | 3.30 ± 0.606 | 9.29 ± 3.05 | 10.9 ± 2.32 | 49.6 ± 10.5 | 43.5 ± 1.75 |
| 2 | 2.20 ± 0.850 | 1.94 ± 0.508 | 7.67 ± 0.921 | 4.13 ± 1.10 | 20.7 ± 1.42 | 23.6 ± 8.45 |
| 4 | 2.05 ± 0.359 | 0.609 ± 0.143 | 6.76 ± 2.13 | 1.31 ± 0.351 | 31.4 ± 6.34 | 4.13 ± 1.48 |
| 6 | 0.739 ± 0.288 | 0.433 ± 0.301 | 2.41 ± 0.845 | 0.719 ± 0.465 | 11.5 ± 1.43 | 4.23 ± 3.52 |
| 8 | 0.453 ± 0.0460 | 0.188 (n = 2) | 0.722 ± 0.368 | 0.503 ± 0.346 | 6.38 ± 2.98 | 3.06 ± 1.99 |
| 24 | nd | nd | nd | nd | 0.104 (n = 1) | nd |

TABLE 17

Summary of mean plasma exposure of psilocin as a function of B(II) or E(VI) dose. Mean ± SD were derived from n = 3 mice unless otherwise indicated.

| | 1 mg/kg | | 3 mg/kg | | 10 mg/kg | |
|---|---|---|---|---|---|---|
| | B(II) | E(VI) | B(II) | E(VI) | B(II) | E(VI) |
| $C_{max}$/Dose (kg*ng/ml/mg) | 19.7 ± 5.50 | 6.74 ± 1.59 | 18.5 ± 2.89 | 8.49 ± 1.46 | 30.6 ± 3.46 | 8.01 ± 2.86 |
| Apparent $t_{1/2}$ (h) | 1.69 ± 0.107 | 1.66 ± 0.577 | 1.23 ± 0.202 | 2.88 ± 1.29 | 1.84 ± 0.538 | 1.39 (n = 1) |
| $AUC_{0-tlast}$/Dose$^a$ (h*kg*ng/ml/mg) | 21.0 ± 1.55 | 10.7 ± 0.442 | 20.3 ± 2.78 | 10.5 ± 0.544 | 28.2 ± 4.12 | 12.3 ± 0.231 |

TABLE 18

Data summary table of target assays for compounds B(II), E(VI) and control (C) ligands. Potency ($EC_{50}$ or $IC_{50}$) is provided in units of μM. AGN, agonist; ANT, antagonist; OP, opener; BL, blocker; IN, inhibitor. Note that 'C' refers to control compounds listed in Table 13.

| Target name | Target type | Assay type | $EC_{50}$ C | $IC_{50}$ C | $EC_{50}$ B(II) | $IC_{50}$ B(II) | $EC_{50}$ E(VI) | $IC_{50}$ E(VI) |
|---|---|---|---|---|---|---|---|---|
| ADRA1A | GPCR | AGN | 5.00E-05 | — | >100 | — | >100 | — |
| ADRA1A | GPCR | ANT | — | 9.60E-04 | — | 3.66 | — | 1.09 |
| ADRA2A | GPCR | AGN | 4.00E-05 | — | >100 | — | >100 | — |
| ADRA2A | GPCR | ANT | — | 3.10E-03 | — | 9.08 | — | 19.78 |
| AVPR1A | GPCR | AGN | 4.20E-04 | — | >100 | — | >100 | — |

TABLE 18-continued

Data summary table of target assays for compounds B(II), E(VI) and control (C) ligands. Potency ($EC_{50}$ or $IC_{50}$) is provided in units of μM. AGN, agonist; ANT, antagonist; OP, opener; BL, blocker; IN, inhibitor. Note that 'C' refers to control compounds listed in Table 13.

| Target name | Target type | Assay type | $EC_{50}$ C | $IC_{50}$ C | $EC_{50}$ B(II) | $IC_{50}$ B(II) | $EC_{50}$ E(VI) | $IC_{50}$ E(VI) |
|---|---|---|---|---|---|---|---|---|
| AVPR1A | GPCR | ANT | — | 1.60E−03 | — | 42.64 | — | >100 |
| CHRM1 | GPCR | AGN | 9.70E−03 | — | >100 | — | >100 | — |
| CHRM1 | GPCR | ANT | — | 6.10E−03 | — | 24.54 | — | 15.1 |
| CHRM2 | GPCR | AGN | 2.70E−02 | — | >100 | — | >100 | — |
| CHRM2 | GPCR | ANT | — | 3.20E−03 | — | >100 | — | 51.24 |
| CNR1 | GPCR | AGN | 1.00E−05 | — | >100 | — | >100 | — |
| CNR1 | GPCR | ANT | — | 6.20E−04 | — | 68.63 | — | 96.99 |
| DRD1 | GPCR | AGN | 9.10E−02 | — | >100 | — | >100 | — |
| DRD1 | GPCR | ANT | — | 7.10E−04 | — | 5.39 | — | 7.11 |
| DRD2S | GPCR | AGN | 5.10E−04 | — | >100 | — | >100 | — |
| DRD2S | GPCR | ANT | — | 9.60E−04 | — | 12.39 | — | 13.28 |
| HTR1A | GPCR | AGN | 1.70E−03 | — | 13.6 | — | 11.36 | — |
| HTR1A | GPCR | ANT | — | 4.60E−02 | — | >100 | — | >100 |
| HTR1B | GPCR | AGN | 9.00E−05 | — | 4.46E−01 | — | 2.36E−01 | — |
| HTR1B | GPCR | ANT | — | 5.80E−03 | — | >100 | — | >100 |
| HTR2B | GPCR | AGN | 6.30E−04 | — | >100 | — | >100 | — |
| HTR2B | GPCR | ANT | — | 4.00E−04 | — | 2.81E−01 | — | 8.57E−02 |
| OPRD1 | GPCR | AGN | 5.00E−05 | — | >100 | — | 28.52 | — |
| OPRD1 | GPCR | ANT | — | 5.80E−04 | — | >100 | — | >100 |
| GABAA | Ion channel | OP | 6.2 | — | >100 | — | >100 | — |
| GABAA | Ion channel | BL | — | 4.6 | — | 21 | — | 32.17 |
| HTR3A | Ion channel | OP | 3.00E−01 | — | >100 | — | >100 | — |
| HTR3A | Ion channel | BL | — | 1.90E−03 | — | 2.34 | — | 1.87 |
| MAO-A | Enzyme | IN | — | 2.90E−03 | — | 21.86 | — | >100 |
| DAT | transporter | BL | — | 1.40E−03 | — | 4.69 | — | 1 |
| NET | transporter | BL | — | 6.70E−03 | — | 26.53 | — | 9.25 |
| SERT | transporter | BL | — | 1.80E−03 | — | 10.36 | — | 9.06 |
| NMDAR | Ion channel | BL | — | 8.00E−02 | — | 16.02 | — | 15 |
| NMDAR | Ion channel | OP | 4.40E−01 | — | >100 | — | >100 | — |

The invention claimed is:

1. A method of making a chemical compound having chemical formula (VI):

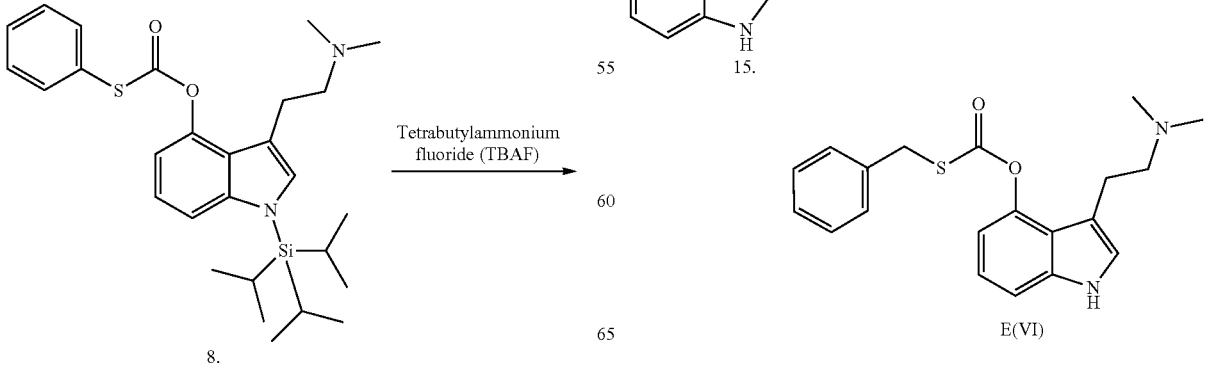

wherein the method comprises the performance of one of the chemical reactions selected from (h) and (i):

under reaction conditions sufficient to convert compound 8 or compound 15 to form compound E(VI).

2. The method according to claim 1, wherein the concentration TBAF in chemical reaction (h) ranges from 0.1 M to 1.5 M.

3. The method according to claim 1, wherein the concentration TBAF in chemical reaction (h) is selected from 0.75 M, 0.9 M, 1 M, 1.1M, and 1.25 M TBAF in tetrahydrofuran.

4. The method according to claim 1, wherein the performance of chemical reaction (h) comprises: (i) adding TBAF at 0° C. to compound 8 to obtain a first reaction mixture comprising compound E(VI); (ii) adding water to the reaction mixture to obtain a second reaction mixture comprising an aqueous phase; (iii) separating the aqueous phase from the second reaction mixture; and (iv) extracting compound E(VI) with dichloromethane from the separated aqueous phase.

5. The method according to claim 1, wherein compound 8 is formed by performing chemical reaction (g):

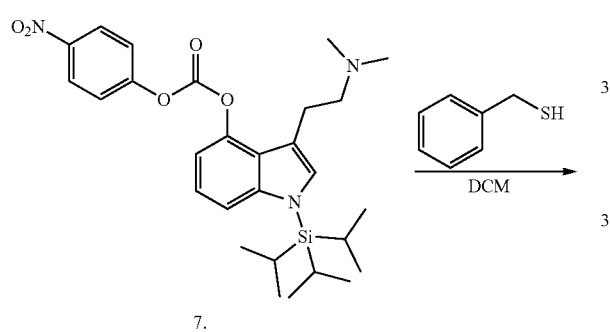

6. The method according to claim 5, wherein compound 7 is formed by performing chemical reaction (f):

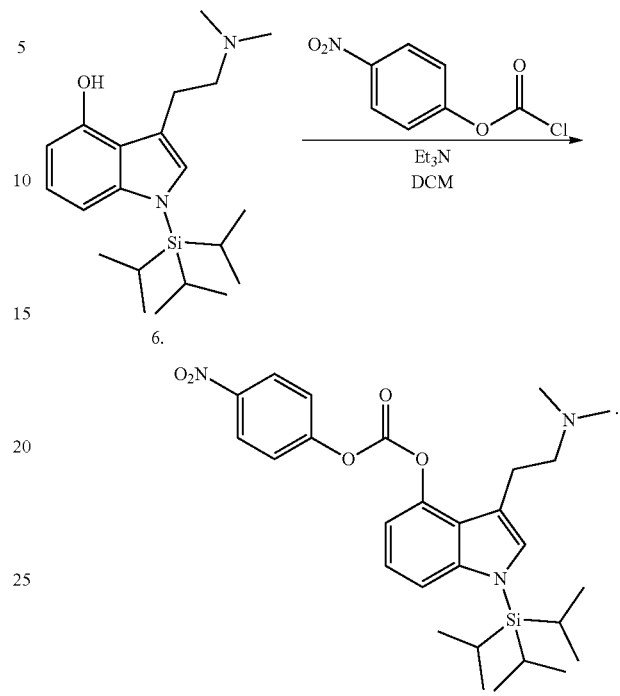

7. The method according to claim 6, wherein compound 6 is formed by performing chemical reaction (e):

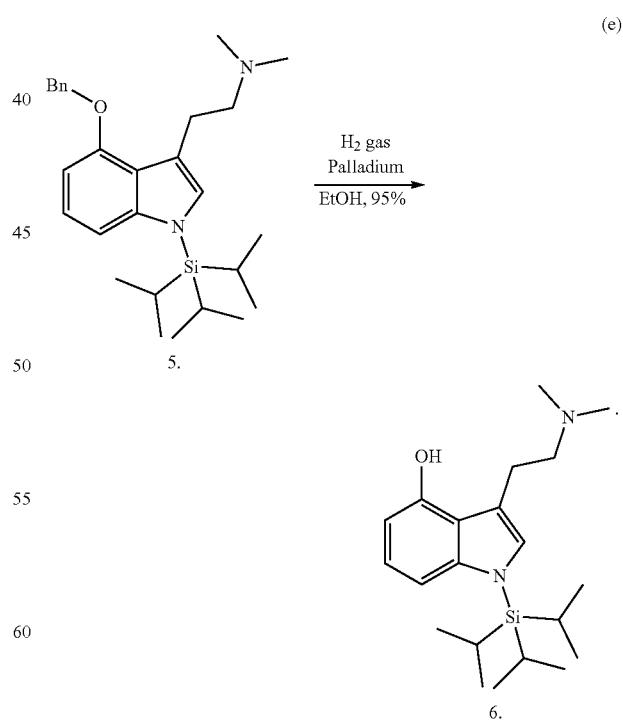

8. The method according to claim 7, wherein compound 5 is formed by performing chemical reaction (d):

(d)

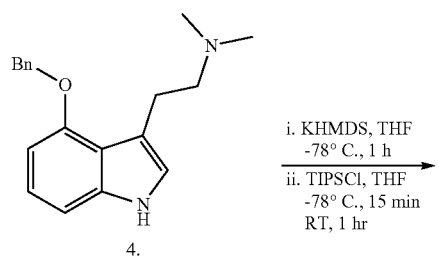

i. KHMDS, THF
 -78° C., 1 h
ii. TIPSCl, THF
 -78° C., 15 min
 RT, 1 hr

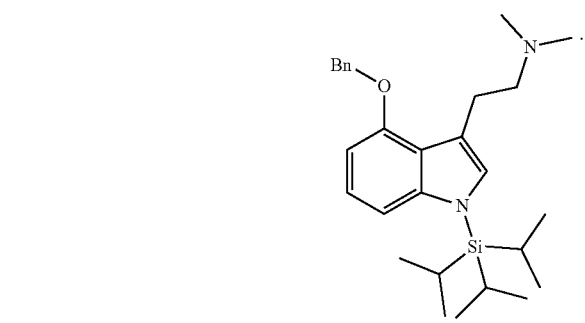

9. The method according to claim 8, wherein compound 4 is formed by performing chemical reaction (c):

(c)

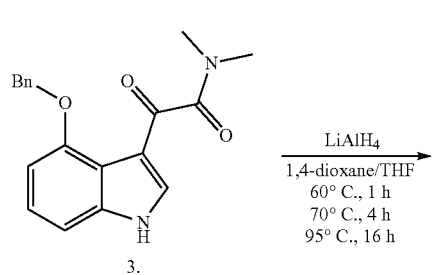

LiAlH$_4$
1,4-dioxane/THF
60° C., 1 h
70° C., 4 h
95° C., 16 h

10. The method according to claim 9, wherein compound 3 is formed by performing chemical reaction (b):

(b)

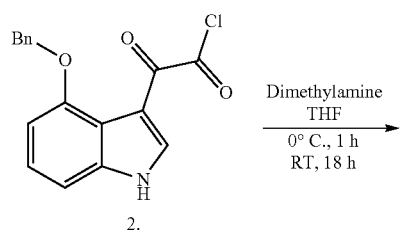

Dimethylamine
THF
0° C., 1 h
RT, 18 h

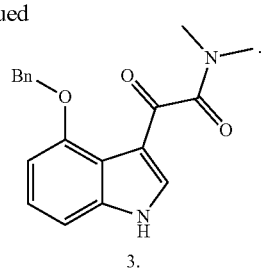

11. The method according to claim 10, wherein compound 2 is formed by performing chemical reaction (a):

(a)

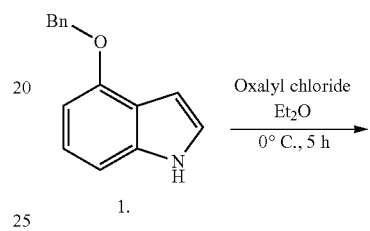

Oxalyl chloride
Et$_2$O
0° C., 5 h

12. The method according to claim 1, wherein chemical reaction (1) is performed by adding to a solution of compound 15 and potassium carbonate in dimethyl formamide (DMF) a solution of benzylchlorothioformate.

13. The method according to claim 1, wherein chemical reaction (1) is performed at room temperature for at least 6 hours.

14. The method according to claim 1, wherein compound 15 is formed by performing chemical reaction (k):

(k)

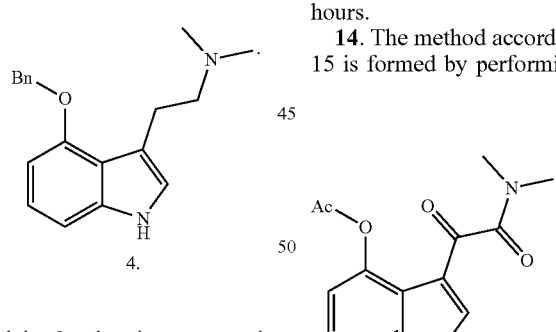

LiAlH$_4$

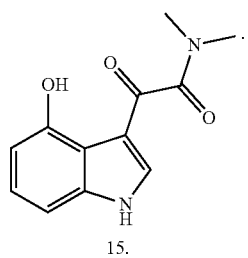

15. The method according to claim 14, wherein compound 14 is formed by performing chemical reaction (j):
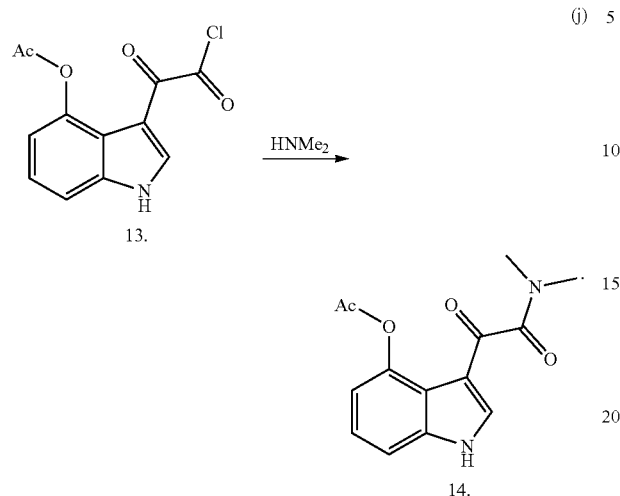
16. The method according to claim 14, wherein compound 13 is formed by performing chemical reaction (z):
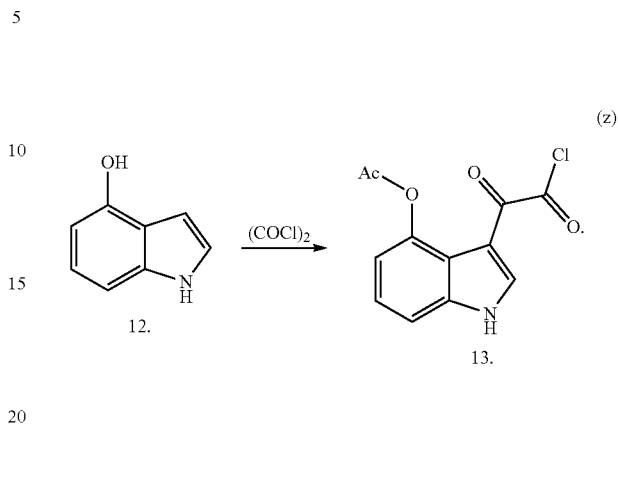
* * * * *

UNITED STATES PATENT AND TRADEMARK OFFICE
CERTIFICATE OF CORRECTION

PATENT NO. : 11,845,726 B2  
APPLICATION NO. : 17/893113  
DATED : December 19, 2023  
INVENTOR(S) : Jillian M. Hagel, Kaveh Matinkhoo and Peter J. Facchini Page 1 of 1

It is certified that error appears in the above-identified patent and that said Letters Patent is hereby corrected as shown below:

In the Claims

In Claim 1, at Column 70, Line 46, amend "(I)" to "(i)"

In Claim 12, at Column 74, Line 36, amend "(1)" to "(i)"

In Claim 13, at Column 74, Line 40, amend "(1)" to "(i)"

In Claim 14, at Column 74, Line 55, amend " 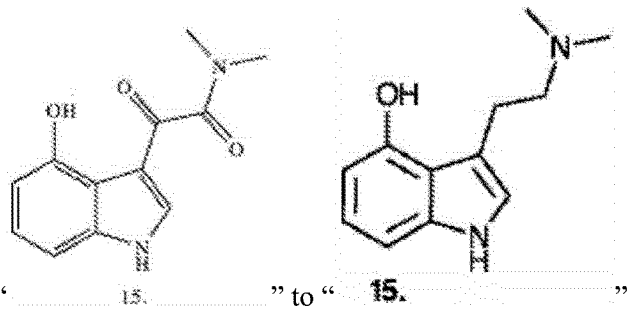 "

Signed and Sealed this  
Eighteenth Day of June, 2024

Katherine Kelly Vidal  
*Director of the United States Patent and Trademark Office*